(12) United States Patent
Feldman et al.

(10) Patent No.: US 7,801,590 B2
(45) Date of Patent: Sep. 21, 2010

(54) OPTICAL COHERENCE TOMOGRAPHIC DETECTION OF CELLS AND KILLING OF THE SAME

(75) Inventors: Marc D. Feldman, San Antonio, TX (US); Thomas E. Milner, Austin, TX (US); Jihoon Kim, Austin, TX (US); Junghwan Oh, Houston, TX (US); Pramod Sanghi, Bloomfield, MI (US); Jake Mancuso, San Antonio, TX (US); Keith P. Johnston, Austin, TX (US); Leo Ma, Austin, TX (US); Stas Emelianov, Austin, TX (US)

(73) Assignee: Board of Regents, the University of Texas System, Austin, TX (US)

( * ) Notice: Subject to any disclaimer, the term of this patent is extended or adjusted under 35 U.S.C. 154(b) by 252 days.

(21) Appl. No.: 11/784,477

(22) Filed: Apr. 6, 2007

(65) Prior Publication Data

US 2007/0260138 A1      Nov. 8, 2007

Related U.S. Application Data

(63) Continuation-in-part of application No. 11/441,824, filed on May 26, 2006.

(60) Provisional application No. 60/790,248, filed on Apr. 7, 2006, provisional application No. 60/685,559, filed on May 27, 2005.

(51) Int. Cl.
*A61B 6/00* (2006.01)
(52) U.S. Cl. .................................................. 600/476
(58) Field of Classification Search ................. 600/476; 356/450, 456, 477, 517
See application file for complete search history.

(56) References Cited

U.S. PATENT DOCUMENTS

| 5,262,176 A | 11/1993 | Palmacci et al. | |
|---|---|---|---|
| 5,921,244 A | * 7/1999 | Chen et al. | 128/897 |
| 6,191,862 B1 | * 2/2001 | Swanson et al. | 356/479 |
| 6,530,944 B2 | * 3/2003 | West et al. | 607/88 |
| 6,608,684 B1 | * 8/2003 | Gelikonov et al. | 356/479 |

(Continued)

FOREIGN PATENT DOCUMENTS

WO          WO 96/23524          2/1996

(Continued)

OTHER PUBLICATIONS

Alder DC, Huber R, and Fujimoto JG. Phase-sensitive optical coherence tomography at up to 370,000 lines per second using buffered Fourier domain mode-locked lasers. *Optics Letters*, 2007; 32: 626-628.

(Continued)

*Primary Examiner*—Long V Le
*Assistant Examiner*—Jacqueline Cheng
(74) *Attorney, Agent, or Firm*—J. Peter Paredes; Rosenbaum & Silvert, P.C.

(57) ABSTRACT

Provided herein are systems, methods and compositions for the use of optical coherence tomography for detection of cells and for killing detected cells. A detected cell can be killed or injured by contacting a composition comprised by the cell with energy. Energy can be applied to a particle comprised by the cell.

68 Claims, 22 Drawing Sheets

U.S. PATENT DOCUMENTS

| | | | |
|---|---|---|---|
| 2002/0198457 | A1 | 12/2002 | Tearney et al. |
| 2003/0064965 | A1* | 4/2003 | Richter ........................ 514/102 |
| 2004/0023415 | A1 | 2/2004 | Sokolov et al. |
| 2004/0098070 | A1* | 5/2004 | Mohr et al. .................... 607/89 |
| 2005/0171433 | A1* | 8/2005 | Boppart et al. .............. 600/473 |
| 2007/0038121 | A1 | 2/2007 | Feldman et al. |
| 2007/0168001 | A1* | 7/2007 | Xiang et al. ................ 607/101 |

FOREIGN PATENT DOCUMENTS

| | | |
|---|---|---|
| WO | WO 99/13916 | 3/1999 |
| WO | WO 2004/096049 | 4/2004 |
| WO | WO 2006/020903 | 2/2006 |

OTHER PUBLICATIONS

Anderson RR Parrish JA. Selective photothermolysis: precise microsurgery by selective absorption of pulsed radiation. *Science*, 1983; 220: 524-527.

Aslan K, Lakowicz Jr, Geedes CD. Tunable plasmonic glucose sensing based on the dissociation of Con A aggregated dextran-coated gold colloids. *Analytica Chimica Acta*, 2004; 517: 139-144.

Brezinski ME, Tearney GJ, Bouma BE, Izatt JA, Hee MR, Swanson EA, Southern JM, Fujimoto JG. Optical coherence tomography for optical biopsy. *Circulation*, 1996; 93:1206-1213.

Caplan JD, Waxman S. Nesto RW, Muller JE. Near-Infrared Spectroscopy for the Detection of Vulnerable Coronary Artery Plaques. *JACC*, 2006; 47:C92-96.

Cilingiroglu, et al., "Detection of Vulnerable Plaque in a Murine Model of Atherosclerosis With Optical Coherence Tomography," Catheterization *and Cardiovascular Interventions*, 67:915-923 (2006).

Daniel MD, Astruc D. Gold nanoparticles: assembly, superamolecular chemistry and application toward biology, catalysis and nanotechnology. *Chem Rev*, 2004; 104: 293-346.

Dave DP, Milner TE. Optical low-coherence reflectometer for differential phase measurement. *Optical Letters*, 2000; 25: 227-229.

Elghanian, R., et al., Selective Colorimetric Detection Of Polynucleotides Based On The Distance-Dependent Optical Properties Of Gold Nanoparticles. *Science*, 277(5329): 1078-1080 (1997).

Fujimoto JG, Boppart SA, Tearney GJ, Bouma BE, Pitris C, Brezinski ME. High resolution in vivo intra-arterial imaging with optical coherence tomography. *Heart*, 1999; 82:128-133.

Huber R, Adler DC, Fujimoto JG. Buffered Fourier domain mode locking: unidirectional swept laser sources for optical coherence tomography imaging at 370,000 lines/s. *Optics Letters*, 2006; 31: 2975-2977.

Huber R, Wojtkowski M, Fujimoto JG. Fourier Domain Mode Locking (FDML): A new laser operating regime and applications for optical coherence tomography. *Optics Express*, 2006; 14: 3225-3237.

Jang IK, Bouma BE, Kang DH, Park SJ, Park SW, Seung KB, Choi KB, Shishkov M, Schlendorf K, Pomerantsev E, Houser SL, Aretz T, Tearney GJ. Visualization of coronary atherosclerotic plaques in patients using optical coherence tomography: comparison with intravascular ultrasound. *JACC*, 2002; 39:604-609.

Johnson J, Carson K, Williams H, Karanam S, Newby A, Angelini G, George S, Jackson C. Plaque rupture after short periods of fat feeding in the apolipoprotein E-knockout mouse: model characterization and effects of Pravastatin treatment. *Circulation*, 2005; 111: 1422-1430.

Josephson L, Tung CH, Moore A, Weissleder R. High-efficiency intracellular magnetic labeling with novel superparamagnetic-tat peptide conjugates. *Bioconjugate Chemistry*, 1999; 10: 186-191.

Kelly et al., "Detection of Vascular Adhesion Molecule-1 Expression Using a Novel Multimodal Nanoparticle,"*Circulation Res.*, 96:327-336 (2005).

Kuo WC, Chou NK, Chou C, et al. Polarization sensitive OCT for imaging human atherosclerosis. *Applied Optics In Press* 2007.

Landini L, Santarelli MF, Pingitore A, Positano V. New technological developments in the clinical imaging of atherosclerotic plaque. *Current Pharmaceutical Design*, 2003; 9:2403-2415.

Lee et al., "Engineered microsphere contrast agents for optical coherence tomography," *Optics Letters* 28(17) 1546-1548 (2003).

Leitgeb R, Hitzenberbger CK, Fercher AF. Performance of fourier domain vs time domain Optical Coherence Tomography. *Optics Express*, 2003; 11: 889-894.

Loo et al., "Nanoshell-Enabled Photonics-Based Imaging and Therapy of Cancer," *Tech. Cancer Res. and Treatment*, 3(1) 33-40 (2004).

MacNeill BD, Low HC, Masamichi T, Fuster V, Jang I. Intravascular modalities for detection of vulnerable plaque. *Arterioscler Thromb Vasc Biol*, 2003;23:1333-1342.

Mandel M, Kundu S, Ghosh SK, Panigrahi S, Sau TK, Yusuf SM, Pal T. Magnetite nanoparticles with tunable gold or silver shell. *Journal Colloid Interface Science*, 2005; 286: 187-194.

Mindlin, "Force at a Point in the Interior of a Semi-Infinite Solid," *Physics*, 7:195-202 (1936).

Moreno PR, Muller JE. Detection of high risk atherosclerotic coronary plaques by intravascular spectroscopy. *J Interven Cardiol*, 2003;16:243-252.

Mornet S, Vasseur S, Grasset F, Duguet E. Magnetic nanoparticle design for medical diagnosis and therapy. *J Mater Chem*, 2004; 14: 2161-2175.

Nakamura et al., "Identification and Treatment of Vulnerable Plaque," *Rev. in Cardiovascular Med.*, 5(Suppl. 2)S22-S33 (2004).

Nogueira GV, Silveira L, Martin AA, Zangaro RA, Pacheco MT, Chavantes MC, Pasoualucci CA. Raman spectroscopy study of atherosclerosis in human carotid artery. *J Biomed Opt*, 2005;10(3):031117.

Oh, et al., "Detection of Magnetic Nanoparticles in Tissue Using Magneto-Motive Ultrasound,"*Nanotechnology* 17:4183-4190 (2006).

Oh, et al., "Magneto-Motive Detection of Tissue-Based Macrophages by Differential Phase Optical Coherence Tomography," *Lasers in Surgery and Medicine*, Wiley-Liss, Inc. 1-5 (2007).

Oldenburg AL, Gunther JR, Boppart SA. Imaging magnetically labeled cells with magnetomotive optical coherence tomography. *Optics Letters*, 2005; 30:747-749.

Oldenburg et al., "Magnetic contrast agents for optical coherence tomography," Proc. SPIE 5316 26-28 (2004).

Oldenburg et al., "Nanoengineering of Optical Resonances," Chemical Physics Letters 288, 243-247 (1998).

Oldenburg SJ, Jackson JB, Westcott SL, Halas MJ. Infrared extinction properties of gold nanoshells. *Applied Physics Letters*, 1999; 75: 2897-2899.

Pitsillides CM, Joe EK, Wei X, Anderson RR, Lin CP. Selective cell targeting with light-absorbing microparticles and nanoparticles. *Biophysical Journal*, 2003; 84: 4023-4032.

Regar et al., "Optical Coherence Tomography," Cardiovascular Rad. Med., 4 198-204 (2003).

Reynolds F, O'Loughlin T, Weissleder R, Josephson L. Method of determining nanoparticle core weight. *Analytical Chemistry*, 2005; 77: 814-817.

Robles, "Short-Duration High-Frequency Quasi-Sinusoidal Magnetic Field Generator," *IEEE Transactions On Instrumentation And Measurement*, vol. 54, No. 6:2481-2485 (Dec. 2005).

Shen T, Weissleder R, Papisov M, Bogdanov A, Brady TJ. Manocrystalline iron oxide nanocompounds (MION): physicochemical properties. *Magnetic Resonance Medicine*, 1993; 29: 599-604.

Siiman O, Ledis S. Surface-enhanced raman scattering (SERS) of random silver or gold particle arrays on aminodextran-coated polystyrene beads. *Journal Raman Spectroscopy*, 2005; 36: 1125-1133.

Siiman O, et al., Fluorescent neoglycoproteins: antibody-aminodextran-phycobiliprotein conjugates. *Bioconjugate Chemistry*, 1999; 10: 1090-1106.

Silveira L Jr, et al., Correlation between near-infrared Raman spectroscopy and the histopathological analysis of atherosclerosis in human coronary arteries. Lasers Surg Med, 2002; 30(4):290-297.

Sirol et al., "Molecular Imaging for the Diagnosis of High-Risk Plaque," Cardiovascular Res., 96(12) 1219-1224 (2003).

Sun EY, Josephson L, Kelly KA, Weissleder R. Development of nanoparticle libraries for biosensing. *Bioconjugate Chemistry*, 2006; 17:109-113.

Sun U, Xia, U. Increased sensitivity of surface plasmon resonance of gold nanoshells compared to that of fold solid colloids in response to environmental changes. *Analytical Chemistry*, 2002; 74: 5297-5305.

Tearney et al., "Quantification of Macrophage Content in Atherosclerotic Plaques by Optical Coherence Tomography," Circulation, 107:113-119 (2003).

Vakoc BJ, Yun SH, de Boer JF, Tearney GJ, Bouma BE. Phase-resolved optical frequency domain imaging. *Optics Express*, 2005; 13: 5483-5493.

Villard, et al., "Use of a Blood Substitute to Determine Instantaneous Murine Right Ventribular Thickening With Optical Coherence Tomography,"Circulation: *Journal of the American Heart Association*, 105:1843-1849 (2002).

Wang L, Luo J, Fan Q, Suzuki M, Suzuki IS, Engelhard MH, Lin Y, Kim N, Wang JQ, Zhong CJ. Monodispersed core-shell $Fe_3O_4$@Au nanoparticles. *J Phys Chem B*, 2005; 109: 21593-21601.

Wang T, Ehteshami G, Massia S, Muthuswamy J. Immobilization and characterization of g-Aminobutyric acid on gold surface. *Journal Biomedical Materials Research, Part A*, 2006; 79A: 201-209.

Weissleder R, Kelly K, S un EY, Shtatland T, Josephson L. Cell-specific targeting of nanoparticles by multivalent attachment of small molecules. *Nature Biotechnology*, 2005; 23: 1418-1423.

Weissleder R. A clearer vision for in vivo imaging. *Nature Biotechnology*, 2001;19:316-317.

* cited by examiner

Phase Sensitive OCT System 100

Multi-Channel Phase Sensitive OCT System 200

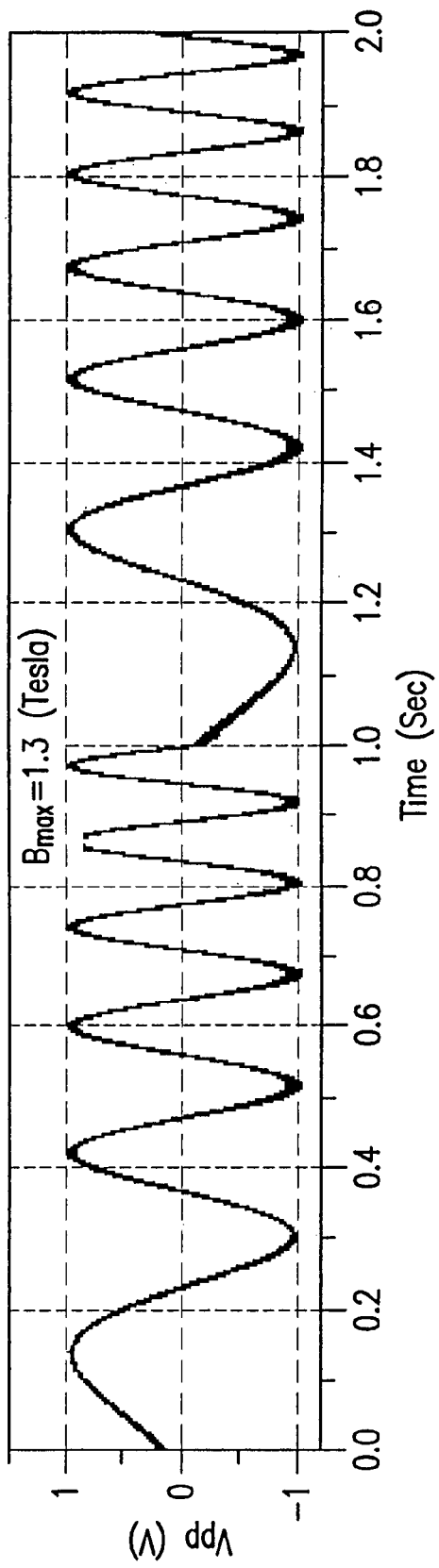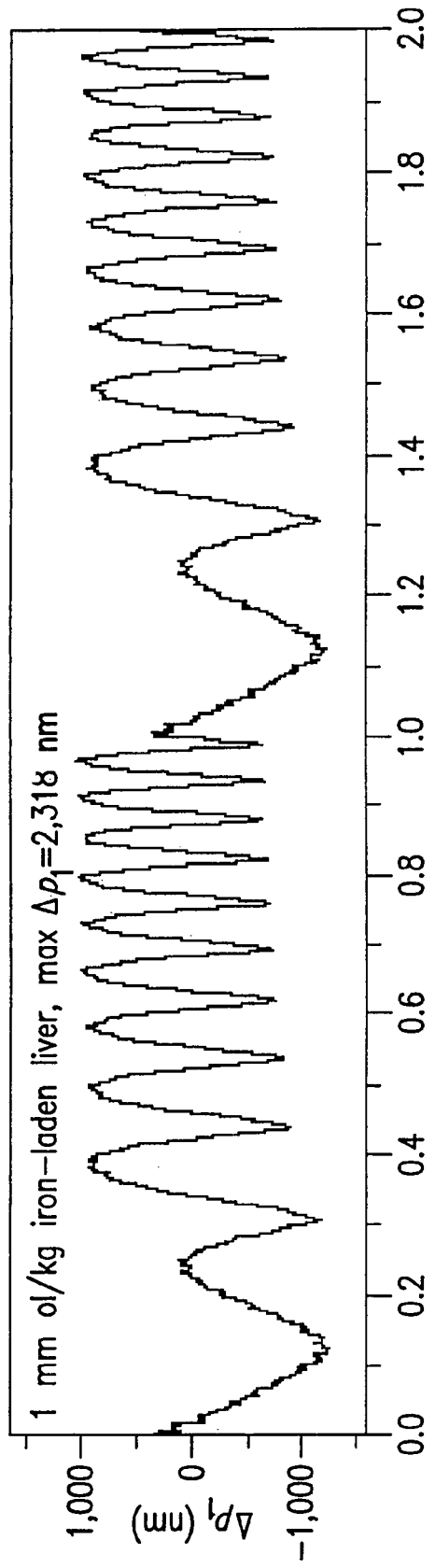
FIG. 9A
FIG. 9B

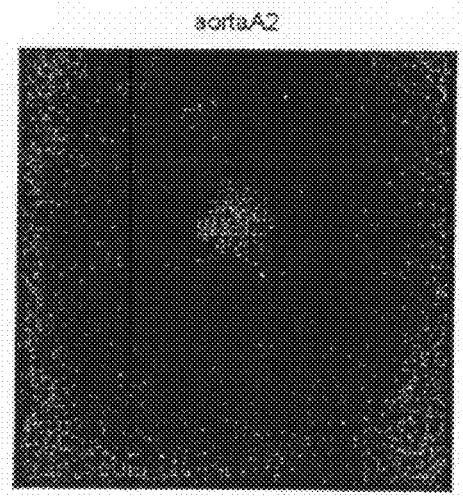
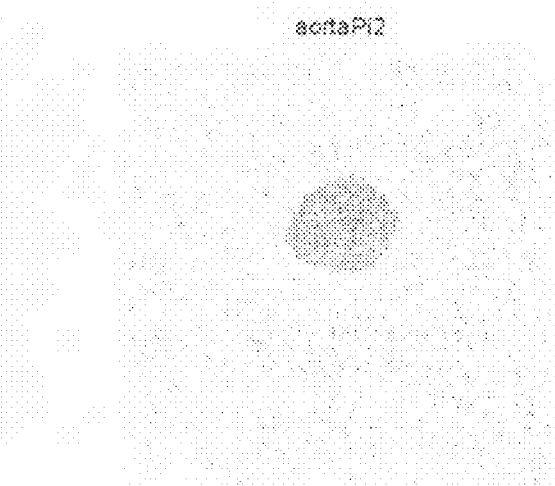
Figure 14a
Figure 14b
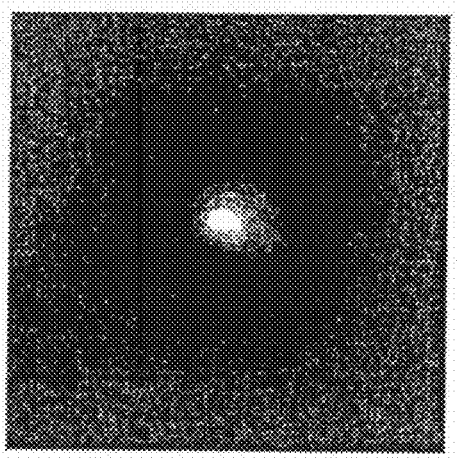
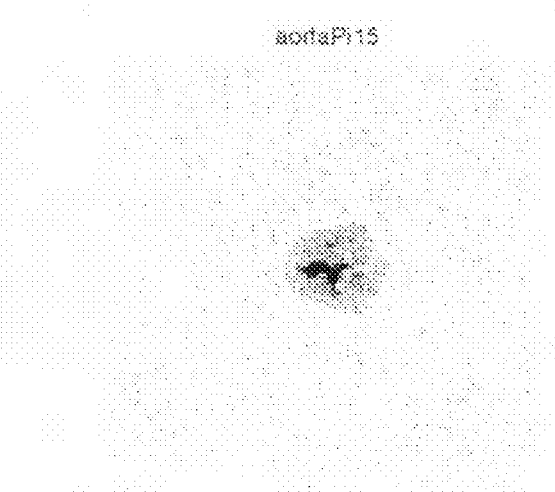
Figure 15a
Figure 15b

OPTICAL COHERENCE TOMOGRAPHIC DETECTION OF CELLS AND KILLING OF THE SAME

CROSS-REFERENCE TO RELATED APPLICATIONS

This application claims the benefit of U.S. Provisional Application No. 60/790,248 filed on Apr. 7, 2006, and is a continuation-in part of application Ser. No. 11/441,824, filed May 26, 2006, which claims the benefit of U.S. Provisional Application No. 60/685,559, filed on May 27, 2005. The aforementioned applications are herein incorporated by reference in their entirety.

BACKGROUND

Arteriosclerosis, also known as atherosclerosis, is a common human ailment arising from the deposition of fatty-like substances, referred to as atheromas or plaques, on the walls of blood vessels. While some plaques are relatively stable, others are vulnerable to rupture and release their contents into the bloodstream, causing a blood clot to form. Heart attacks and other acute cardiovascular events usually result from the rupture of high-risk, vulnerable plaques in coronary arteries. Vulnerable plaques are believed to have three major characteristics—a deposit of lipids, a thin cap of fibrous material covering the lipid pool, and infiltration of the immune cells called macrophages. Such deposits occur in both the peripheral blood vessels and the coronary vessels. When deposits accumulate in localized regions of a blood vessel, stenosis, or narrowing of the vascular channel occurs. Blood flow is restricted and the person's health is at serious risk. Early detection and characterization of arterial plaque can identify patients who are unaware that they are at risk of suffering a myocardial infarction or other cardiovascular events such as stroke.

Optical coherence tomography (OCT) has been used to successfully image various organs and tissues. OCT can produce a relatively high resolution image, especially when compared to other imaging modalities. OCT imaging of arterial plaques, however, has had limited success and has been unsatisfactory for identification of vulnerable plaques. Methods and apparatuses for high resolution OCT images are needed for imaging arterial plaques and for identifying vulnerable plaques. Moreover, similar methods and apparatuses are needed for imaging of other normal and diseased tissues, compositions, cells, and pathologies in a subject, including cancer and pre-cancerous conditions.

SUMMARY

Provided herein are systems, methods and compositions for the detection of cells using optical coherence tomography and killing of detected cells.

The methods, systems, and apparatuses are set forth in part in the description which follows, and in part will be obvious from the description, or can be learned by practice of the methods, apparatuses, and systems. The advantages of the methods, apparatuses, and systems will be realized and attained by means of the elements and combinations particularly pointed out in the appended claims. It is to be understood that both the foregoing general description and the following detailed description are exemplary and explanatory only and are not restrictive of the methods, apparatuses, and systems, as claimed.

BRIEF DESCRIPTION OF THE DRAWINGS

The accompanying drawings, which are incorporated in and constitute a part of this specification, illustrate aspects of the methods, apparatuses, and systems and together with the description, serve to explain the principles of the methods, apparatuses, and systems.

FIGS. 14A and B show pulsed laser images from an atherosclerotic rabbit thoracic aorta injected with saline 48 hours prior to imaging with optical coherence tomography.

FIGS. 15A and B show pulsed laser images from an atherosclerotic rabbit thoracic aorta injected with iron oxide nanoparticles 48 hours prior to imaging with optical coherence tomography.

DETAILED DESCRIPTION

Figure 1:
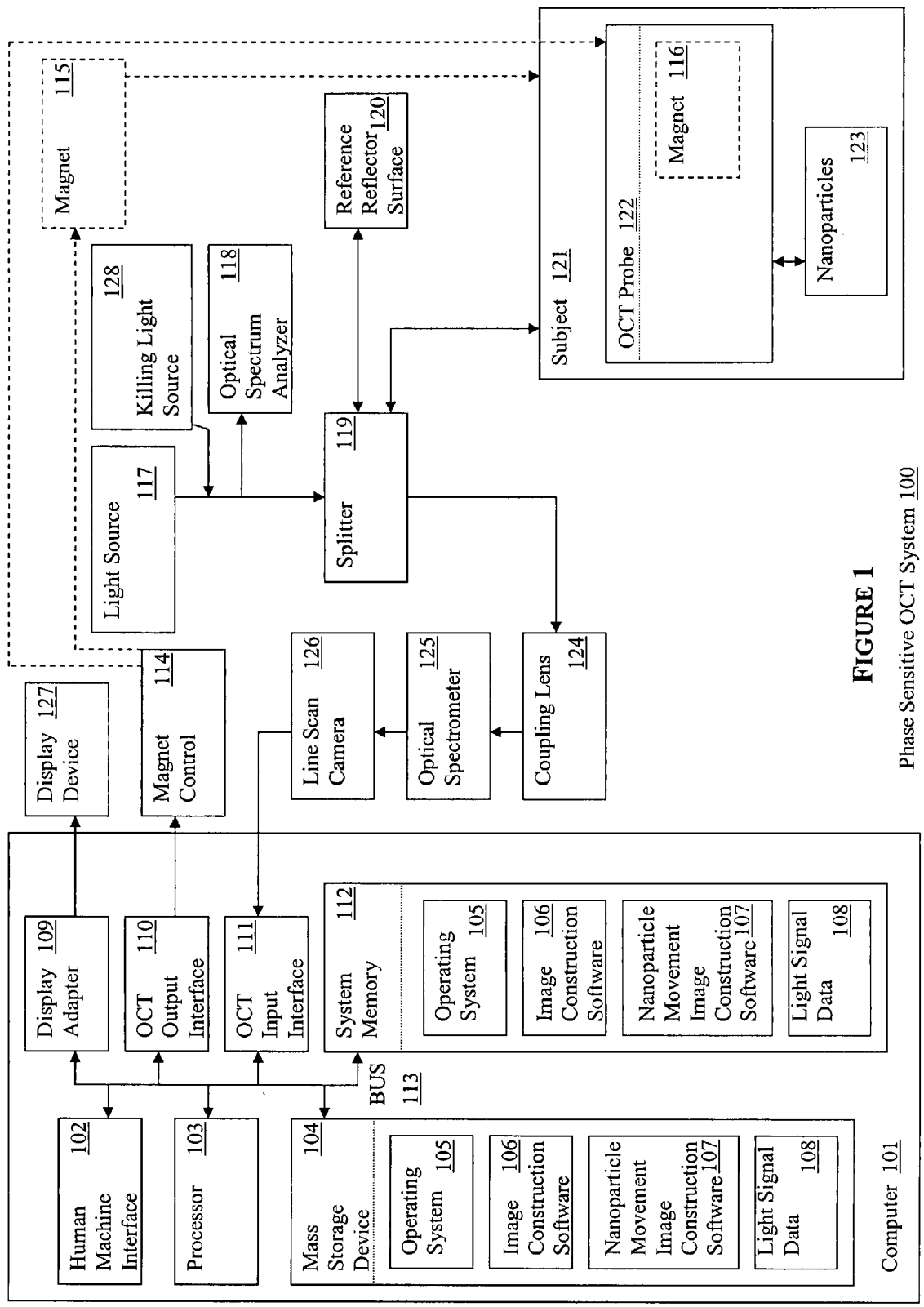
FIG. 1 is a block diagram illustrating an exemplary phase sensitive OCT system.

The methods, apparatuses, and systems can be understood more readily by reference to the following detailed description of the methods, apparatuses, and systems and the Examples included therein and to the Figures and their previous and following description.

Before the present compounds, compositions, articles, devices, and/or methods are disclosed and described, it is to be understood that these are not limited to specific synthetic methods, specific components, or to particular compositions, as such may, of course, vary. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Thus, for example, reference to "a nanoparticle" includes mixtures of nanoparticles, reference to "a nanoparticle" includes mixtures of two or more such nanoparticles, and the like.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not. For example, the phrase "optionally substituted shelled metals" means that shelled metals may or may not be substituted and that the description includes both unsubstituted shelled metals and shelled metals where there is substitution.

As used throughout, by a "subject" is meant an individual. Thus, the "subject" can include domesticated animals, such as cats, dogs, etc., livestock (e.g., cattle, horses, pigs, sheep, goats, etc.), laboratory animals (e.g., mouse, rabbit, rat, guinea pig, etc.) and birds. In one aspect, the subject is a mammal such as a primate or a human. The term does not denote a particular age or sex. Thus, adult and newborn subjects, as well as fetuses, whether male or female, are intended to be covered.

Reference will now be made in detail to exemplary aspects of the systems, methods, apparatuses, and/or compositions, examples of which are illustrated in the accompanying drawings.

Provided herein are methods, compositions and apparatuses for detecting a cell and/or a metallic composition using optical coherence tomography (OCT). By a "cell" is meant one or more cell of, or derived from, a living organism or subject. The cell or cells can be located within a subject or can be located ex vivo. The disclosed methods, compositions and apparatuses for detecting a cell and/or a metallic composition are described herein variously by reference to cell(s), composition(s) and/or metallic composition(s). It will be understood that description of various aspects of the disclosed methods, compositions and apparatuses by reference to one or a subset of cell(s), composition(s) or metallic composition(s) constitutes description of that aspect of the disclosed methods, compositions and apparatuses to the non-referenced cell(s), composition(s) and metallic composition(s), unless the context clearly indicates otherwise.

An exemplary method for detecting a cell comprises applying a magnetic field to the cell. A cell can comprise a cellular membrane and a metallic composition. Optionally, the metallic composition is a metallic nanoparticle that was administered to the subject or otherwise brought into contact with the cell. In another exemplary method for detecting a cell, light energy that can cause a change in the cell can be applied to the cell. For example a pulsed laser can be used to cause movement of a particle comprised by the cell, the cell, and/or tissues in proximity to the cell. Alternatively, sound energy can be used to cause change in the cell.

The metallic composition can be located within the cell, including in the cell's cellular membrane, or on the outside of the cell. If the metallic particle is located on the outside of the cell, it can be connected or targeted to the exterior surface of the cell's cellular membrane. Exemplary methods of targeting or connecting a metallic composition to a cell are described herein.

The applied magnetic field can interact with the metallic composition whether it is located within the cell or located external and connected to the cell. The interaction of the magnetic field with the composition can cause a change in the cell. Applied light energy that can cause a change in the cell can also be applied to the metallic composition. The interaction of the cell changing light energy with the composition or metallic particle of the cell can cause a change in the cell.

As used throughout, a "change" in a cell can be a "non-lethal change," and such terms are used interchangeably throughout except where the context dictates otherwise. A change "in" the cell is not limited to changes internal to the cell's cellular membrane. A change "in" the cell is inclusive of changes within the cell, and also includes any change to, of, or in the cell caused by the interaction of the magnetic field with the composition. For example, changes that can occur "in" the cell include movement of the cell, movement of the metallic composition, a change in the cellular membrane tension level of the cell, and a change in the internal strain field of the cell. Changes in the cell that cause changes, including those listed above, of neighboring or surrounding cells or tissues can also be detected. Thus, changes in a cell can cause changes in surrounding cells or tissues. The changes in the surrounding cells or tissues can be detected using the methods and systems described herein. Compositions located within or external to the cell can cause one or more detectable changes in the cell when contacted by an applied magnetic field.

A detectable internal strain field can be generated in a cell when a metallic composition, including a metallic nanoparticle, is under the action of an external force. The internal strain field can be detected using phase sensitive OCT using block correlation signal processing techniques that have been applied in elasticity imaging in ultrasound imaging. The external force may be provided by the application of an external magnetic flux density (B). Action of the external force on each metallic composition can produce movement of the metallic composition ($z_{np}(t)$) that produces a change in the cellular membrane tension level or an internal strain field within a cell. Action of a force on each metallic composition in a cell or tissues produces a movement of the metallic composition ($z_{np}(t)$). Movement of the metallic composition can be along the z-direction. The metallic composition can also have movement in any direction that can be written as vector displacement, $u_{np}(r_o)$ for a metallic composition positioned at $r_o$. Metallic composition displacement $u_{np}(r_o)$ can produce a displacement field ($u(r,r_o)$) in the proteins in the cell containing the metallic composition and surrounding cells. In the case of a homogeneous elastic media, the displacement field ($u(r,r_o)$) can be computed for a semi-infinite half-space following, for example, the method of Mindlin (R. D. Mindlin, A force at a point of a semi-infinite solid, Physics 1936, 7:195-202, which is incorporated by reference for the methods taught therein). In the case of an inhomogenous viscoelastic media, a finite element method numerical approach can be applied to compute the displacement field in the cell. The displacement field ($u(r,r_o)$) produced by a metallic composition positioned at $r_o$ can induce an internal stain field that is determined by change in the displacement field along a particular direction. The strain field ($\epsilon_{ij}(r,r_o)$) is a tensor quantity and is given by, $$\varepsilon_{ij}(r, r_o) = \frac{\partial u_i(r, r_o)}{\partial x_j}$$

where $u_i(r,r_o)$ is the i'th component of the displacement field and $x_j$ is the $j^{th}$ coordinate direction. For example, when j=3, $x_3$ is the z-direction. The internal strain field in a cell due to all metallic compositions in the cell and surrounding cells is a superposition of the strain fields due to each metallic composition. A detectable change in a cell can also be caused with light energy. For example, pulsed laser light can be applied to contact a metallic particle comprised by a cell including in a cell either naturally occurring or administered exogenously. The application of light energy can cause a detectable change in optical path due to a change in optical refractive and thermal elastic expansion. The light energy can also cause motion of the cell, particle, or tissues proximate to the cell for detection by optical coherence tomography. Such movement can be caused by thermal elastic expansion. Alternatively, sound energy can motion of the cell, particle, or tissues proximate to the cell for detection by optical coherence tomography.

The change in strain field surrounding the cell can be detected using phase-sensitive optical coherence tomographic imaging modalities. In this approach phase sensitive interference fringes can be detected before and immediately after the application of a force on the MONs nanoparticle. Utilizing block correlation algorithms for ultrasound elasticity imaging of spatially-resolved interference fringes recorded before and after application of a force on the MONs nanoparticle can be used for determination of the spatially resolved strain field surrounding the cell. Thus, the cell can be detected by detecting the change in the cell caused by the interaction of the magnetic field energy, or light energy, or sound energy causing a change in the cell with the metallic composition using such a modality. The spatially resolved strain field due to application of the external force can be detected using a phase sensitive optical coherence tomographic imaging modality. Non-limiting examples of phase sensitive optical coherence tomographic (OCT) imaging modalities are described herein. Phase sensitive OCT imaging modalities can comprise a probe for transmitting and receiving light energy to and from the cell. The light energy used for OCT imaging modalities can be distinct from the light energy used to cause a change in the cell as would be clear to one skilled in the art. Thus, the OCT modality can use light energy for detection of the cell that is typical of OCT imaging systems. The systems described herein can also be used with a light source for causing a change in the cell. OCT imaging light energy can therefore be distinguished from light energy or energy that causes a change in the cell or cell changing energy. The probe can be sized, shaped and otherwise configured for intravascular operation. The probe can further comprise a magnetic source for applying the magnetic field to the cell. The magnetic field can be applied to the cell from a magnetic source located external to the subject or internal to the subject. The external source can be located in a probe or can be distinct from a probe. The external force can also be the application of pulsed laser light that is selectively absorbed by the metallic composition of the cell and that generates a thermoelastic strain field surrounding the composition or particle. By recording images before or after pulsed laser exposure, the thermoelastic strain field in the tissue may be determined using block correlation algorithms applied for ultrasound elasticity and thermal imaging.

The metallic composition can comprise a plurality of metallic nanoparticles. The nanoparticles can be substantially spherical in shape and can have a diameter from about 0.1 nanometers (nm) to about 1000.0 nm. The nanoparticles are not, however, limited to being spherical in shape. Thus, the nanoparticles are asymmetrical in shape. If the nanoparticles are asymmetrical in shape, the largest cross sectional dimension of the nanoparticles can be from about 0.1 nanometers (nm) to about 1000.0 nm in length.

The metallic composition can comprise metal having non-zero magnetic susceptibility or zero magnetic susceptibility or combinations of non-zero and zero magnetic susceptibility metals. Thus, if the composition comprises nanoparticles, the nanoparticles can all have a non-zero magnetic susceptibility or a zero magnetic susceptibility or a combination of particles having a non-zero magnetic susceptibility and a zero magnetic susceptibility. Metallic compositions having a non-zero magnetic susceptibility can comprise a material selected from the group consisting of iron oxide, iron, cobalt, nickel, chromium and combinations thereof. The metallic compositions can comprise metal having non-zero electrical conductivity or zero electrical conductivity or combinations of non-zero and zero electrical conductivity metals. Also provided is a method for detecting a composition, the method wherein the composition comprises a magnetic or paramagnetic material. Any magnetic or paramagnetic material, whether metallic or non-metallic, can be used in the described methods or with the described systems. In this regard, any material can be used that can cause a change in a cell or can be detected using phase sensitive optical coherence tomography when contacted with an applied magnetic field. Similarly, non-metallic, non-magnetic particles can be used to cause a change in a cell or can be detected using phase sensitive optical coherence tomography when contacted with an applied magnetic field using the methods and systems described herein. Also, as described herein, a pulsed light source can be applied to a cell and a thermoelastic strain field can be detected with phase-sensitive OCT.

The systems, apparatuses and methods can be practiced using metallic compositions without magnetic susceptibility. When using metallic compositions without magnetic susceptibility, or when using compounds having a non-zero magnetic susceptibility, an electrical eddy current can be induced in the composition.

To induce an eddy current in a metallic composition a first time-varying magnetic field can be applied to a cell. The first magnetic field can interact with a metallic composition within or external to the cell to induce an electrical eddy current within the metallic composition. A second magnetic field can be applied to the cell that interacts with the induced eddy current to cause a change in the cell. The cell can be detected by detecting the change in the cell caused by the interaction of the second magnetic field with eddy current using a phase sensitive optical coherence tomographic imaging modality. Exemplary changes in the cell caused by the interaction of the second magnetic field with the eddy current include movement of the cell, movement of the metallic composition, a change in the cellular membrane tension level, and a change in the internal strain field of the cell.

Thus, a metallic composition or a nanoparticle that does not have a significant magnetic permeability can be used. For example, although gold nanoparticles do not have significant magnetic permeability many target-specific molecular agents (e.g., antibodies) can be conjugated to the nanoparticle surface. When using a high-conductivity particle for detection, a magnetic dipole can be induced in the particle by exposing to a time-varying magnetic field (B(t)).

The time-varying magnetic field (B(t)) can cause an electromotive force or potential in the particle that can induce a volumetric and surface electric eddy-current in the high-conductivity nanoparticle. Exemplary circuitry for a magnetic pulser that can be used to produce an eddy current is described in G H Schroder, Fast pulsed magnet systems, Handbook of Accelerator Physics and Engineering, A. Chao and M. Tinger, Eds. 1998 or in IEEE transactions on instrumentation and measurement, VOL. 54, NO. 6, December 2005, pp 2481-2485, which are incorporated herein by reference for the circuitry and methods described therein.

The eddy-current can produce time-varying magnetic moment that can interact with a second applied magnetic field ($B_2$). The induced eddy-current in the high-conductivity nanoparticle or metallic composition and the second applied magnetic field can interact to produce a torque or twist on the nanoparticle or metallic composition. The induced torque can twist the nanoparticle that is mechanically linked to a target in the cell (e.g., the membrane) or located inside the cell. The twisting motion of the nanoparticle can modify the internal strain field of the cell (surrounding cells and tissue) which can be detected using phase sensitive optical coherence tomography. In this approach, phase-sensitive data can be recorded before and after application of a first field to induce an eddy current and block correlation algorithms can be used to compute the depth resolved strain field in the tissue resulting from the motion of the nanoparticle or metallic composition.

In exemplary embodiments, large magnetic fields can be generated by low temperature superconducting magnets. These magnets need only be "charged" once, maintained at a low temperature and do not require an external current to maintain the magnetic field.

A metallic composition can be administered to the subject. Administration of exogenous metallic compositions, for example, metallic nanoparticles is described in greater detail below. Optionally, the cell can be located within a subject and the metallic composition can be administered to the subject. Optionally, the cell can be a macrophage and at least one metallic nanoparticle can be located within the macrophage or can be connected to the macrophage. The macrophage can be located in an atherosclerotic plaque within the subject. The macrophage can also be located within the eye of the subject.

The change in the cell caused by the interaction of the magnetic field with the metallic composition can be detected by generating a phase sensitive optical coherence tomographic image before or after application of the field. A phase sensitive optical coherence tomographic image can comprise one or more lines of phase sensitive light energy data captured using a phase sensitive optical coherence tomography modality, wherein at least one line is captured before, after, or during the application of the magnetic field.

One or more data line can be produced by generating light energy and transmitting at least a first portion of the generated light energy onto a reference reflector wherein at least a portion of the transmitted first portion of light energy is reflected by the reference reflector. At least a second portion of the generated light energy can be transmitted to contact the cell wherein at least a portion of the light energy that contacts the cell is reflected by the cell. The light energy reflected by the reference reflector and by the cell can be received, and the received light energy can be combined, and the received light energy can interfere. The combined light energy is processed to produce a phase sensitive optical coherence data line. One or more data lines can also be produced by generating light energy and transmitting at least a first portion of the generated light energy onto a reference reflector wherein at least a portion of the transmitted first portion of light energy is reflected by the reference reflector. At least a second portion of the generated light energy can be transmitted to contact the metallic composition wherein at least a portion of the light energy that contacts the metallic composition is reflected by the composition. The light energy reflected by the reference reflector and by the composition can be received. The received light energy can be combined, wherein the received light energy interferes. The combined light energy can be processed to produce the phase sensitive optical coherence data line. The phase sensitive A-lines can be recorded before or after application of the stimulating field (magnetic, eddy-current, generation of pulsed light energy). Thus, the methods can further comprise recording reference phase sensitive interference fringe data prior to the non-lethal change and second phase sensitive interference fringe data during or after non-lethal change. The reference and second data can be correlated to quantify the non-lethal change.

Phase sensitive light energy data lines can include the spectral dependent complex amplitude of light reflected from the cell, $A_c(v)$, where $v$ is the optical frequency of light. More precisely, what can be measured is product of the amplitudes of light reflected from the cell and reference: $A_c(v) \cdot A_r(v)^*$ where $A_r(v)^*$ is the conjugate of the spectrally-dependent complex amplitude of light reflected from the reference. The quantity $A_c(v) \cdot A_r(v)^*$ can be used to determine $A_c(\tau)$ the phase sensitive amplitude of light backreflected from the cell/tissue at different time-delays $\tau$ by using a time-frequency transformation (e.g., Fourier).

A plurality of phase sensitive light energy data lines can be captured before and after application of the stimulating field and used to construct an image. A phase sensitive image produced using the described systems and methods can have a phase sensitive resolution of at least about 30.0 nanometers (nm), 25.0 nm, 15.0 nm, 10.0 nm, 5.0 nm, 4.0 nm, 3.0 nm, or 2.0 nm. A plurality of phase sensitive light energy data lines can be spatially and temporally distinct and the image can comprise a B-mode image frame of at least two of the data lines. The plurality of phase sensitive light energy data lines can also be temporally distinct and the image can comprise an M-mode image comprising at least two of the lines.

When a plurality of lines are used to create an image, at least a first phase sensitive light energy data line can be captured prior to the application of the magnetic field and at least a second phase sensitive light energy data line can be captured during or after application of the magnetic field. The magnetic field strength can be altered between the capture of data lines or between the capture of images. For example, at least a first phase sensitive light energy data line can be captured during the application of the magnetic field, wherein the magnetic field has a first predetermined strength and at least a second phase sensitive light energy data line during application of a second magnetic field having a second predetermined strength. The captured lines can be processed to create an image. For example the capture lines can be processed using block correlation algorithms to create an image of the strain field produced due to the increased field strength. Optionally, the first predetermined strength can be less than the second predetermined strength.

The described methods allows for the construction of both conventional intensity based OCT B-scan images and phase sensitive B-scan images or by using block correlation algorithms the change in strain field due to changing field. The phase sensitive B-scan images for viewing can correspond to changes in phase formed by at least two phase sensitive B-scan images corresponding to different magnetic field strengths (one of which can be zero magnetic field strength). At least two types of images can be viewed—one, a conventional intensity based OCT B-scan image and second a phase sensitive B-scan image formed by the difference of two phase sensitive images recorded at different magnetic field strengths. Moreover, these two images (conventional intensity based OCT B-scan image and strain field image) can be superimposed to form a hybrid image showing the magnitude and direction of strain produced by the external field.

Also provided are methods for detecting a composition comprising metal by applying a magnetic field to the composition, wherein the magnetic field interacts with the composition. The metallic composition can be detected using a phase sensitive optical coherence tomographic imaging modality. As described throughout, the composition can be located in a cell or can be connected to a cell. The composition can also be located in connection with non-cellular biological matter. For example, non-cellular biological matter can include a protein, a lipid, a peptide, and a nucleic acid.

The methods of detecting cells and compositions using optical coherence tomography can comprise administering a plurality of metallic nanoparticles to a subject.

Optionally, at least one administered nanoparticle localizes within a macrophage located in the subject. At least one administered nanoparticle can also be optionally configured to localize to a target site in the subject.

In the methods described herein, a nanoparticle comprising a material with non-zero magnetic susceptibility can be positionally moved in vivo or in vitro by an applied magnetic field. A material of non-zero magnetic susceptibility can include a variety of materials. For example, the nanoparticle can comprise any physiologically tolerable magnetic material or combinations thereof. The term magnetic material can optionally include any material displaying ferromagnetic, paramagnetic or superparamagnetic properties. For example, the nanoparticles can comprise a material selected from the group consisting of iron oxide, iron, cobalt, nickel, and chromium. Metallic compositions as described throughout, including administered nanoparticles, can be magnetic. Optionally, a nanoparticle comprises iron oxide. When a nanoparticle comprises metal or magnetic materials, it can be moved while in the subject using an internally or externally applied magnetic field, as described below. Any relevant metal with non-zero magnetic susceptibility or combinations thereof can be used. Many useable metals are known in the art; however, any metal displaying the desired characteristics can be used. Nanoparticles can also comprise a combination of a material with a non-zero magnetic susceptibility and a material with a lower or zero magnetic susceptibility. For example, gold can be combined with higher magnetic susceptibility materials (e.g., iron). For example, gold coated iron can be used. Nanoparticles can also comprise polymers or other coating materials alone or in combination. Such polymers or coating materials can be used to attach targeting ligands, including but not limited to antibodies, as described below. When used in vivo, an administered nanoparticle can be physiologically tolerated by the subject, which can be readily determined by one skilled in the art.

Nanoparticles can be solid, hollow or partially hollow and can be spherical or asymmetrical in shape. Optionally, the cross section of an asymmetric nanoparticle is. oval or elliptical. As one of skill in the art will appreciate, however, other asymmetric shapes can be used. In one example, the particle can be shaped like a bacterium. A bacterium shaped particle can be used to increase the likelihood of engulfinent of the particle by a macrophage. The nanoparticles can comprise shelled or multi-shelled nanoparticles. Each shell layer can be metal. A multi-shelled particle can also have one or more layers that are non-metallic. For example, the particles can be coated with sugar, polysaccharide, protein, peptide, polypeptide, amino acid, nucleic acid, and portions or fragments of each of these coating compositions. Moreover, each coating composition or portion thereof, or metal composition can fully or partially surround any other portion of a particle.

One exemplary particle comprises iron oxide and gold. The iron oxide can form a core that is surrounded partially or fully by a gold layer. Dextran can be applied to the gold layer to comprise a particle of iron, gold and dextran. Other exemplary layers can also be used. For example, a metallic core can selected based on its magnetic properties so that it can be moved in the subject by an applied magnetic force. A second metal layer can be selected based on that layer can modify the light absorption properties of the particle and the light absorptive characteristics of the tissue or media where the particle is located. For example, gold particles or shells can be used to absorb near infrared light. Exemplary combinations of materials for particles that can be moved by an applied magnetic force and can absorb light more than proximate tissue or cells of the subject can be selected using the principles of photothermolysis known in the art and described below.

Figure 12:
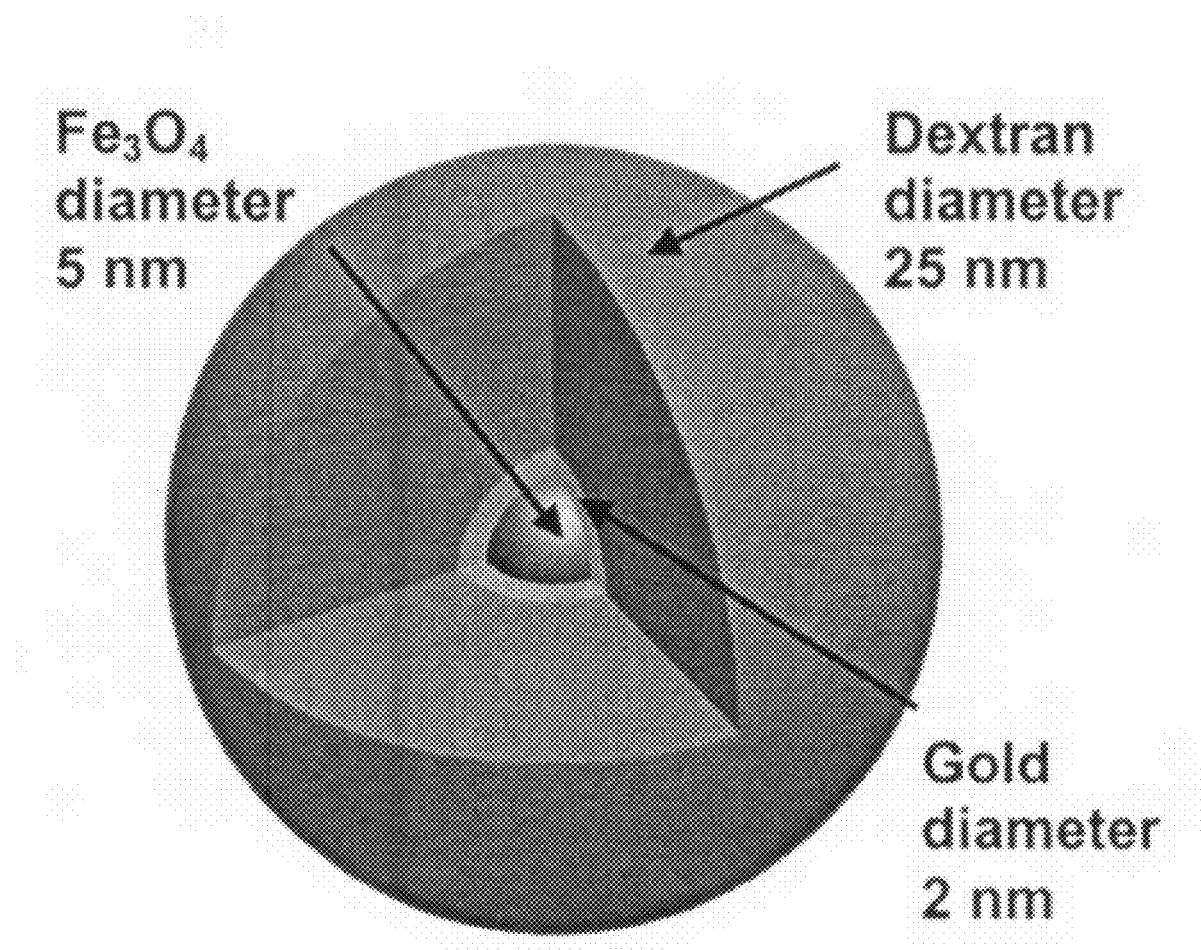
FIG. 12 is a schematic diagram showing exemplary multifunctional OCT nanoparticles (MONs) with an iron core for magnetic properties, a gold coating to tune wavelength absorption to 700 nm (above competing plaque components such as hemoglobin), and absorbed aminodextran coating for selective macrophage uptake.
Figure 13A:
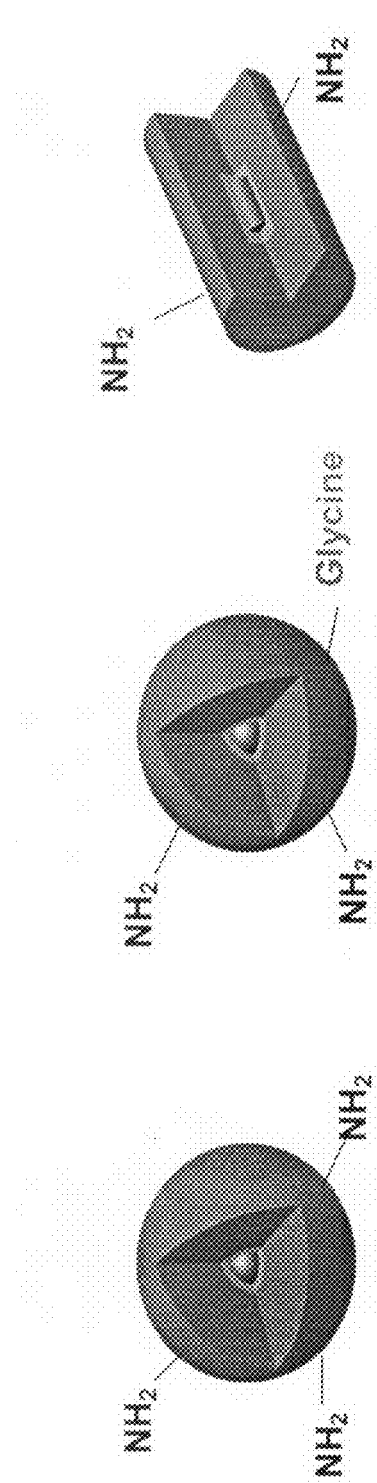
FIG. 13A is a schematic diagram showing exemplary multifunctional OCT nanoparticles (MONs) with an aminodextran outer shell adsorbed on an inner gold shell (see FIG. 13B for chemistry of attachment). Additional $NH_2$ sites on the dextran that are not bound to gold can be used to conjugate small molecules such as Glycine to raise the selectivity for macrophage uptake. Particle shape can also be altered to mimic the rod-like appearance of bacteria to enhance macrophage uptake.

Exemplary nanoparticles are shown in FIGS. 12 and 13. FIG. 12 is a schematic diagram showing exemplary multifunctional OCT nanoparticle with an iron core for magnetic properties, a gold coating to tune wavelength absorption to 700 nm (above competing plaque components), and an adsorbed aminodextran coating for enhanced selective macrophage uptake.

Figure 13B:
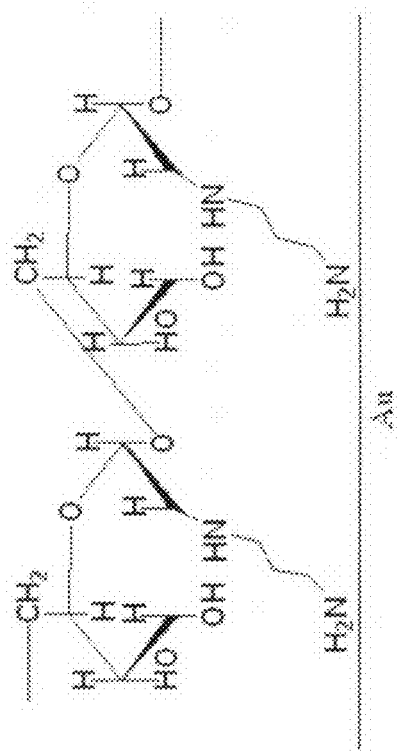

FIG. 13 is a schematic diagram showing exemplary multifunctional OCT nanoparticles (MONs) with an aminodextran outer shell adsorbed on an inner gold shell (see FIG. 13B for chemistry of attachment). Additional NH2 sites on the dextran that are not bound to gold can be used to conjugate small molecules such as Glycine to raise the selectivity for macrophage uptake. Particle shape can also be altered to mimic the rod-like appearance of bacteria to enhance macrophage uptake.

Shelled or multi-shelled nanoparticles can have targeting ligands conjugated to the shell material wherein the targeting ligand has an affinity for or binds to a target site in a subject or ex vivo. Such shelled or multi-shelled nanoparticles can be made, for example, using techniques known in the art, for example, as described in Loo et al., "Nanoshell-Enabled Photonics-Based Imaging and Therapy of Cancer," Tech. Cancer Res. and Treatment, (2004) 3(1) 33-40, which is incorporated herein by reference for the methods taught herein. Further, Oldenburg et al., "Nanoengineering of Optical Resonances," Chemical Physics Letters (1998) 288, 243-247, is incorporated herein for methods of nanoshell synthesis.

A metallic composition, including a nanoparticle, can be configured to localize to a target site within the subject. For example, the metallic composition can be configured to localize to a neoplastic cell, to a peptide, to a protein, or to a nucleic acid. Optionally, the target site is an extracellular domain of a protein. A variety of cell types can also be targets of the metallic compositions. For example, target cells can be selected from one or more of a neoplastic cell, a squameous cell, a transitional cell, a basal cell, a muscle cell, an epithelial cell, and a mucosal cell. The target cells can also be located at different anatomical locations within a subject. For example, the cell can be located in the subject at an anatomical location selected from the group consisting of a lung, bronchus, intestine, stomach, colon, eye, heart, blood vessel, cervix, bladder, urethra, skin, muscle, liver, kidney, and blood.

One or more administered nanoparticle can localize to a desired target within the subject using passive or active targeting mechanisms. Passive targeting mechanisms take advantage of the subject's inherent defense mechanisms to highlight phagocytic cells naturally responsible for particle clearance. For example, macrophage rich areas are a pathological correlate to an unstable atherosclerotic plaque in a subject. Moreover, administered nanoparticles, for example, small superparamagnetic and ultrasmall superparamagnetic particles of iron oxide, are avidly taken up, or engulfed by, macrophages located in unstable plaques. Thus, through the subject's natural defense mechanism, wherein macrophages accumulate in an unstable atherosclerotic plaque and engulf administered nanoparticles, administered nanoparticles can passively target the unstable plaque. Similarly, macrophages located in the eye of a subject can engulf nanoparticles. Such passive targeting of nanoparticles can be used with the methods and apparatuses described herein to highlight a plaque's instability or to highlight other accumulation of phagocytic cells.

Active targeting mechanisms can refer to the use of ligand-directed, site-specific targeting of nanoparticles. A nanoparticle can be configured to localize to a desired target site in a subject using a wide variety of targeting ligands including, but not limited to, antibodies, polypeptides, peptides, nucleic acids, and polysaccharides. Such nanoparticles are referred to herein as "targeted nanoparticles." Targeting ligands or fragments thereof can be used to target a nanoparticle to cellular, or other endogenous or exogenous biomarkers in the subject. Such a biomarkers or "target sites" can include, but are not limited to, proteins, polypeptides, peptides, polysaccharides, lipids, or antigenic portions thereof, which are expressed within the subject. When active targeting mechanisms are used to target a cell, the targeted nanoparticle can be optionally internalized by the targeted cell.

Thus, using the disclosed methods, at least one administered nanoparticle can optionally localize within a macrophage located in the subject and/or at least one administered targeted nanoparticle can localize to a desired target site in the subject.

The methods and apparatuses are not, however, limited to in vivo administration to a subject. As would be clear to one skilled in the art, nanoparticles, including targeted nanoparticles, can be administered in vitro to an ex vivo sample with localization of the nanoparticle to a desired target site and subsequent imaging occurring in vitro. Moreover, a composition, including at least one nanoparticle can be administered to a subject in vivo, and a sample can be subsequently taken from the subject and imaged ex vivo using the methods, systems, and apparatuses described herein.

When using a targeted nanoparticle the target site in vivo or in vitro can be endogenous or exogenous. The target site can be selected from the group consisting of an organ, cell, cell type, blood vessel, thrombus, fibrin and infective agent antigens or portions thereof. Optionally, the target site can be a neoplastic cell. The target site can also be an extracellular domain of a protein. Furthermore, the target site can be selected from the group consisting of a lung, bronchus, intestine, stomach, colon, heart, brain, blood vessel, cervix, bladder, urethra, skin, muscle, liver, kidney and blood. The target site can also be a cell. For example, a cell can be selected from the group consisting of, but not limited to, a neoplastic cell, a squameous cell, a transitional cell, a basal cell, a muscle cell, an epithelial cell, a lymphocyte, a leukocyte, a monocyte, a red blood cell, and a mucosal cell.

Thus, targeted nanoparticles can be targeted to a variety of cells, cell types, antigens (endogenous and exogenous), epitopes, cellular membrane proteins, organs, markers, tumor markers, angiogenesis markers, blood vessels, thrombus, fibrin, and infective agents. For example, targeted nanoparticles can be produced that localize to targets expressed in a subject. Optionally, the target can be a protein, and can be a protein with an extracellular or transmembrane domain. Optionally, the target can be the extracellular domain of a protein.

Desired targets can be based on, but not limited to, the molecular signature of various pathologies, organs and/or cells. For example, adhesion molecules such as integrin $\alpha v\beta 3$, intercellular adhesion molecule-1 (I-CAM-1), fibrinogen receptor GPIIb/IIIa and VEGF receptors are expressed in regions of angiogenesis, inflammation or thrombus. These molecular signatures can be used to localize nanoparticles through the use of a targeting ligand. The methods described herein optionally use nanoparticles targeted to one or more of VEGFR2, I-CAM-1, $\alpha v\beta 3$ integrin, $\alpha v$ integrin, fibrinogen receptor GPIIb/IIIa, P-selectin, and/or mucosal vascular adressin cell adhesion molecule-1.

As used in this invention, the term "epitope" is meant to include any determinant capable of specific interaction with a targeting ligand as described below. Epitopic determinants can consist of chemically active surface groupings of molecules such as amino acids or sugar side chains and can have specific three dimensional structural characteristics, as well as specific charge characteristics.

Targeting ligands specific for a molecule that is expressed or over-expressed in a cell, tissue, or organ targeted for imaging, such as pre-cancerous, cancerous, neoplastic, or hyperproliferative cells, tissues, or organs, can be used with the nanoparticles described herein. This use can include the in vivo or in vitro imaging, detection, or diagnosis of pre-cancerous, cancerous, neoplastic or hyperproliferative cells in a tissue or organ. The compositions and methods of the invention can be used or provided in diagnostic kits for use in detecting and diagnosing cancer.

As used herein, a targeted cancer to be imaged, detected or diagnosed can be selected from, but are not limited to, the group comprising lymphomas (Hodgkins and non-Hodgkins), B cell lymphoma, T cell lymphoma, myeloid leukemia, leukemias, mycosis fungoides, carcinomas, carcinomas of solid tissues, squamous cell carcinomas, adenocarcinomas, sarcomas, gliomas, blastomas, neuroblastomas, plasmacytomas, histiocytomas, melanomas, adenomas, hypoxic tumors, myelomas, AIDS-related lymphomas or sarcomas, metastatic cancers, bladder cancer, brain cancer, nervous system cancer, squamous cell carcinoma of head and neck, neuroblastoma/glioblastoma, ovarian cancer, skin cancer, liver cancer, melanoma, squamous cell carcinomas of the mouth, throat, larynx, and lung, colon cancer, cervical cancer, cervical carcinoma, breast cancer, epithelial cancer, renal cancer, genitourinary cancer, pulmonary cancer, esophageal carcinoma, head and neck carcinoma, hematopoietic cancers, testicular cancer, colo-rectal cancers, prostatic cancer, or pancreatic cancer.

Pre-cancerous conditions to be imaged, detected or diagnosed include, but are not limited to, cervical and anal dysplasias, other dysplasias, severe dysplasias, hyperplasias, atypical hyperplasias, and neoplasias. As would be clear to one skilled in the art, however, additional cancers and pre-cancerous conditions can be imaged, detected or diagnosed using the methods and apparatuses described herein.

Using methods known in the art, and as described herein, targeting ligands, such as polyclonal or monoclonal antibodies, can be produced to desired target sites in a subject. Thus, a targeted nanoparticle can further comprise an antibody or a fragment thereof. Methods for preparing and characterizing antibodies are well known in the art (See, e.g., Antibodies: A Laboratory Manual, Cold Spring Harbor Laboratory, 1988; incorporated herein by reference for the methods taught therein).

Monoclonal antibodies can be obtained from a population of substantially homogeneous antibodies, i.e., the individual antibodies comprising the population are identical except for possible naturally-occurring mutations that can be present in minor amounts. Thus, the modifier "monoclonal" indicates the character of the antibody as not being a mixture of discrete antibodies.

For example, the monoclonal antibodies of the invention can be made using the hybridoma method first described by Kohler & Milstein, Nature 256:495 (1975), or can be made by recombinant DNA methods (Cabilly, et al., U.S. Pat. No. 4,816,567).

In the hybridoma method, a mouse or other appropriate host animal, such as hamster can be immunized to elicit lymphocytes that produce or are capable of producing antibodies that will specifically bind to the antigen used for immunization. Alternatively, lymphocytes can be immunized in vitro. Lymphocytes can be then fused with myeloma cells using a suitable fusing agent, such as polyethylene glycol, to form a hybridoma cell (Goding, Monoclonal Antibodies: Principles and Practice, pp. 59-103 (Academic Press, 1986)).

DNA encoding a monoclonal antibody can be readily isolated and sequenced using conventional procedures (e.g., by using oligonucleotide probes that are capable of binding specifically to genes encoding the heavy and light chains of murine antibodies). The hybridoma cells can serve as a preferred source of such DNA. Once isolated, the DNA can be placed into expression vectors, which can then be transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also can be modified, for example, by substituting the coding sequence for human heavy and light chain constant domains in place of the homologous murine sequences, Morrison, et al., Proc. Nat. Acad. Sci. 81, 6851 (1984), or by covalently joining to the immunoglobulin coding sequence all or part of the coding sequence for a non-immunoglobulin polypeptide. In that manner, "chimeric" or "hybrid" antibodies can be prepared that have the binding specificity of an anti-cancer, pre-cancer, or hyperproliferative cell or other target molecule. Optionally, the antibody used herein is "humanized" or fully human.

Non-immunoglobulin polypeptides can be substituted for the constant domains of an antibody of the invention, or they can be substituted for the variable domains of one antigen-combining site of an antibody of the invention to create a chimeric bivalent antibody comprising one antigen-combining site having specificity for a first antigen and another antigen-combining site having specificity for a different antigen.

Chimeric or hybrid antibodies also can be prepared in vitro using known methods in synthetic protein chemistry, including those involving crosslinking agents.

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., Nature 321, 522-525 (1986); Riechmann et al., Nature 332, 323-327 (1988); Verhoeyen et al., Science 239, 1534-1536 (1988)), by substituting rodent CDRs or CDR sequences for the corresponding sequences of a human antibody. Accordingly, such "humanized" antibodies are chimeric antibodies, wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Antibodies can be humanized with retention of high affinity for the target site antigen and other favorable biological properties. Humanized antibodies can be prepared by a process of analysis of the parental sequences and various conceptual humanized products using three dimensional models of the parental and humanized sequences. Three dimensional immunoglobulin models-are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e. the analysis of residues that influence the ability of the candidate immunoglobulin to bind its antigen. In this way, FR residues can be selected and combined from the consensus and import sequence so that the desired antibody characteristic, such as increased affinity for the target site antigen(s), can be achieved. In general, the CDR residues are directly and most substantially involved in influencing antigen binding.

Human monoclonal antibodies can be made by a hybridoma method. Human myeloma and mouse-human heteromyeloma cell lines for the production of human monoclonal antibodies have been described, for example, by Kozbor, J. Immunol. 133, 3001 (1984), and Brodeur, et al., Monoclonal Antibody Production Techniques and Applications, pp. 51-63 (Marcel Dekker, Inc., New York, 1987).

Transgenic animals (e.g., mice) can be used that are capable, upon immunization, of producing a repertoire of human antibodies in the absence of endogenous immunoglobulin production. For example, it has been described that the homozygous deletion of the antibody heavy chain joining region (JH) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g. Jakobovits et al., Proc. Natl. Acad. Sci. USA 90, 2551-255 (1993); Jakobovits et al., Nature 362, 255-258 (1993).

Alternatively, phage display technology (McCafferty et al., Nature 348, 552-553 (1990)) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats; for their review see, e.g. Johnson, Kevin S. and Chiswell, David J., Current Opinion in Structural Biology 3, 564-571 (1993). Several sources of V-gene segments can be used for phage display. Clackson et al., Nature 352, 624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., J. Mol. Biol. 222, 581-597 (1991), or Griffith et al., EMBO J. 12, 725-734 (1993). In a natural immune response, antibody genes accumulate mutations at a high rate (somatic hypermutation). Some of the changes introduced can confer higher affinity, and B cells displaying high-affinity surface immunoglobulin are preferentially replicated and differentiated during subsequent antigen challenge. This natural process can be mimicked by employing the technique known as "chain shuffling" (Marks et al., Bio/Technol. 10, 779-783 (1992)). In this method, the affinity of "primary" human antibodies obtained by phage display can be improved by sequentially replacing the heavy and light chain V region genes with repertoires of naturally occurring variants (repertoires) of V domain genes obtained from unimmunized donors. This technique allows the production of antibodies and antibody fragments with affinities in the nM range. A strategy for making very large phage antibody repertoires (also known as "the mother-of-all libraries") has been described by Waterhouse et al., Nucl. Acids Res. 21, 2265-2266 (1993), and the isolation of a high affinity human antibody directly from such large phage library is reported by Griffith et al., EMBO J. (1994). Gene shuffling can also be used to derive human antibodies from rodent antibodies, where the human antibody has similar affinities and specificities to the starting rodent antibody. According to this method, which is also referred to as "epitope imprinting," the heavy or light chain V domain gene of rodent antibodies obtained by phage display technique is replaced with a repertoire of human V domain genes, creating rodent-human chimeras. Selection on antigen results in isolation of human variable capable of restoring a functional antigen-binding site, i.e. the epitope governs (imprints) the choice of partner. When the process is repeated in order to replace the remaining rodent V domain, a human antibody is obtained (see PCT patent application WO 93/06213, published Apr. 1, 1993). Unlike traditional humanization of rodent antibodies by CDR grafting, this technique provides completely human antibodies, which have no framework or CDR residues of rodent origin.

Bispecific antibodies are monoclonal, preferably human or humanized, antibodies that have binding specificities for at least two different antigens. One of the binding specificities is for a first antigen and the other one is for a second antigen.

Traditionally, the recombinant production of bispecific antibodies is based on the coexpression of two immunoglobulin heavy chain-light chain pairs, where the two heavy chains have different specificities (Millstein and Cuello, Nature 305, 537-539 (1983)). Because of the random assortment of immunoglobulin heavy and light chains, these hybridomas (quadromas) produce a potential mixture of 10 different antibody molecules, of which only one has the correct bispecific structure. The purification of the correct molecule, which is usually done by affinity chromatography steps, is rather cumbersome, and the product yields are low. Similar procedures are disclosed in PCT application publication No. WO 93/08829 (published May 13, 1993), and in Traunecker et al., EMBO 10, 3655-3659 (1991). For further details of generating bispecific antibodies see, for example, Suresh et al., Methods in Enzymology 121, 210 (1986).

Heteroconjugate antibodies are also within the scope of the described compositions and methods. Heteroconjugate antibodies are composed of two covalently joined antibodies. Heteroconjugate antibodies can be made using any convenient cross-linking methods. Suitable cross-linking agents are well known in the art, and are disclosed in U.S. Pat. No. 4,676,980, along with a number of cross-linking techniques.

A variety of immunoassay formats can be used to select antibodies that selectively bind with a desired target site or target site antigen. For example, solid-phase ELISA immunoassays are routinely used to select antibodies selectively immunoreactive with a protein, protein variant, or fragment thereof. See Harlow and Lane. Antibodies, A Laboratory Manual. Cold Spring Harbor Publications, New York, (1988), for a description of immunoassay formats and conditions that could be used to determine selective binding. The binding affinity of a monoclonal antibody can, for example, be determined by the Scatchard analysis of Munson et al., Anal. Biochem., 107:220 (1980).

Not only can a targeted nanoparticle comprise an antibody or fragment thereof, but a targeted nanoparticle can also comprise targeting ligand that is a polypeptide or a fragment thereof. Optionally, polypeptides that are internalized by target cells can be attached to the surface of a nanoparticle. Ligands that are internalized can optionally be used for internalization of a nanoparticle into a target cell. A modified phage library can be use to screen for specific polypeptide sequences that are internalized by desired target cells. For example, using the methods described in Kelly et al., "Detection of Vascular Adhesion Molecule-1 Expression Using a Novel Multimodal Nanoparticle," Circulation Res., (2005) 96:327-336, which is incorporated herein for the methods taught therein, polypeptides can be selected that are internalized by VCAM-1 expressing cells or other cells expressing a ligand of interest.

There are a number of methods for isolating proteins which can bind a desired target. For example, phage display libraries have been used to isolate numerous polypeptides that interact with a specific target. (See for example, U.S. Pat. Nos. 6,031,071; 5,824,520; 5,596,079; and 5,565,332 which are herein incorporated by reference at least for their material related to phage display and methods related to combinatorial chemistry). Thus targeted nanoparticles can comprise a polypeptide or fragments thereof that interact with a desired target. A targeted nanoparticle can also comprise a binding domain of an antibody or phage.

The term "polypeptide" or "peptide" is used broadly herein to mean two or more amino acids linked by a peptide bond. The term "fragment" or "proteolytic fragment" also is used herein to refer to a product that can be produced by a proteolytic reaction on a polypeptide, i.e., a peptide produced upon cleavage of a peptide bond in the polypeptide. A fragment can be produced by a proteolytic reaction, but it should be recognized that a fragment need not necessarily be produced by a proteolytic reaction but can be produced using methods of chemical synthesis or methods of recombinant DNA technology, to produce a synthetic peptide that is equivalent to a proteolytic fragment. It should be recognized that the term "polypeptide" is not used herein to suggest a particular size or number of amino acids comprising the molecule, and that a polypeptide of the invention can contain up to several amino acid residues or more.

A nanoparticle can bind selectively or specifically to a desired target site, and/or can be internalized by a target cell. Such selective or specific binding and/or internalization can be readily determined using the methods, systems and apparatuses described herein. For example, selective or specific binding can be determined in vivo or in vitro by administering a targeted nanoparticle and detecting an increase in light scattering from the nanoparticle bound to a desired target site or internalized into the desired target cell. Detection of light scattering can be measured using the systems and apparatuses described below.

Thus, a targeted nanoparticle can be compared to a control nanoparticle having all the components of the targeted nanoparticle except the targeting characteristics, such as, for example, targeting ligand. By detecting phase sensitive image data from the targeted nanoparticle bound to a desired target site versus a control nanoparticle, the specificity or selectivity of binding or internalization can be determined. If an antibody, polypeptide, or fragment thereof, or other targeting ligand is used, selective or specific binding to a target can be determined based on standard antigen/polypeptide/epitope/antibody complementary binding relationships. Further, other controls can be used. For example, the specific or selective targeting of the nanoparticles can be determined by exposing targeted nanoparticles to a control tissue, which includes all the components of the test or subject tissue except for the desired target ligand or epitope. To compare a control sample to a test sample, levels of light scattering can be detected by, for example, the systems described below and the difference in levels or location can be compared.

A targeting ligand can be coupled to the surface or shell of at least one of the nanoparticle. Targeted nanoparticles comprising targeting ligands can be produced by methods known in the art. For example ligands, including but not limited to, antibodies, peptides, polypeptides, or fragments thereof can be conjugated to the nanoparticle surface.

Any method known in the art for conjugating a targeting ligand to a nanoparticle can be employed, including, for example, those methods described by Hunter, et al., Nature 144:945 (1962); David, et al., Biochemistry 13:1014 (1974); Pain, et al., J. Immunol. Meth. 40:219 (1981); and Nygren, J. Histochem. and Cytochem. 30:407 (1982). Established protocols have been developed for the labeling metallic nanoparticles with a broad range of biomolecules, including protein A, avidin, streptavidin, glucose oxidase, horseradish peroxidase, and IgG (antibodies). Nanoparticles can be prepared with bioorganic molecules on their surface (DNA, antibodies, avidin, phospholipids, etc). The nanoparticles can be characterized, modified, and conjugated with organic and biomolecules. Polymers or other intermediate molecules can be used to tether antibodies or other targeting ligands to the surface of nanoparticles. Methods of tethering ligands to nanoparticles are know in the art as described in, for example, Loo et al., "Nanoshell-Enabled Photonics-Based Imaging and Therapy of Cancer," Tech. Cancer Res. and Treatment, (2004) 3(1) 33-40, which is incorporated herein by reference for the methods taught herein.

Covalent binding of a targeting ligand to a nanoparticle can be achieved, for example, by direct condensation of existing side chains or by the incorporation of external bridging molecules. Many bivalent or polyvalent agents can be useful in coupling polypeptide molecules to other particles, nanoparticles, proteins, peptides or amine functions. Examples of coupling agents are carbodiimides, diisocyanates, glutaraldehyde, diazobenzenes, and hexamethylene diamines. This list is not intended to be exhaustive of the various coupling agents known in the art but, rather, is exemplary of the more common coupling agents that can be used.

Optionally, one can first derivatize an antibody if used, and then attach the nanoparticle to the derivatized product. As used herein, the term "derivatize" is used to describe the chemical modification of the antibody substrate with a suitable cross-linking agent. Examples of cross-linking agents for use in this manner include the disulfide-bond containing linkers SPDP (N-succinimidyl-3-(2-pyridyldithio)propionate) and SMPT (4-succinimidyl-oxycarbonyl-α-methyl-α(2-pyridyldithio)toluene).

Targeting ligands can also be conjugated to nanoparticles using methods including the preparation of biotinylated antibody molecules and their consequent interaction with streptavidin/nanoparticle conjugates. This approach takes advantage of strong biospecific interaction between biotin and streptavidin and known protocols for immobilization of streptavidin on nanoparticles. Polypeptides with thiol terminated alkyl chains can be directly attached to the surface of nanoparticles using the procedures described in Elghanian, R., et al., Selective colorimetric detection of polynucleotides based on the distance-dependent optical properties of gold nanoparticles. Science, 1997. 277(5329): p. 1078-1080 (incorporated by reference for the methods taught therein). For conjugation procedure one can use a mixture of thiol terminated polypeptides and relatively small mercaptoacetic molecules to avoid high density immobilization of the polypeptides.

Targeted nanoparticles can be prepared with a biotinylated surface and an avidinated antibody, peptide, polypeptide or fragment thereof can be attached to the nanoparticle surface using avidin-biotin bridging chemistry. Avidinated nanoparticles can be used and a biotinylated antibody or fragment thereof or another biotinylated targeting ligand or fragments thereof can be administered to a subject. For example, a biotinylated targeting ligand such as an antibody, protein or other bioconjugate can be used. Thus, a biotinylated antibody, targeting ligand or molecule, or fragment thereof can bind to a desired target within a subject. Once bound to the desired target, the nanoparticle with an avidinated surface can bind to the biotinylated antibody, targeting molecule, or fragment thereof. When bound in this way, light energy can be transmitted to the bound nanoparticle, which can produce light scattering of the transmitted light. An avidinated nanoparticle can also be bound to a biotinylated antibody, targeting ligand or molecule, or fragment thereof prior to administration to the subject.

When using a targeted nanoparticle with a biotinylated surface or an avidinated surface a targeting ligand can be administered to the subject. For example, a biotinylated targeting ligand such as an antibody, polypeptide or other bioconjugate, or fragment thereof, can be administered to a subject and allowed to accumulate at a target site When a targeted nanoparticle with a biotinylated surface is used, an avidin linker molecule, which attaches to the biotinylated targeting ligand can be administered to the subject. Then, a targeted nanoparticle with a biotinylated shell can be administered to the subject. The targeted nanoparticle binds to the avidin linker molecule, which is bound to the biotinylated targeting ligand, which is itself bound to the desired target. In this way, a three step method can be used to target nanoparticles to a desired target. The targeting ligand can bind to all of the desired targets detailed above as would be clear to one skilled in the art.

Nanoparticles, including targeted nanoparticles, can also comprise a variety of markers, detectable moieties, or labels. Thus, for example, a nanoparticle equipped with a targeting ligand attached to its surface can also include another detectable moiety or label. As used herein, the term "detectable moiety" is intended to mean any suitable label, including, but not limited to, enzymes, fluorophores, biotin, chromophores, radioisotopes, colored particles, electrochemical, chemical-modifying or chemiluminescent moieties. Common fluorescent moieties include fluorescein, cyanine dyes, coumarins, phycoerythrin, phycobiliproteins, dansyl chloride, Texas Red, and lanthanide complexes. Of course, the derivatives of these compounds are included as common fluorescent moieties.

The detection of the detectable moiety can be direct provided that the detectable moiety is itself detectable, such as, for example, in the case of fluorophores. Alternatively, the detection of the detectable moiety can be indirect. In the latter case, a second moiety reactable with the detectable moiety, itself being directly detectable can be employed.

A composition, including at least one nanoparticle, can be administered to a subject orally, parenterally (e.g., intravenously), by intramuscular injection, by intraperitoneal injection, transdermally, extracorporeally, topically or the like. Parenteral administration of a composition, if used, is generally characterized by injection. Injectables can be prepared in conventional forms, either as liquid solutions or suspensions, solid forms suitable for solution of suspension in liquid prior to injection, or as emulsions.

The compositions, including nanoparticles, can be used in combination with a pharmaceutically acceptable carrier. By "pharmaceutically acceptable" is meant a material that is not biologically or otherwise undesirable, i.e., the material can be administered to a subject, along with the nanoparticle, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

Suitable carriers and their formulations are described in Remington: The Science and Practice of Pharmacy (19th ed.) ed. A. R. Gennaro, Mack Publishing Company, Easton, Pa. 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5.0 to about 8.0, and more preferably from about 7.0 to about 7.5. As described above, compositions can be administered intravascularly. Administered compositions can include carriers, thickeners, diluents, buffers, preservatives, surface active agents and the like in addition to the composition of choice. Administered compositions can also include one or more active ingredients such as antimicrobial agents, anti-inflammatory agents, anesthetics, and the like.

When used in the described methods, an effective amount of one of the compositions, including the nanoparticles, of the present invention can be determined by one skilled in the art. The specific effective dose level for any particular subject can depend upon a variety of factors including the type and location of the target site, activity of the specific composition employed, the specific composition employed, the age, body weight, general health, sex and diet of the subject, the time of administration, the route of administration, the rate of excretion of the specific composition employed, the duration of the treatment, drugs used in combination or coincidental with the specific composition employed, and like factors well known in the medical arts. For example, it is well within the skill of the art to start doses of the composition at levels lower than those required to achieve the desired diagnostic or imaging effect and to gradually increase the dosage until the desired effect is achieved. If desired, an effective dose can be divided into multiple doses for purposes of administration.

Depending on the exemplary factors above, on the composition used, on the intended target site for the composition, and whether active or passive targeting of the described compositions is used, the time between administration of the described compositions and the detection of the described nanoparticles within the subject can vary. For example, detection of the described nanoparticles can be performed at one or more time seconds, minutes, hours, days, and/or weeks after administration of the compositions to the subject. When and how frequently methods of detection of an administered composition are performed can be determined by one skilled in the art through routine administration and detection.

The described methods can be used to a detect cell. In some examples, the cell can be a macrophage that has engulfed a metallic particle or composition. The macrophage can be located anywhere in a subject, for example, in the eye or in a vulnerable plaque. In other examples, the cell can be a cancer cell, wherein a metallic particle has been targeted to the cell. A cancer cell can be targeted anywhere in the subject. In other examples, the cell can be any cell of a subject that has been targeted with a metallic particle.

A detected cell can be killed or injured by contacting the composition comprised by the cell with energy. Energy can be applied to a particle comprised by the cell. Thus, the described particles can be used for detection of the cell and to receive energy to kill the detected cell. A cell can be killed by heating a particle of the detected cell.

The term kill is intended to include any change made to a cell caused by the application of energy to the cell that leads to or causes immediate or eventual death of that cell. For example, light energy can be applied to the cell to cause injury that leads to or causes immediate or eventual death of the cell.

An exemplary method for detecting and killing a cell comprises detecting the cell, wherein the cell comprises a cellular membrane and a metallic composition, using a phase sensitive optical coherence tomographic imaging modality. The metallic composition can be heated to kill the cell. The metallic composition comprised by the cell can be heated by contacting the metallic composition with energy that causes the metallic particle to increase in temperature, wherein the heating is sufficient to kill or lethally injure the detected cell. For example the metallic particle can be moved with a magnetic filed to an extent sufficient to heat the particle to kill or injure a cell.

The step of detecting the call can further comprise causing a non-lethal change in the cell by contacting the metallic composition with energy sufficient to cause the non-lethal change in the cell. Some exemplary non-lethal changes are described above. The cell can then be detected by detecting the non-lethal change in the cell.

The non-lethal change in the cell can be caused by applying a magnetic field to the cell or metallic particle comprised by the cell. The non-lethal change in the cell can also be caused by applying light energy to the cell or metallic particle comprised by the cell. Such light energy can be produced by a laser. In some exemplary aspects, the energy that causes the non-lethal change in the cell and the energy that causes the metallic particle to increase in temperature are of the same type. For example, the energy can be light energy. Moreover, the energy can be generated by the same source. Thus, the energy that causes the non-lethal change can be produced by the same system component as the energy generated to heat and kill the cell. The energy, however, can also be generated by a different source and can be of differing types. In some exemplary aspects, the energy that causes the non-lethal change can be magnetic filed energy and the energy that causes the increase in temperature can be light energy.

The methods described herein can comprise heating a metallic composition comprised by a cell by contacting the metallic composition with energy capable of heating the metallic composition, wherein the heating is sufficient to kill or lethally injure the detected cell. Other non-limiting examples of energy that can be applied to kill a cell include any energy that can move the particle of the cell. Movement of the particle can be used to heat the particle to a sufficient degree to kill the cell. For example, magnetic and sonic energy can be used.

An effective cell killing protocol can vary with such factors as the particular cell being killed, the tissue in proximity to the cell, the type and composition and characteristics of the particle, the number of particles, the type of pathology being treated, the duration of the treatment, characteristics of the treatment (i.e. wavelength, fluence, pulse duration and number of pulses) the nature of concurrent therapy (if any), the type of energy being applied to contact the particle of the cell, the properties of the surrounding media or amount of water. An effective killing protocol can be readily determined by one of ordinary skill in the art using routine experimentation.

After detecting a cell, for example a macrophage associated with vulnerable plaque, selective pulsed laser photothermolysis can be used to heat the nanoparticles and selectively injure and/or kill these cells. By absorbing light energy, the nanoparticle or clusters of nanoparticles temperature increases and can induce explosive vaporization of a thin layer of fluid in contact with the nanoparticle, as to cause a microexplosion within the cell. A conventional vapor bubble can be created that expands on the nano-second timescale as the initial high vapor pressure overcomes the surface tension of the fluid. The expansion and collapse of bubbles can also cause a second shock wave that travels outward and interacts with the cell to disrupt the cellular membrane. Cells that have nanoparticles can be killed, while adjacent cells can remain viable. Additionally, the heating energy, for example, a pulsed laser light can be used to selectively heat the macrophages to induce apoptosis, protein inactivation through denaturation or coagulation of protein form increased temperature of the nanoparticle by the pulsed laser, or damage to specific cellular structures by the interaction of the heated nanoparticle and cellular structures.

A spatially localized temperature increase can be generated within individual macrophages or other cells when incident photons are absorbed by the nanoparticles. Spatially selective confinement can be accomplished by using laser dosimetry with a wavelength that is absorbed by the nanoparticles and pulse duration for spatial confinement within the macrophage or other cells. Selection of appropriate pulse duration can be used to allow application of the principle of selective photothermolysis so that temperature increase can be confined more to macrophages or other cells that have engulfed the nanoparticles or been targeted by the nanoparticles. Neighboring cells not comprising the metallic composition can be spared.

If light energy is used to kill a detected cell, principles of selective photothermolysis can be used to determine the proper killing protocol or parameters. Using selective photothermolysis, four exemplary parameters that can be determined in selecting a killing protocol include wavelength of the energy source, dose (energy/area), pulse duration, and spot size. To select an appropriate wavelength, the absorption properties of the particle or cluster of particles and the cell and/or surrounding tissues can be determined. A wavelength of killing light energy can be selected to be more strongly absorbed by the particle than the cell or any surrounding tissue or any tissue or composition between the source and the particle. For example, the absorbance spectrum of fat, normal aortic tissue and oxygenated hemoglobin are known and nadir at about 700 nm. Although water has a nadir at about 500 nm, its absorbance is negligible at about 700 nm. As described herein, exemplary nanoparticles comprising, for example, iron oxide cores with gold shells can be used, which can absorb at about 700 nm. An outermost coating comprising dextran with a particle diameter less than 40 nm can be used to reduce uptake by liver and spleen, thereby prolonging blood circulation time to increase plaque based macrophage uptake.

Thus, wavelength can be determined based on the absorption of the targeted particle and the absorption of other compositions in the subject, such as tissues, endogenous chromophores, protein composition, or any other absorptive characteristic of the subject imposed between the energy source and the target particle.

The pulse duration can be determined by estimating the thermal relaxation time of the target particle. Thermal relaxation time can be based on the geometry of the particle and the diffusion of heat into media or tissue surrounding the target particle.

An appropriate dose can also be determined. The dosage used can be related to the pulse duration. As pulse duration is lessened, the temperature used to kill a cell can be elevated. The change in temperature used for a given pulse duration for killing a cell can be determined by using the Aharenius damage integral, which is known to those skilled in the art.

The spot size used can also be related to fluence. Thus, a desired spot size can be selected based on the desired fluence. Spot size can be selected to be approximately equal to the depth of the targeted cells.

Light energy can be generated by a light source for killing a cell. The light energy can be emitted over a multiplicity of optical wavelengths, frequencies, and pulse durations to achieve both OCT imaging and heating of the nanoparticles. In one example, the heating of the nanoparticle with light near the green spectrum can be used to cause cellular death in the tissue targeted and localized with nanoparticles. In order to achieve heating of the nanoparticle and killing of the cell, the pulse duration can be about 10 nanoseconds or less for particles smaller than 100 nm. One of skill in the art will appreciate that different pulse durations can used for different sized nanoparticles in order to achieve heating of the nanoparticle and cellular death. The principle of selective photothermolysis can be used to specify the appropriate pulse duration for targeted particles or clusters of particles of a given size. If mechanical damage is to be achieved, the pulse duration can be selected so that generated acoustic energy is confined in the particle or clusters of particles.

Also provided herein are systems for detecting a cell or metallic composition. An exemplary system comprises a magnet for applying a magnetic field to a cell and a phase sensitive optical coherence tomographic imaging modality for detecting modified strain field in the cell and/or metallic composition due to external excitation. A pulsed light source can be applied to generate a modified thermoelastic strain field surrounding the nanoparticle or cluster of nanoparticles. The phase sensitive optical coherence tomographic imaging modality can comprise a probe for transmitting and receiving light energy to and from the cell. The probe can be an intravascular probe. An exemplary system can also comprise a light source for applying light energy to heat a metallic composition sufficient to generate a thermoelastic strain field and then kill a cell comprising the metallic composition or particle. In this approach, pulsed light energy can be absorbed by the nanoparticles or clusters of nanoparticles to generates a thermoelastic strain field. The thermoelastic strain field can be measured using phase-sensitive OCT by recording images before and after pulsed laser exposure. By using block correlation algorithms similar to those used in ultrasound, the thermoelastic strain field can be measured. The cells containing the nanoparticle or clusters of nanoparticles can be targeted for killing by applying a laser pulse and using the principles of selective photothermolysis as is well know to those skilled in the art. The light source for heating and killing a cell can be selectively activated by a user. The light source for generating the thermoelastic strain field and the light source for killing targeted cells containing nanoparticles or clusters of nanoparticles can be delivered to the target site through the same optical waveguide (fiber) used for OCT imaging or can be delivered through an alternative optical waveguide (fiber) that is arranged to irradiate the same tissue site at that imaged with OCT. Other exemplary, systems can comprise other energy sources capable of heating a metallic composition sufficient to kill a cell comprising the metallic composition or particle.

An exemplary system for detecting and killing a cell can comprise a phase sensitive optical coherence tomographic imaging modality for detecting the cell. As described above, the cell can comprise a cellular membrane and a metallic particle or composition. The system can further comprise an energy source for heating the metallic particle or composition. The source can provide energy for heating the composition that is sufficient to kill or lethally injure the detected cell. In some exemplary aspects, the system can further comprise an energy source for causing a non-lethal change in the cell. For example, the energy source for causing a non-lethal change in the cell can produce a magnetic field. The energy source for causing a non-lethal change in the cell can also produce light or sound. The energy source for causing the non-lethal change in the cell and the energy source for heating the metallic particle can be of the same type. For example, each energy source can generate and/or transmit light. In some exemplary aspects, the energy source for causing the non-lethal change in the cell and the energy source for heating the metallic particle are the same source. In other exemplary aspects, the energy source for causing the non-lethal change in the cell and the energy source for heating the metallic particle are different sources and/or different types of energy. For example, the energy source for causing the non-lethal change can generates and/or transmit magnetic filed energy and the energy source for causing the heating can generate and/or transmits light energy. Thus, in some exemplary aspects the systems described herein can comprise at least three separate sources of energy. One source of energy can be the light energy used for the OCT imaging as would be known to one skilled in the art. Such light energy can be referred to as imaging light energy. A second source can be used to produce energy to causes a change in a cell. Such sources to cause changes in a cell can comprise sources that generate magnetic fields, light, sound and any other energy that can cause an OCT detectable change in a cell. A third source of energy can be used to produce energy to cause heating of the metallic composition comprised by the cell to kill or lethally injure the cell. Such sources can increase the temperature of a metallic particle in the cell. For example, any source that can increase the particle temperature can be used. Exemplary sources include light energy sources and magnetic force generators that can cause an increase in temperature of the particle by inducing movement of the particle. As described above, less than there sources can be also be used. For example, two sources of energy can be used. In this example, light energy for imaging can be produced by the OCT imaging modality and cell changing and killing energy can be generated by a second energy source, which can also be light energy.

The phase sensitive optical coherence tomographic imaging modality included in the system can comprise a light source, a light splitter, a probe and a reference reflector. Light energy generated by the light source can be transmitted to and split by the splitter for transmission to the reference reflector and to the probe. The probe can be configured to transmit at least a portion of the light energy transmitted thereto into a target cell and to receive reflected light energy from the target cell and the reference reflector can be configured to reflect at least a portion of the light energy transmitted thereto. The system can further include a processor for processing reflected light energy from the reference reflector and light energy received by the probe to produce a phase sensitive optical coherence tomography image. The reference reflector can be located in the probe. The system can further comprise a killing light source for delivering light energy to heat particles sufficiently to kill cells. In examples where a separate light source is used for causing a change to the cell and the light source is distinct from the killing light source, another light source (not pictured) can be configured to transmit light energy that causes a change in the cell. Thus, the killing light source can be used to generate a thermoelastic field for detection by phase sensitive OCT.

Although the exemplary systems described below and shown in FIGS. 2 and 4 indicate a multitude of fibers in the sample path, the described systems and methods are not intended to be limited to embodiments having a multitude of fibers. Thus, systems comprising one fiber and methods of using such exemplary systems are covered. Optionally, an exemplary system comprises a probe having a single optical fiber and a rotary reflector in optical communication with the single optical fiber.

FIG. 1 is a block diagram illustrating an exemplary system 100 that can be used for performing the disclosed imaging methods. FIG. 2 is a block diagram illustrating an alternative exemplary system 200 for performing the disclosed imaging methods. FIG. 3 is schematic diagram illustrating portions of the system of FIG. 1. FIG. 4 is a schematic diagram illustrating portions of the system of FIG. 2. These exemplary OCT systems are only examples of phase sensitive spectral domain OCT systems and are not intended to suggest any limitation as to the scope of use or functionality of OCT architectures. Neither should the OCT systems be interpreted as having any dependency or requirement relating to any one or combination of components illustrated in the exemplary OCT systems.

Figure 2:
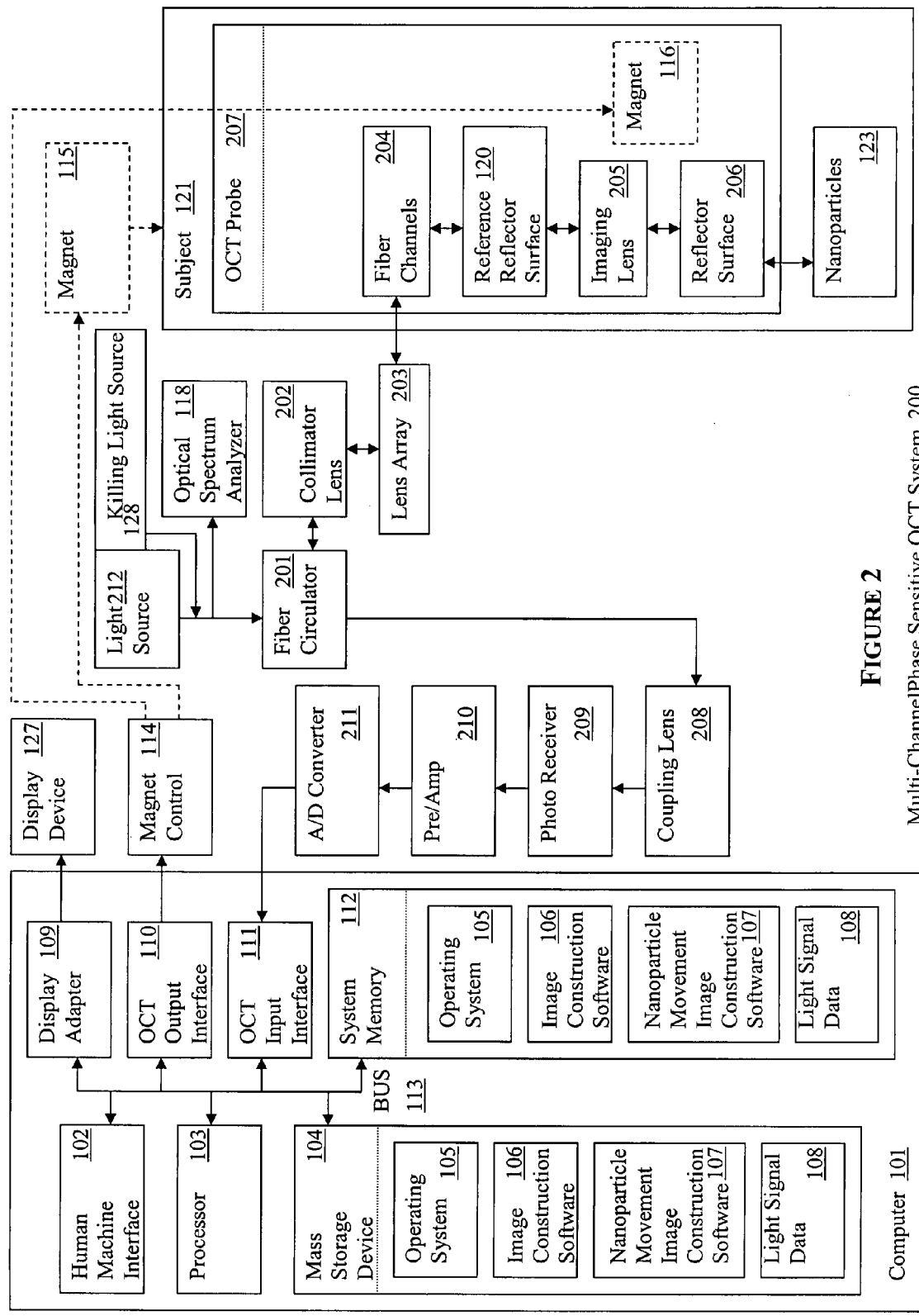
FIG. 2 is a block diagram illustrating an exemplary phase sensitive multi-channel OCT system.
Figure 3:
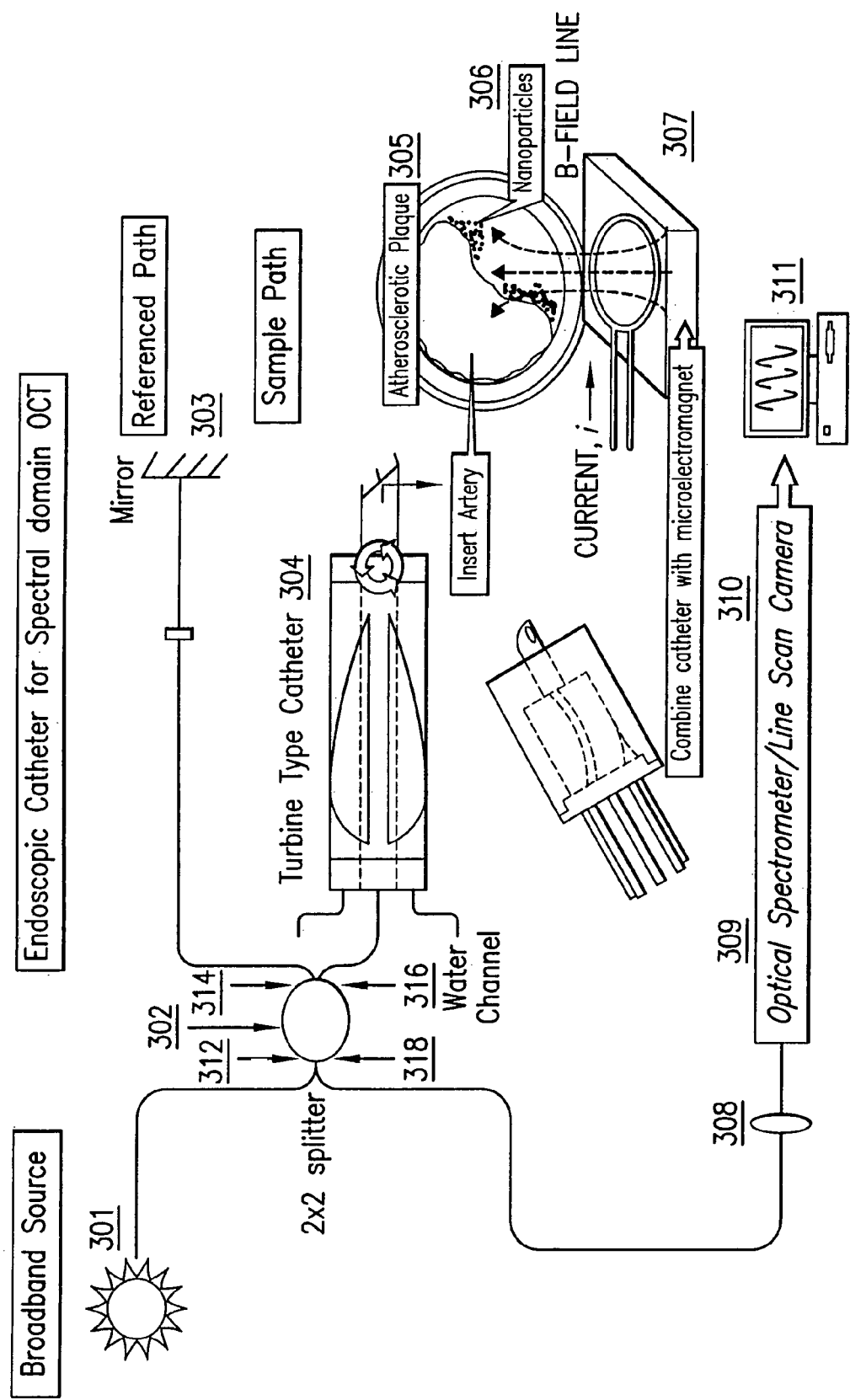
FIG. 3 is a schematic diagram illustrating aspects of the exemplary phase sensitive OCT system of FIG. 1.
Figure 4:
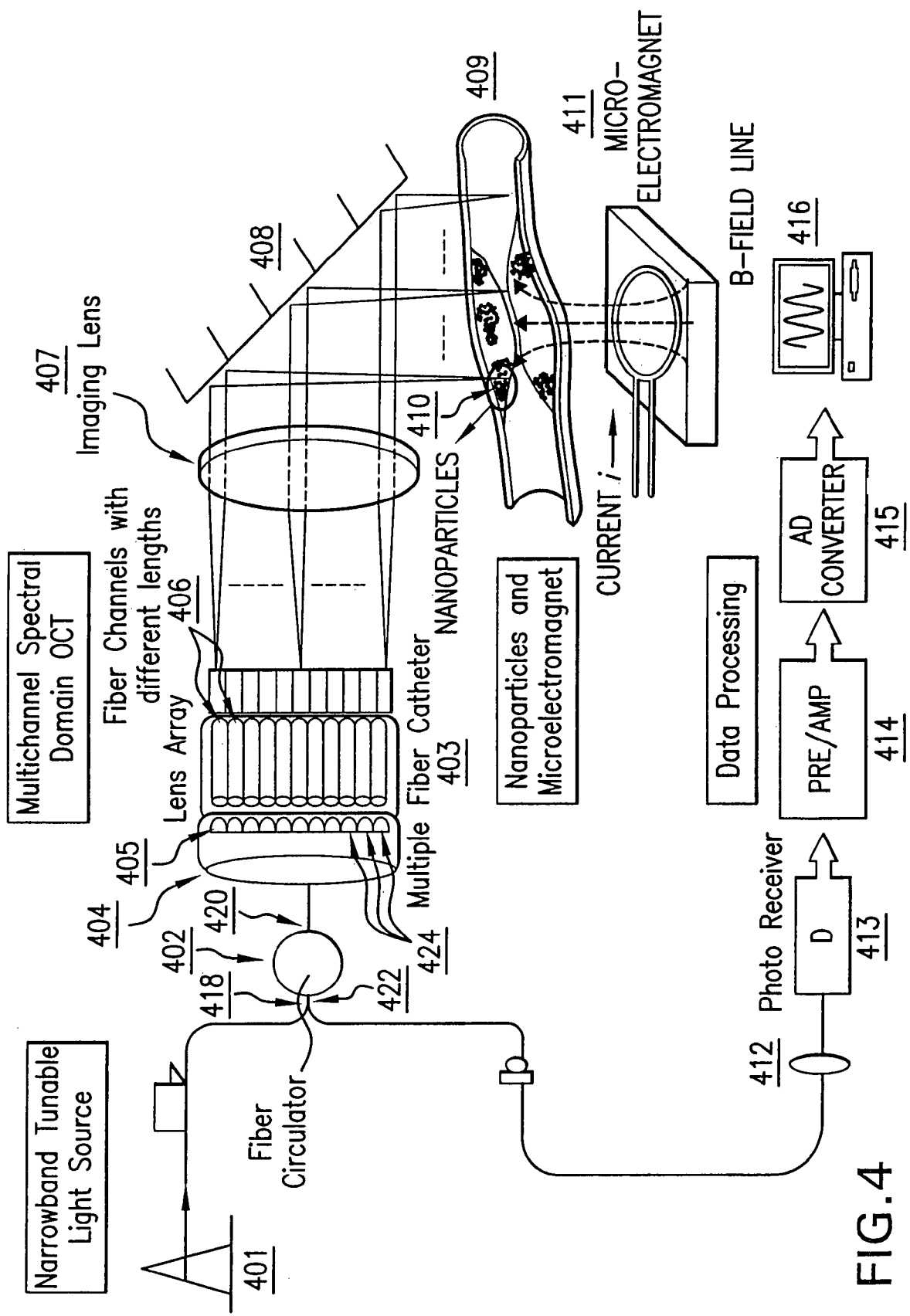
FIG. 4 is schematic diagram illustrating aspects of the exemplary phase sensitive multi-channel OCT system of FIG. 2.

The exemplary OCT systems of FIGS. 1 and 2, 100 and 200 respectively, include a general-purpose computing device in the form of a computer 101, which is shown schematically in FIG. 3 as 311 and is shown schematically in FIG. 4 as 416. The components of the computer 101 can include, but are not limited to, one or more processors or processing units 103, a system memory 112, and a system bus 113 that couples various system components including the processor 103 to the system memory 112.

The system bus 113 represents one or more of several possible types of bus structures, including a memory bus or memory controller, a peripheral bus, an accelerated graphics port, and a processor or local bus using any of a variety of bus architectures. By way of example, such architectures can include an Industry Standard Architecture (ISA) bus, a Micro Channel Architecture (MCA) bus, an Enhanced ISA (EISA) bus, a Video Electronics Standards Association (VESA) local bus, and a Peripheral Component Interconnects (PCI) bus also known as a Mezzanine bus. This bus, and all buses specified in this description can also be implemented over a wired or wireless network connection. The bus 113, and all buses specified in this description can also be implemented over a wired or wireless network connection and each of the subsystems, including the processor 103, a mass storage device 104, an operating system 105, an image construction software 106, a nanoparticle movement image construction software 107, light signal data 108, the system memory 112, an OCT input interface 111, an OCT output interface 110, a display adapter 109, a display device 127, a human interface device 102, and a digital image capture device, can be contained within one or more remote computers (not shown) at physically separate locations, connected through buses of this form, in effect implementing a fully distributed system.

The computer 101 can include a variety of computer readable media. Such media can be any available media that is accessible by the computer 101 and includes both volatile and non-volatile media, removable and non-removable media.

The system memory 112 includes computer readable media in the form of volatile memory, such as random access memory (RAM), and/or non-volatile memory, such as read only memory (ROM). The system memory 112 typically contains data such as light signal data 108 and/or program modules such as operating system 105, image construction software 106 and nanoparticle movement (or cellular membrane tension level or internal strain field change) image construction software 107 that are immediately accessible to and/or are presently operated on by the processing unit 103.

Throughout this application the disclosed methods, compositions and apparatuses for detecting a cell and/or a metallic composition are described herein variously by reference to metallic particle movement, cellular movement, changes in cellular tension level, changes in internal strain field of a cell, and change in neighboring or surrounding cells and/or tissues(s). It will be understood that description of various aspects of the disclosed methods, compositions and apparatuses by reference to detecting one or more of metallic particle movement, cellular movement, changes in cellular tension level, changes in internal strain field of a cell, and change in neighboring or surrounding cells and/or tissues(s) constitutes description of that aspect of the disclosed methods, compositions and apparatuses to the non-referenced detection of metallic particle movement, cellular movement, changes in cellular tension level, changes in internal strain field of a cell, and change in neighboring or surrounding cells and/or tissues(s), unless the context clearly indicates otherwise. Thus, nanoparticle movement image construction software can also include or alternatively include cellular movement, changes in cellular tension level, changes in internal strain field of a cell, and change in neighboring or surrounding cells and/or tissues(s) image construction software.

The computer 101 can also include other removable/non-removable, volatile/non-volatile computer storage media. By way of example, FIG. 1 illustrates a mass storage device 104 which can provide non-volatile storage of computer code, computer readable instructions, data structures, program modules, and other data for the computer 101. For example, a mass storage device 104 can be a hard disk, a removable magnetic disk, a removable optical disk, magnetic cassettes or other magnetic storage devices, flash memory cards, CD-ROM, digital versatile disks (DVD) or other optical storage, random access memories (RAM), read only memories (ROM), electrically erasable programmable read-only memory (EEPROM), and the like.

Any number of program modules can be stored on the mass storage device 104, including by way of example, an operating system 105, image construction software 106, nanoparticle movement (or cellular membrane tension level or internal strain field change) image construction software 107, and light signal data 108. Each of the operating system 105, image construction software 106, nanoparticle movement (or cellular membrane tension level or internal strain field change) image construction software 107, light signal data 108 (or some combination thereof) can include elements of the programming image construction software 106 and the nanoparticle movement (or cellular membrane tension level or internal strain field change) image construction software 107.

A user can enter commands and information into the computer 101 via an input device (not shown). Examples of such input devices include, but are not limited to, a keyboard, pointing device (e.g., a "mouse"), a microphone, a joystick, a serial port, a scanner, and the like. These and other input devices can be connected to the processing unit 103 via a human machine interface 102 that is coupled to the system bus 113, but can be connected by other interface and bus structures, such as a parallel port, game port, or a universal serial bus (USB).

A display device 127 can also be connected to the system bus 113 via an interface, such as a display adapter 109. For example, a display device can be a monitor. In addition to the display device 127, other output peripheral devices can include components such as speakers (not shown) and a printer (not shown) which can be connected to the computer 101 via an input/output interface (not shown).

The computer 101 can operate in a networked environment using logical connections to one or more remote computing devices (not shown). By way of example, a remote computing device can be a personal computer, portable computer, a server, a router, a network computer, a peer device or other common network node, and so on.

Logical connections between the computer 101 and a remote computing device (not shown) can be made via a local area network (LAN) and a general wide area network (WAN). Such networking environments are commonplace in offices, enterprise-wide computer networks, intranets, and the Internet. In a networked environment, image construction software 106, nanoparticle movement (or cellular membrane tension level or internal strain field change) image construction software 107 and light signal data 108 depicted relative to the computer 101, or portions thereof, can be stored in a remote memory storage device (not shown). For purposes of illustration, application programs and other executable program components such as the operating system are illustrated herein as discrete blocks, although it is recognized that such programs and components reside at various times in different storage components of the computing device 101, and are executed by the data processor(s) of the computer.

An implementation of the image construction software 106 and the nanoparticle movement (or cellular membrane tension level or internal strain field change) image construction software 107 can be stored on or transmitted across some form of computer readable media. Computer readable media can be any available media that can be accessed by a computer. By way of example, and not limitation, computer readable media can comprise "computer storage media" and "communications media." "Computer storage media" include volatile and non-volatile, removable and non-removable media implemented in any method or technology for storage of information such as computer readable instructions, data structures, program modules, or other data. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by a computer.

The light signal data 108 can enter the computer 101 via the OCT input interface 111. The OCT output interface can be IEEE-488, IEEE-1394, Universal Serial Bus (USB), or the like. The light signal data 108 can be stored in mass storage device 104 and transferred to system memory 112 as light signal data 108 to be used by image construction software 106 and nanoparticle movement (or cellular membrane tension level or internal strain field change) image construction software 107.

The OCT output interface 110 connects the computer 101 to a magnet control 114. This connection can allow a user to regulate the current sent to a magnet 115 and a magnet 116 by the magnet control 114. The magnet control 114 directs current flow into the magnets 115 or 116. The magnet control 114 can work in conjunction with a line scan camera 139 so that a user-specified field pulse sequence is present at the scanning site.

FIG. 1 illustrates an example of a Phase Sensitive OCT system 100. The Phase Sensitive OCT system 100 can be utilized in conjunction with the computer and network architectures described above.

The Phase Sensitive OCT system 100 can include a general-purpose computing device in the form of a computer 101 which is shown schematically in FIG. 3 as 311, and all subsystems of the computer 101, as previously described. The Phase Sensitive OCT system 200 can also include, as previously described, a display device 127, a magnet control 114, and a magnet 114 and/or a magnet 115.

Light energy can be generated by a light source 117, which is shown schematically in FIG. 3 as 301. The light source 117 can be a broadband laser light source coupled into optical fiber emitting light energy over a broad range of optical frequencies. For example, the range can be from about 400 nanometers to about 1600 nanometers. The light energy can be emitted over a multiplicity of optical wavelengths or frequencies. As used herein, optical fiber can refer to glass or plastic wire or fiber. Optical fiber is indicated on FIGS. 1, 2, 3, and 4 as lines connecting the various blocks of the figures. Where light energy is described as "passing," "traveling," "returning," "directed," or similar movement, such movement can be via optical fiber.

A fraction of the generated light energy passes from the light source 117 into an optical spectrum analyzer 118. The optical spectrum analyzer 118 measures optical frequency as the light energy is emitted from the light source 117 as a function of time. The optical spectrum analyzer 118 samples a portion of the light emitted by the light source 117. The optical spectrum analyzer 118 monitors the power spectral density of light entering the splitter 119. The remaining fraction of light energy from the light source 117 passes into a splitter 119 which is shown schematically in FIG. 3 as 302. The splitter 119 can be a device with four ports 312, 314, 316, 318 on schematic diagram FIG. 3. Port 1 (312) allows light energy to enter the splitter 119. Ports 2 (314) and 3 (316) allow light energy to leave and re-enter the splitter 119. Port 4 (318) allows light energy to leave the splitter 119. The splitter 119 couples the light into Port 1 (312). The splitter 119 divides the light according to a pre-determined split ratio selected by a user. For example, the split ratio can be 50/50 wherein half of the light energy entering the splitter 119 at Port 1 (312) exits the splitter 119 through Port 2 (314) and half exits the splitter 119 through Port 3 (316). In another non limiting example, the split ratio can be 60/40 wherein 60% of the light energy passes through Port 2 (314) and 40% of the light energy passes through Port 3 (316).

A fraction of the light energy (determined by the split ratio) that exits the splitter 119 through Port 2 (314) travels to a reference reflector surface 120 which is shown schematically in FIG. 3 as 303. The light energy is reflected from the reference reflector surface 120 back to the splitter 119 into Port 2 (314). The reference reflector can be, by way of example, but not limitation, a planar metallic mirror or a multilayer dielectric reflector with a specified spectral amplitude/phase reflectivity. The remaining fraction of light that entered splitter 119 through Port 1 (312) exits splitter 119 through Port 3 (316) and enters an OCT probe 122 which is shown schematically in FIG. 3 as 304. The OCT probe 122 can be a turbine-type catheter as described in Patent Cooperation Treaty application PCT/US04/12773 filed Apr. 23, 2004 which claims priority to U.S. provisional application 60/466,215 filed Apr. 28, 2003, each herein incorporated by reference for the methods, apparatuses and systems taught therein. The OCT probe 122 can be located within a subject 121 to allow light reflection off of subject 121 tissues, which is shown schematically in FIG. 3 as 305 and nanoparticles 123 which are shown schematically in FIG. 3 as 306.

The light energy that entered OCT probe 122 is reflected off the tissue of subject 121 and nanoparticles 123. The reflected light energy passes back through the OCT probe 122 into the splitter 119 via Port 3 (316). The reflected light energy that is returned into Port 2 (314) and Port 3 (316) of the splitter 119 recombines and interferes according to a split ratio. The light recombines either constructively or destructively, depending on the difference of pathlengths. A series of constructive and destructive combinations of reflected light can be used to create an interferogram (a plot of detector response as a function of optical path length difference($c\tau$) or optical time-delay ($\tau$)). Each reflecting interface from the subject 121 and the nanoparticles 123 can generate an interferogram. The splitter 119 can recombine light energy that is returned through Port 2 (314) and Port 3 (316) so that the light energies interfere. The light energy is recombined in the reverse of the split ratio. For example, if a 60/40 split ratio, only 40% of the light energy returned through Port 2 (314) and 60% of the light energy returned through Port 3 (316) would be recombined. The recombined reflected light energy is directed out Port 4 (318) of the splitter 119 into a coupling lens 137 which is shown schematically in FIG. 3 as 308. The coupling lens 137 receives light from the output of the splitter 119 and sets the beam etendue (beam diameter and divergence) to match that of the optical spectrometer 138. The coupling lens 137 couples the light into an optical spectrometer 138 which is shown schematically in FIG. 3 as 309. The optical spectrometer 138 can divide the recombined reflected light energy light into different optical frequencies and direct them to different points in space which are detected by a line scan camera 139 which is shown schematically in FIG. 3 as 310. The line scan camera 139 performs light to electrical transduction resulting in digital light signal data 108. The digital light signal data 108 is transferred into the computer 101 via the OCT input interface 111. Interface between the line scan camera 139 and computer 101 can be, for example, IEEE-488, IEEE-1394, Universal Serial Bus (USB), or the like. The digital light signal data 108 can be stored in the mass storage device 104 or system memory 112 and utilized by the image construction software 106 and the nanoparticle movement (or cellular membrane tension level or internal strain field change) image construction software 107.

The system 100 can further comprise a killing light source 128. The killing light source can be activated by a user to apply light energy sufficient to heat a nanoparticle of a detected cell. In some aspects, the killing light source can be used to cause a non-lethal change in the cell that can be detected using the OCT imaging modality. For example, the killing light source can be used to generate a thermoelastic field that can be detected using a phase sensitive OCT system. The operating parameters of the killing light source can be adjusted and operated using the computer 101 and input from a user through the human machine interface 102. The energy from the killing light source 128 can be directed along the same fiber (optical waveguide) path or channels as the light from the light source 117. Thus, the OCT probe can comprise one or more channels for directing light energy into the subject. When the OCT probe is used to direct multiple channels of light onto the subject, a wavelength division multiplexer (WDM) can be used to combine light emitted from OCT and killing sources. If one channel is used, light from the light source 117 or light from the killing light source 128 can be selectively directed through the channel into the subject. The same OCT probe (optical wave guide) can therefore be used to direct detecting light into the subject for generating a thermoelastic field or for killing cells. In other examples, the killing light may be applied from a source external to the subject and applied through a separate waveguide that is directed to apply light at a site coincident with OCT detecting light. In this case a dichroic beamsplitter can be used. Alternatively, the killing source may be magnet 116, which evokes a magnetic field sufficient to increase the temperature to cause cellular death. A user operates magnet control 114 to increase the magnetic field internal or external the body, as indicated below.

The preceding exemplary phase sensitive OCT system is only one example of the contemplated systems for imaging tissues and nanoparticles. Variations in layout and equipment known to one skilled in the art are also contemplated. Another example of a phase sensitive OCT system that can be used to perform the method of the invention is illustrated in FIG. 2.

FIG. 2 is an exemplary block diagram of a Multi-Channel Phase Sensitive OCT system 200. The exemplary Multi-Channel Phase Sensitive OCT system 200 can include a general-purpose computing device in the form of the computer 101, which is shown schematically in FIG. 4 as 416, and all subsystems of the computer 101, as described herein. The exemplary multi-channel Phase Sensitive OCT system 200 can also include, as previously described, a display device 127, a magnet control 114, and a magnet 114 or a magnet I5.

Light energy for OCT detection is generated by a light source 212, which is shown schematically in FIG. 4 as 401. The light source 212 can be a narrow band tunable laser light source wherein the optical wavelengths generated range from about 400 nanometers to about 1600 nanometers. Appropriate selection of a range of optical wavelengths can be readily determined by one skilled in the art. For example, if light energy is to go through substantial water path, i.e., deep tissue, then an operator can select longer optical wavelengths. For example, 1300-1600 nanometers. The light spectrum can be continuously varied in time, over a specified spectral region. A fraction of the light energy passes from the light source 212 into an optical spectrum analyzer 118. The optical spectrum analyzer 118 samples a portion of the light emitted by the light source 212. The optical spectrum analyzer 118 monitors the power spectral density of light entering the circulator 201. The optical spectrum analyzer 118 can measure optical frequency as it is emitted from the light source 212 as a function of time. The remaining fraction of light energy generated by the light source 212 passes into a fiber circulator 201, which is shown schematically in FIG. 4 as 402. The fiber circulator 201 can comprise three ports, designated Port 1, Port 2, and Port 3, which are shown schematically in FIG. 4 as 418, 420, and 422 respectively. Light energy can enter Port 1 (418). Light energy can exit and re-enter Port 2 (420). Light energy can exit Port 3. The fiber circulator 201 can recombine light energy that re-enters via Port 2 (420). Light energy from the light source 212 passes into the fiber circulator 201 through Port 1 (418). The light energy exits the fiber circulator 201 through Port 2 (420) and enters an OCT probe 207, which is shown schematically in FIG. 4 as 403. The light energy is coupled to a collimator lens 202, which is shown schematically in FIG. 4 as 404. The collimator lens 202 focuses the light emitted from the fiber at a point infinitely far from the fiber tip.

The light energy is collimated into a lens array 203, which is shown schematically in FIG. 4 as 405. The lens array 203 can comprise a lattice of microlenses or lenslets, which are shown schematically in FIG. 4 as 422. The number of microlenses in the lens array 203 can be readily determined by one skilled in the art. For each microlens, there is a fiber channel 204, which is shown schematically in FIG. 4 as 406, that is coupled to the microlens. Fiber channels 204 are optical waveguides that confine and guide light along a path. The fiber channels 204 can be varied in length. Choosing an appropriate length for the fiber channels 204 is known to one skilled in the art. The difference in the length between fiber channels 204 can be from about one and a half to about ten times the scan depth in the tissue of a subject 121. This variable length can allow demultiplexing light signal detected from the channels. A fraction of the light energy transmitted into the fiber channels 204 is reflected from a reference reflector surface 120 back into the fiber channels 204, through the lens array 203, into the collimator lens 202 and into the fiber circulator 201. This reflected light energy can serve as a reference reflection. The light energy that is not reflected back from the reference reflector surface 120 passes through the reference reflector surface 120 and onto an imaging lens 205, which is shown schematically in FIG. 4 as 407. The imaging lens 205 images the light energy from the tips of the fiber channels 204 onto the tissue of the subject 121. The light energy passes through the imaging lens 205 onto a reflector surface 206, which is shown schematically in FIG. 4 as 408, which turns the light energy 90 degrees. This allows the light energy to be reflected out radially inside a tissue. There is one reflector surface 206 for each fiber channel 204. The light energy that is turned 90 degrees by the reflector surface 206 is back reflected off of the tissue of subject 121, which is shown schematically in FIG. 4 as 409, and nanoparticles 123, which is shown schematically in FIG. 4 as 410.

The light is reflected from the tissue of subject 121 and the nanoparticles 123. The light energy strikes the reflector surface 206 and is turned back 90 degrees. The light energy is then coupled by the imaging lens 205 through the reference reflector surface 120 and back into each fiber channel 204. The light energy reflected from the nanoparticles 123 and the tissue of subject 121 recombines and interferes with the light reflected from the reference reflector surface 120 in the fiber channels 204. The recombined light energy can be coupled back into the lens array 203 through the collimator lens 202 and back into Port 2 (420) of the fiber circulator 201. The recombined light energy exits the fiber circulator 201 through Port 3 (422). A coupling lens 208, which is shown schematically in FIG. 4 as 412, couples the recombined light energy from the fiber circulator 201 into a photo receiver 209, which is shown schematically in FIG. 4 as 413. The photo receiver 209 converts the light energy signal into a voltage signal that is proportional to the number of photons contained in the recombined light energy. The voltage signal passes from the photo receiver 209 into a pre/amp 210, which is shown schematically in FIG. 4 as 414. The pre/amp 210 takes the voltage signal and amplifies it. The amplified voltage signal enters an A/D converter 211, which is shown schematically in FIG. 4 as 415. The A/D converter 211 digitizes the voltage signal. This digital light signal data then enters the computer 101 through the OCT input interface 111. The digital light signal data 108 can be stored in the mass storage device 104 or system memory 112 and utilized by the image construction software 106 and the nanoparticle movement (or cellular membrane tension level or internal strain field) image construction software 107.

Similar to the system 100, the system 200 can further comprise a killing light source 128. The killing light source can be activated by a user to apply light energy sufficient to heat a nanoparticle of a detected cell. Also, as described above, the killing light source can also be used to cause a non-lethal change in the cell that can be detected using the OCT imaging modality. The operating parameters of the killing light source can be adjusted and operated using the computer 101 and input from a user through the human machine interface 102. The energy from the killing light source 128 can be directed along the same fiber path or channels as the light from the light source 212. Thus, the OCT probe can comprise one or more channels for directing light energy into the subject. If one channel is used, light from the light source 212 or light from the killing light source 128 can be selectively directed through the channel into the subject. The same OCT probe can therefore be used to direct detecting light into the subject and light for killing cells. In other examples, the killing light may be applied from a source external to the subject.

The methods described herein can further comprise generating light energy for at least two successive sweeps of light energy. A sweep is an emission of light from a light source across a range of optical frequencies. Multiple sweeps can be combined with application of a magnetic field to generate images with and without a magnetic field applied.

The methods can further comprise applying a magnetic field to the subject for each of the successive sweeps of the light energy wherein the strength of the magnetic field applied in a sweep is greater than the strength of the magnetic field from the preceding sweep and wherein the magnetic field causes movement of at least one of the metallic nanoparticles. The method can further comprise applying the magnetic field from a source external to the subject or from a source internal to the subject. A coil generating the magnetic field can be integrated into a catheter or can be external to the subject of the scan.

The methods can also comprise applying a pulsed laser to a cell, for example a macrophage, for each of the successive sweeps of light energy wherein the strength of the pulsed laser light is greater than the strength of the pulsed laser light from the preceding sweep and where the pulsed laser light causes movement of at least one of the metallic particles or compositions.

As shown in FIGS. 1 and 2, a non-uniform magnetic field can be applied to the tissue of subject 121 and the nanoparticles 123. The non-uniform magnetic field can be applied by the magnet 116, which is shown schematically in FIG. 3 as 307 and schematically in FIG. 4 as 411, which can be a magnet internal to the OCT probe 122 or the OCT probe 207 or the non-uniform magnetic field can be applied externally to the subject 121 by magnet 115. Magnets 115 and magnet 116 are both controlled by magnet control 114. The magnet control can provide the current source to power magnet 115 and magnet 116 and is under the control of the computer 101. The magnet control 114 interfaces with the computer 101 through the OCT output interface 110. The magnet control 114 can interface with the computer 101 via IEEE-488, IEEE-1394, Universal Serial Bus (USB), or the like. The magnets 115 and 116 can generate both non-lethal changes and lethal changes of the metallic composition, as indicated above. For example, the magnets can generate a magnetic field sufficient to detecting and imaging the metallic composition by optical coherence tomography, and the magnets can generate a magnetic field sufficient to raise the temperature of the metallic composition of the nanoparticle to cause cellular death. The user selects a magnetic field sufficient to induce an increase in temperature of the particular metallic composition. The magnetic field can be adjusted according to the metallic composition's magnetic susceptibility characteristics.

Light energy can be generated for heating a particle and killing a cell by a light source 128. In some aspects, the same light source can be used to create a non-lethal change in the cell. The light source can be a pulsed laser light source coupled into an optical fiber emitting light energy over a broad range of optical frequencies. For example, the range can be from about 100 nanometers to about 2000 nanometers. In some examples, the light for OCT detection can have a wavelength from about 800 nm to about 1300 nm and the killing wavelength can be about 694 nm. Pulsed laser light sources can be pulsed lasers generating picosecond and femtosecond fundamental and second harmonic light pulses in 400-1400 nanometer region, and are generally known in the art. The pulsed lasers include Ti:Sapphire, Cr (4+):Forsterite, Q-switched Nd:YAG, Cr:YAG, Cr (4+):Ca (2)GeO (4)(CUNYITE), Colliding pulse mode-lock lasers, and semiconductor diode lasers. Laser pulses at longer wavelength (>600 nm) can be used for deeper scanning into the tissue sample. Laser pulses at different wavelengths are used to excite different nanoparticles localized in tissues. Laser pulses with different modulation frequencies can be used to regulate heat flow away from nanoparticles.

In one non-limiting example, the light source 128 can emit a pulsed laser of about 532 nanometers with a pulse duration of about 200 microseconds in order to induce cellular death. The light energy sources can be emitted over a multiplicity of optical wavelengths, frequencies, and pulse durations to achieve both OCT imaging and heating of the nanoparticles. The heating of the nanoparticle with light based on photothermolysis principles can be sufficient to cause cellular death in the tissue targeted and localized with nanoparticles. In order to achieve heating of the nanoparticle and killing of the cell, the pulse duration can be, for example, 10 nanoseconds or less for particles smaller than 100 nm. As described above, different pulse durations can used for different sized nanoparticles in order to achieve heating of the nanoparticle and cellular death.

Figure 17:
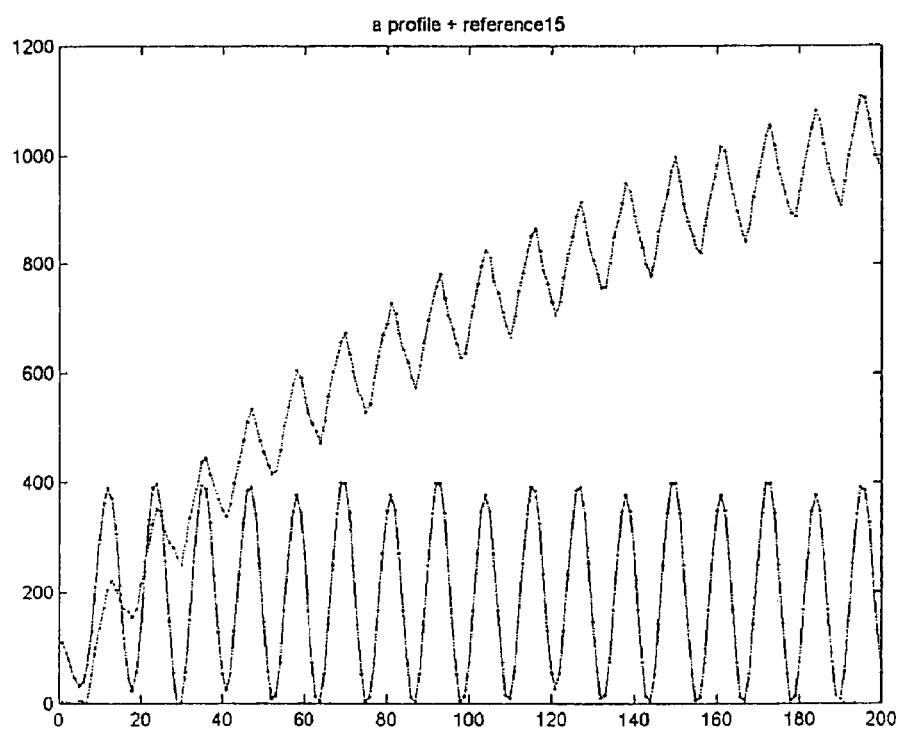
FIG. 17 is the amplitude and phase data used to generate the image displayed in FIGS. 15A and B. The figure shows maximum temperature increase ($\Delta T$: ~18.6° C.) of MION rabbit aorta during 2 seconds of 532 nm laser heating (10 Hz modulation frequency, 400 mW).

Once the image of the macrophage is generated, the user can then select the light source 128 to emit a pulsed laser light energy. In accordance with one exemplary protocol, illustrated in FIG. 17, the pulsed light can be in the green spectrum, preferably 532 nanometers a pulse duration of about 200 microseconds. The pulsed laser green light can cause a temperature increase of 18.6 degrees C., as shown in FIG. 17. Higher temperature increased can also be achieved. For example, temperatures up to and greater than 40 degrees C. can be achieved. Pulsed laser light sources are generally known in the art, such as q-switched, free-running and femtosecond lasers and the like. Ultrashort-pulsed fiber lasers may be used, which demonstrate femtosecond passively mode-locked fiber oscillators by a variety of Kerr-type saturable absorbers. Different wavelengths of light can be used to identify and heat the nanoparticles. Wavelength sensitivity of different nanoparticles can also enhance the specificity of heating endogenous tissue structures as to distinguish pathologic tissue structures from non-pathologic structures. For example, only those nanoparticles that have been selectively targeted or uptaken by tissues can be heated and cause cellular death.

The methods can further comprise processing the received light energy to produce a phase sensitive OCT image. The image produced can have a phase resolution of at least 30 nanometers (nm). Phase resolution is defined as the phase delay of the light signal returning from the tissue scanned. For example, the image can have a phase resolution of about at least 30 nm, 25 nm, 20 nm, 15 nm, 10 nm, 5 nm, 4 nm, 3 nm, or 2 nm.

The processing of the received light energy can be performed by software components. The image construction software 106 and the nanoparticle movement (or cellular membrane tension level or internal strain field) image construction software 107 can be described in the general context of computer-executable instructions, such as program modules, being executed by one or more computers or other devices. Generally, program modules include computer code, routines, programs, objects, components, data structures, etc. that perform particular tasks or implement particular abstract data types. The image construction software 106 and the nanoparticle movement (or cellular membrane tension level or internal strain field) image construction software 107 can also be practiced in distributed computing environments where tasks are performed by remote processing devices that are linked through a communications network. In a distributed computing environment, program modules can be located in both local and remote computer storage media including memory storage devices.

The image construction software 106 can generate an image of the tissue of subject 121 from the light signal data 108. The image construction software 106 can receive the light signal data 108 and can perform a time-frequency transform (e.g. Fourier transform) on the light signal data 108 generating amplitude and phase data. The amplitude and phase data (optical path length difference ($c\tau$) or optical time-delay ($\tau$)) can be separated into discrete channels and a plot of intensity vs. depth (or amplitude vs. depth) can be generated for each channel. Such a plot is known in the art as an "A" scan. The composition of all the "A" scans can comprise one image.

The nanoparticle movement (or cellular membrane tension level or internal strain field) image construction software 107 generates an image of the movement of the nanoparticles 123 from the light signal data 108. The nanoparticle movement (or cellular membrane tension level or internal strain field) image construction software 107 receives the light signal data 108 for at least two successive sweeps of the light source 117 or the light source 212 and performs a Fourier transform on the light signal data 108 generating amplitude and phase data. The amplitude and phase data can be separated into discrete channels, one channel for each fiber channel 204, and a plot of phase vs. depth (optical time-delay ($\tau$)) can be generated for each channel. Points of nanoparticle 123 movement are identified when phase at a given depth changes between two successive sweeps of the light source 117 or the light source 212 corresponding to two applied magnetic field strengths.

Optionally, additional information can be extracted from the light signal data 108 to generate additional images. The light signal data 108 can be further processed to extract the Doppler frequency shift as is readily known to one skilled in the art. The light signal data 108 can also be further processed to generate a Stokes parameter polarimetric image when used in conjunction with polarization detectors (not shown) and polarizing lenses (not shown) to extract polarization data from the light signal 108 as is readily known to one skilled in the art.

The methods and systems can be used to perform molecular identification to stabilize vulnerable plaque that is anticipated to rupture and cause heart attacks, strokes, and progression of peripheral vascular disease. It can also be used to identify macrophages present in degenerative eye diseases which can lead to blindness and selectively kill these pathologic cells to stabilize the eye degeneration. Generally, many cancers are known to be associated with the presence of macrophages, and it may provide a method for early cancer detection and treatment.

EXAMPLES

The following examples are put forth so as to provide those of ordinary skill in the art with a complete disclosure and description of how the compositions, compositions, articles, devices, systems, and/or methods claimed herein are made and evaluated, and are intended to be purely exemplary and are not intended to limit the scope of compositions, compositions, articles, devices, systems, and/or methods. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1

Figure 5A:
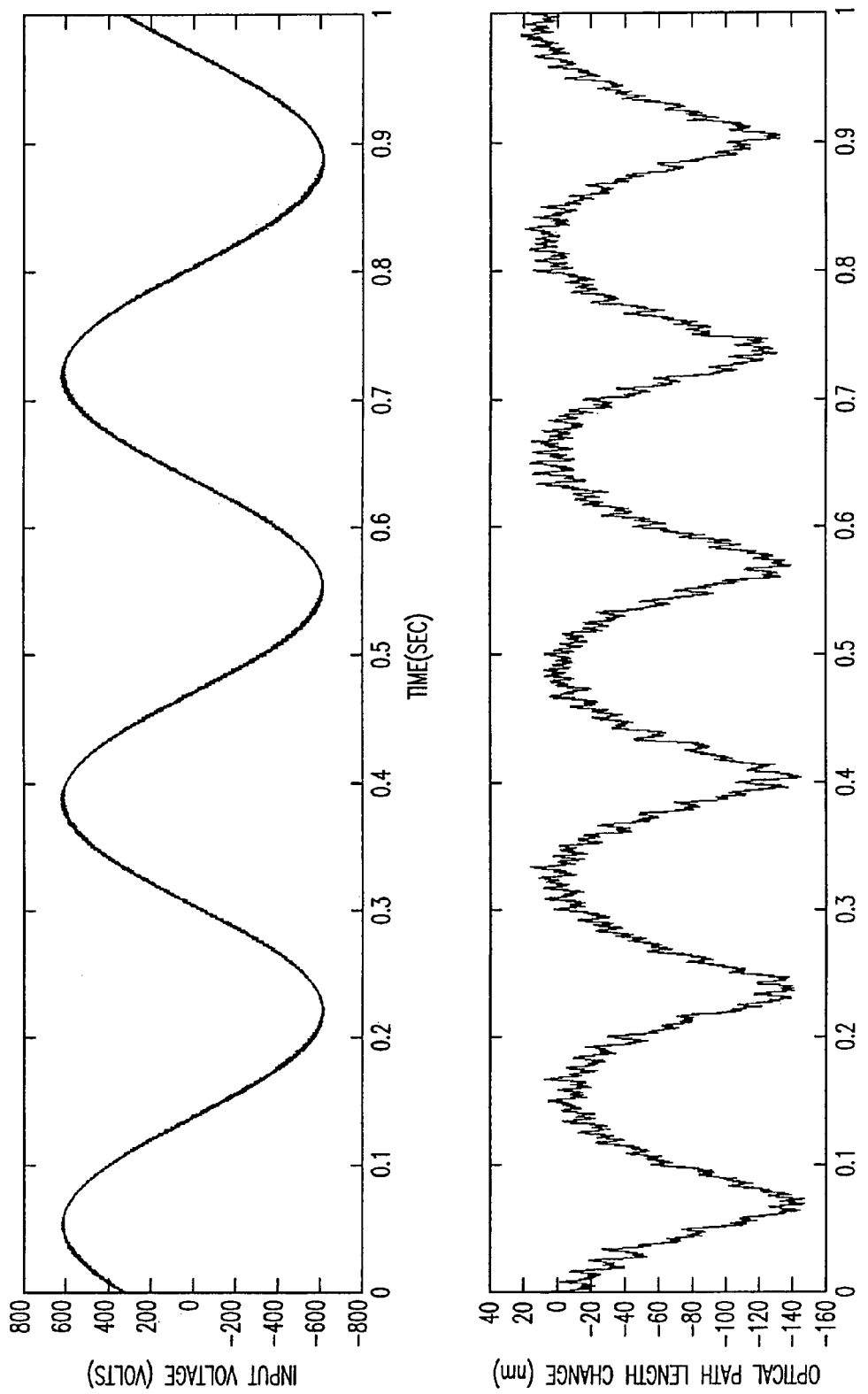
FIGS. 5A and B show solenoid drive signal and optical pathlength change observed in a mouse imaged with metallic nanoparticles (A) and a mouse imaged without metallic nanoparticles (B).
Figure 5B:
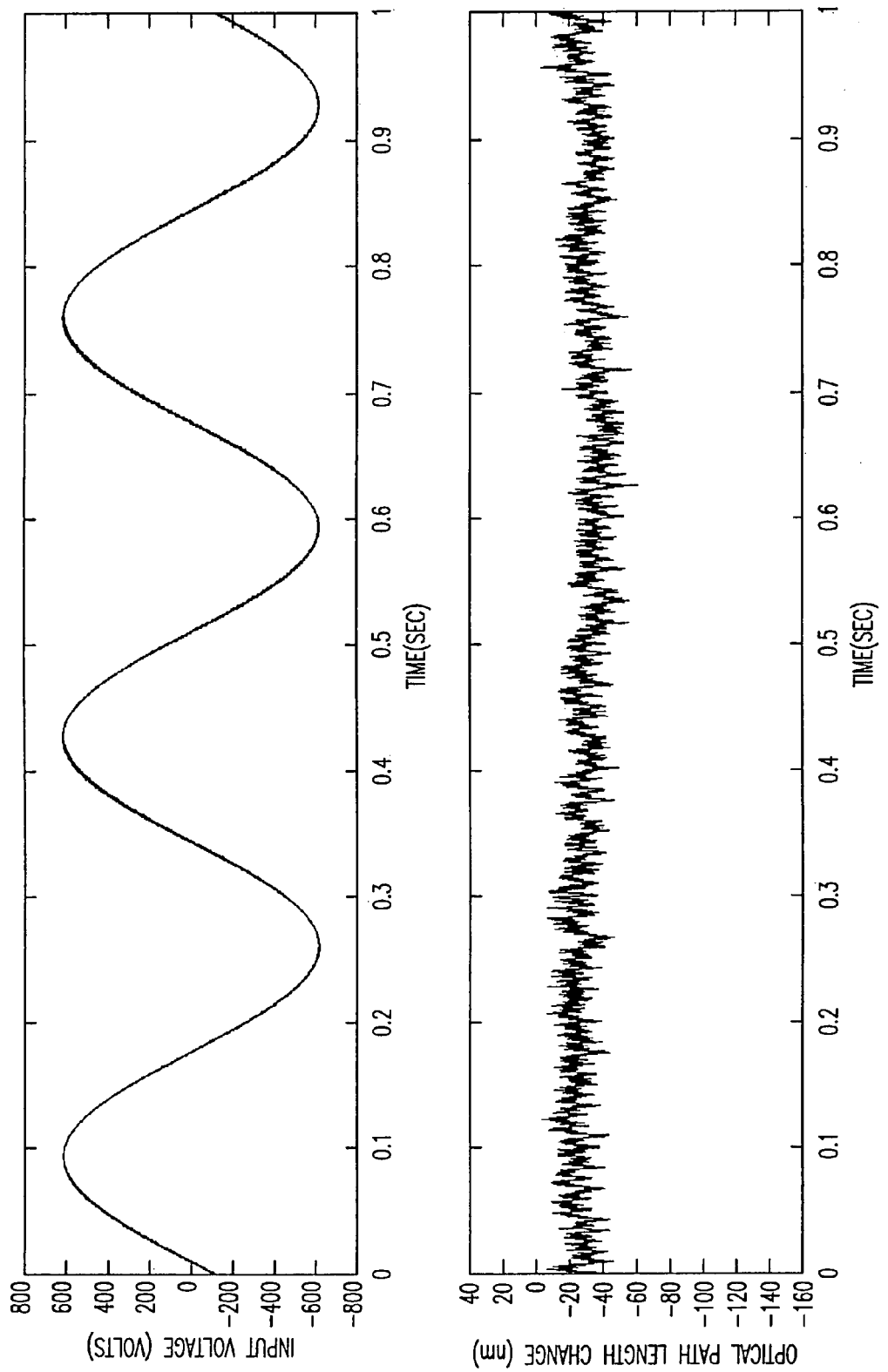

A solenoid coil with a ferrite core was used to apply a sinusoidal magnetic field to tissues taken from the liver of an ApoE −/− knockout mouse. One mouse was loaded with magnetic nanoparticles one week before imaging while an unloaded mouse served as a control. FIG. 5a shows a solenoid drive signal (top) and optical pathlength change (bottom) observed in mouse loaded with nanoparticles. FIG. 5b shows a solenoid drive signal (top) and optical pathlength change (bottom) observed in control mouse (no nanoparticles). These data demonstrate that iron oxide particles that have been ingested by macrophages in livers and spleens of the mice. Moreover, the particles have put in motion with a magnet and detected with differential phase OCT using the systems and methods described herein.

To calculate magnetic field strength a finite element method (FEM) can be used. Maxwell equations subjected to certain boundary conditions can be used to solve low-frequency magnetostatic problems. The use and solution of Maxwell equations are described in, for example, Monk P., Finite Element Methods for Maxwell's Equations, Oxford University Press, 2003, which is incorporated in its entirety by reference.

Maxwell equations can be written as:

$$\nabla \times H = J + \frac{\partial D}{\partial t} \quad (1.1)$$

$$\nabla \times E = -\frac{\partial B}{\partial t} \quad (1.2)$$

$$\nabla \cdot H = \rho \quad (1.3)$$

$$\nabla \cdot B = 0 \quad (1.4)$$

In case of magnetostatic problems $$\left(\frac{\partial D}{\partial t} = 0\right),$$

the magnetic field (H) and magnetic flux density (B) are satisfied with following equations:

$$\nabla \times H = J \quad (1.5)$$

$$\nabla \cdot B = 0 \quad (1.6)$$

B and H are subject to a generalized constitutive relation:

$$B = u_0(H + M) \quad (1.7)$$

Finite element methods (FEM) used magnetic vector potential (A) to find magnetic field strength.

$$B = \nabla \times A \quad (1.8)$$

Equation (1.5) can be rewritten as $$\nabla \times (u_0^{-1} \nabla \times A - M) = J \quad (1.9)$$

From equation (1.9), magnetic field strength and flux density can be solved. The symbols and unit for electromagnetic quantities for solving FEM problems include:
H: Magnetic field (Ampere/m)
E: Electric field (Volt/meter)
B: Magnetic flux density (Tesla)
D: Electric flux density (Coulomb/meter)
A: Magnetic potential (Weber/meter)
M: Magnetization (Ampere/meter)
$u_0$: Permeability of vacuum=$4\pi \cdot 10^{-7}$ (H/m)

$$\nabla \cdot B = divB = \frac{\partial}{\partial x}B_x + \frac{\partial}{\partial y}B_y + \frac{\partial}{\partial z}B_z$$

($\nabla \cdot B$ is divergence of B)

Magnetic fields of between about 1.5 and 2.0 Tesla were used to cause movement of the nanoparticles. Magnetic fields between about 1.0 and 9.0 Tesla can also be used. The magnetic field used is typically higher if the tissue of interest comprises a greater number of nanoparticles or iron, when compared to tissue with fewer nanoparticles or iron.

Example 2

Colloidal suspensions of SPIO nanoparticles are tissue-specific MRI contrast agents approved by the United States Food and Drug Administration (FDA) for human use in 1997. SPIO particles are also known as Ferumoxides or AMI-25 and their trade name is Feridex® I.V. (USA) and Endorem® (EU). Mean core diameter of these particles is 20 nm and total aggregation diameter is about 100 nm. SPIO nanoparticles comprise nonstoichiometric magnetite crystalline cores, iron, and dextran T-10 coating that is used to prevent aggregation and stabilization in the liver. 80% of injected dose of SPIO nanoparticles accumulate in tissue based macrophages (Kupffer cells) due to the relatively short blood half life compared to ultrasmall SPIO nanoparticles. Uptake of SPIO nanoparticles by macrophage cells is directly proportional to the intravenous injection (IV) concentration, blood half life, and core size.

To evaluate magnetic force on superparamagnetic (SPIO) nanoparticles, magnetic potential energy, U, can be used to calculate force due to application of an external magnetic flux density (B).

$$U = -\frac{1}{2}m \cdot B \quad (1)$$

If a magnetic material is exposed to an external magnetic flux density, B, the individual particles have overall response determined by the magnetic moment, m. The magnetic flux density on magnetic nanoparticles can be written:

$$B = u_0(H + M) \quad (2)$$

where $\mu_0 (4\pi \times 10^{-7} \text{ H/M})$ is the permeability of free space, and M is the magnetic moment per unit volume and H is magnetic field strength. The magnetic moment, m, acting on magnetic volume, V is given by, m=MV. Magnetization of magnetic particles can be classified in terms of the standard relation $M = \chi H$. Therefore, magnetic moment m becomes:

$$m = MV = \chi_s VH = \chi_s VB/\mu_0 \quad (3)$$

In Eq.(3), susceptibility of the SPIO particles $\chi_s$ is dimensionless in SI units and given by dipole density for each paramagnetic material and is an important parameter characterizing magnetic properties of SPIO nanoparticles. From Eq.(1), magnetic energy U, of a SPIO nanoparticles in external magnetic field is given by, $$U = -\frac{1}{2}m \cdot B = -\frac{\chi_s V}{2\mu_0} B^2. \tag{4}$$

Magnetic force acting on SPIO nanoparticles becomes:

$$F = -\nabla U = \nabla\left(\frac{\chi_s V}{2\mu_0} B^2\right) = \chi_s V \nabla\left(\frac{B^2}{2\mu_0}\right). \tag{5}$$

A sinusoidal magnetic flux density that is principally along the z-direction was assumed. Hence, $B(x, y, z; t) = \sin(2\pi f_n t) B_z(z)\hat{k}$ and the magnetic force $F_z$ acting on nanoparticles in the z-direction is given by $$\sum F_z = m\frac{\partial^2 z(t)}{\partial t^2} = F_m - kz(t) - r\frac{\partial z}{\partial t} \tag{6}$$

$$\sum F_z = \frac{\chi_s V_s}{2\mu_0}[1 - \cos(4\pi f_n t)]B_z(z)\frac{\partial B_z}{\partial z} - kz(t) - r\frac{\partial z}{\partial t}, \tag{7}$$

where $F_m$ is magnetic force, $f_n$ is the modulation frequency of the applied sinusoidal magnetic field, kz(t) is an elastic restoring force, and $$r\frac{\partial z}{\partial t}$$

is a viscous drag force that account for the viscoelastic properties of the local tissue environment. The negative sign of the viscous drag and restoring force indicates that this force is in opposite direction to movement z(t). Equation 8 can be written by dividing by the mass, m.

$$\frac{\partial^2 z(t)}{\partial t^2} + \frac{kz(t)}{m} + \frac{r}{m}\frac{\partial z}{\partial t} = \frac{\chi_s V_s}{2m\mu_0}[1 - \cos(4\pi f_n t)]B_z(z)\frac{\partial B_z}{\partial z} \tag{8}$$

Equation 8 can be rewritten using the first terms in the Maclarin series for the magnetic field, $$\frac{\partial^2 z(t)}{\partial t^2} + \frac{r}{m}\frac{\partial z}{\partial t} + \frac{kz(t)}{m} \cong \frac{\chi_s V_s}{2m\mu_0}[1 - \cos(4\pi f_n t)]B_z(0)\frac{\partial B_z(0)}{\partial z} \tag{8}$$

Letting $$a = \frac{\chi_s V_s}{2m\mu_0}B_z(0)\frac{\partial B_z(0)}{\partial z}, c = 4\pi f_n,$$

the second order differential Eq. (8) can be written $$\frac{\partial^2 z(t)}{\partial t^2} + \frac{r}{m}\frac{\partial z}{\partial t} + \frac{kz(t)}{m} = a[1 - \cos(ct)], \tag{9}$$

The Laplace transform can be used to solve the second order differential equation (9), assuming zero initial displacements and velocity to find;

$$s^2 Z(s) + \frac{r}{m}sZ(s) + \frac{k}{m}Z(s) = \frac{a}{s} - \frac{as}{(s^2 + c^2)} \tag{10}$$

$$Z(s) = \frac{\frac{a}{s} - \frac{as}{(s^2+c^2)}}{\left(s^2 + \frac{r}{m}s + \frac{k}{m}\right)} = a\left(\frac{1}{\left(s^2 + \frac{r}{m}s + \frac{k}{m}\right)s} - \frac{s}{\left(s^2 + \frac{r}{m}s + \frac{k}{m}\right)}\right)$$

By computing the sum of the transforms, Z(s) can be derived in Eq (10).

$$z(t) = \frac{ma\left(\begin{array}{c} -2mkc^2 + c^2r^2 + k^2 + c^4m^2 - \cos(ct)k^2 + \\ +\cos(ct)c^2mk - cr\sin(ct)k + \\ \exp\left(-\frac{1}{2}\frac{tr}{m}\right)\left(\begin{array}{c} c^2(km - r^2 - c^2m^2)\cosh\left(\frac{1}{2}\frac{t(r^2-4km)^{\frac{1}{2}}}{m}\right) + \\ \frac{c^2r(3km - r^2 - c^2m^2)\sinh\left(\frac{1}{2}\frac{t(r^2-4km)^{\frac{1}{2}}}{m}\right)}{(r^2-4km)^{\frac{1}{2}}} \end{array}\right) \end{array}\right)}{(k(-2mkc^2 + c^2r^2 + k^2 + c^4m^2)} \tag{11}$$

The displacement z(t) of nanoparticles can be found by using an inverse Laplace transform; the solution includes transient and steady state terms. The initial motion of magnetic nanoparticles is driven by a constant magnetic force and displays a damped transient motion before steady state motion dominates at twice the modulation frequency ($f_n$) of the applied sinusoidal magnetic field. Motion of the nanoparticles at double the modulation frequency originates from the magnetic force being proportional to the product of the field and field-gradient (Eq. 7).

Liver tissues from 12 week old ApoE$^{-/-}$ high fat fed mice were utilized because they contain tissue based macrophages cells. The mice were injected via the jugular vein with either Feridex I.V. (Ferumoxides injectable solutions; Berelex Laboratories, Montville, N.J.) for intravenous administration (1.0, 0.1, and 0.01 mmol Fe/kg body weight) or saline and sacrificed 2 days post intravenous injection. The mice were euthanized with a lethal dose of Ketamine and Xylazine. After euthanizing, abdominal incisions were made to remove the entire liver from the mouse. Portions were cut using a microtome. Physical thickness of the liver samples was 1 mm and 0.5 cm×0.5 cm in lateral dimensions. After completion of the DP-OCT measurements, the mouse livers were embedded in 10% formalin acid, and processed for histology. 5 μm thick sections were cut and stained with Prussian blue to identify iron deposition in liver Kupffer cells in mouse liver tissues. To verify SPIO uptake by macrophage cells from histology slides, Image Pro Plus® (Mediacynemetics Inc., Silver Spring, Md.) was used to measure the total area of liver and accumulated area of SPIO aggregation containing Prussian blue positive.

Figure 6A:
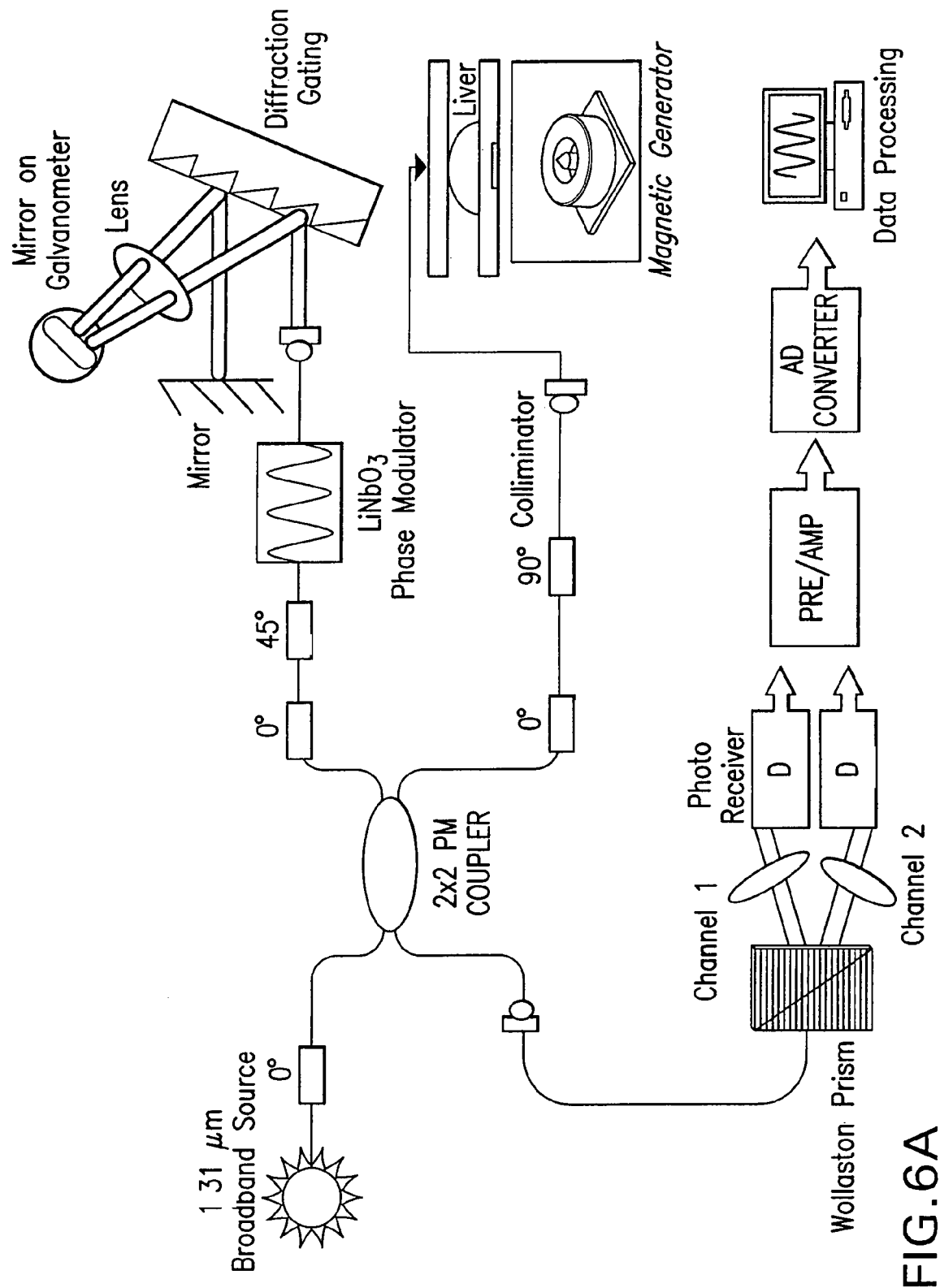
FIG. 6 shows a schematic diagram of a differential phase optical coherence tomography (DP-OCT) system combined with a magnetic field generator: (a) DP-OCT system, (b) collinear configurations of the DP-OCT sample path and design of the magnetic field generator containing a conical iron core.
Figure 6B:
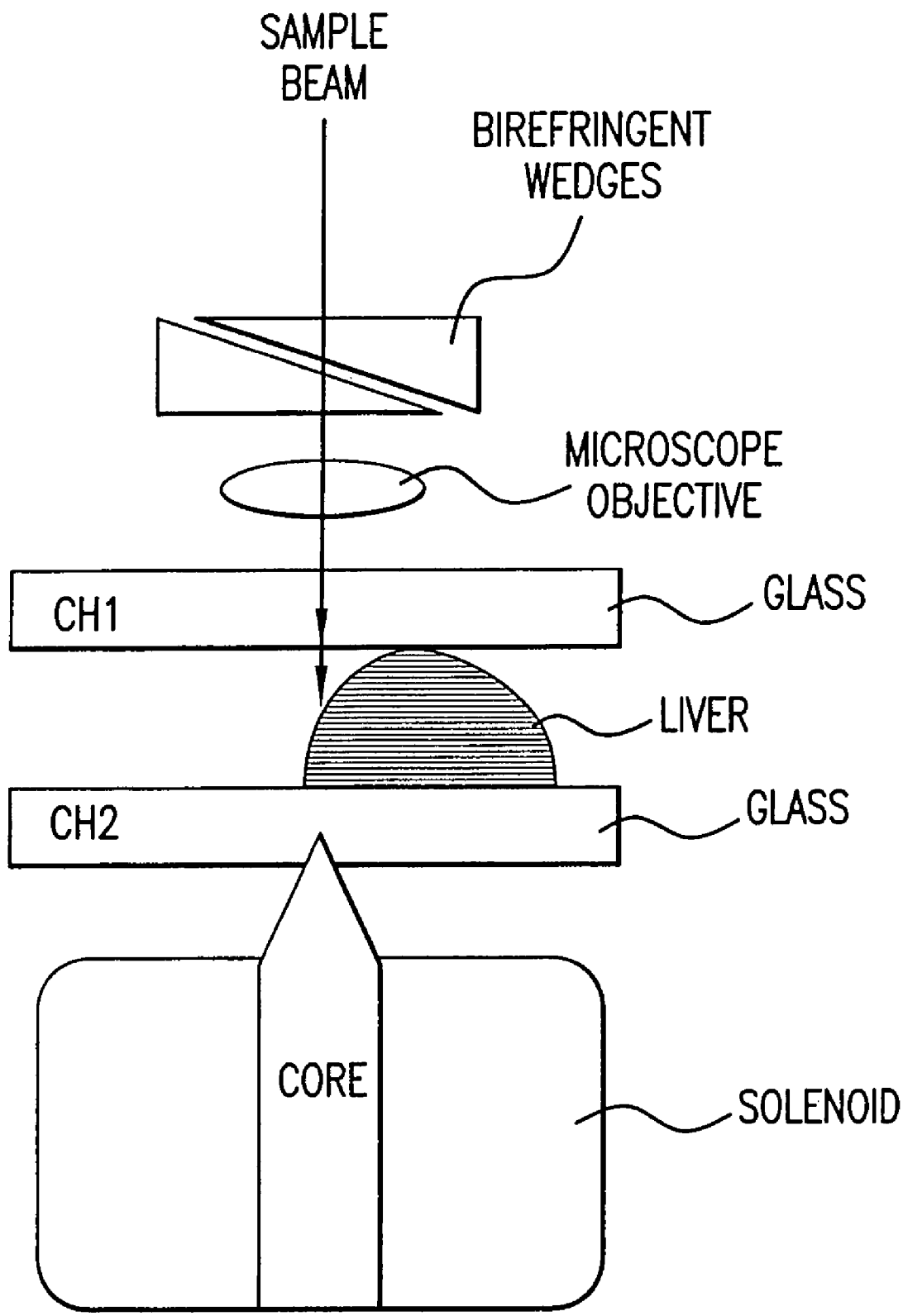

FIGS. 6a and b shows a schematic diagram of a fiber-based dual channel differential phase optical coherence tomography (DP-OCT) system (a), and sample path configuration with a magnetic field generator (b). The magnetic field generator comprises a solenoid, signal generator and current amplifier. A dual-channel Michelson interferometer was used to measure differential phase between light backscattered from a sample by applying a sinusoidal focused magnetic field excitation. Partially polarized light from an optical semiconductor amplifier (AFC Technologies, Rancho Cordova, Calif., central wavelength $\lambda_0$=1.31 μm, FWHM=60 nm, optical coherence length=22 μm) is polarized and coupled into fast and slow axes of a polarization-maintaining (PM) fiber in the input port.

Optical path length change (Δp) in tissue can be calculated from the differential phase (Δϕ) and central wavelength of a broad-band light source ($\lambda_0$=1,310 nm) between the two channels.

$$\Delta p = \frac{\lambda_0}{4\pi}\Delta\varphi \tag{13}$$

The displacement z(t) of tissue-laden nanoparticles driven by a time (t) varying magnetic flux density can be derived the analytic OCT fringe expression, $$I_f = 2\sqrt{I_R I_S}\cos\left[2\pi f_0 t + \frac{4\pi z(t)}{\lambda_0}\right] \tag{12}$$

Where $I_R$ and $I_S$ are the back scattered signals from the reference and sample arms, respectively. $f_0$ is the fringe carrier frequency, and z(t) is the nanoparticles displacement. The OCT fringe signal can be expressed by the nanoparticles displacement equation (12). The two signals recorded from Channel 1 and 2 by the DP-OCT system can be used to measure nanoparticles displacement that represent relative surface tissue displacement between two scanning beams.

Finite element method (FEM) was used to design the magnetic field generator and evaluate space-time magnetic flux density. The magnetic field generator comprises a solenoid (Ledex 6EC, Saia-Burgess Inc., Vernon Hills, Ill.), a function generator (HP 33120A, Hewlett Packard Inc., Palo Alto, Calif.), a current amplifier, and a power supply. FEM calculations (Maxwell SV, Ansoft Inc., Pittsburgh, Pa.) and Teslameter® (Magnetometer®, AlphaLab Inc., Salt Lake City, Utah) measurement indicated that the maximum magnetic flux density at a distance of 1.5 mm from the tip of the iron core was approximately 2 Tesla. The FEM simulation demonstrated that an iron core positioned along the centerline of the solenoid dramatically increased magnetic flux density at the target specimen. Magnetic field distributions from the FEM simulation showed the maximal and principal direction of the magnetic field strength was in the z-direction. The conical iron core provided focusing and substantially increased the magnetic field strength.

Figure 7A:
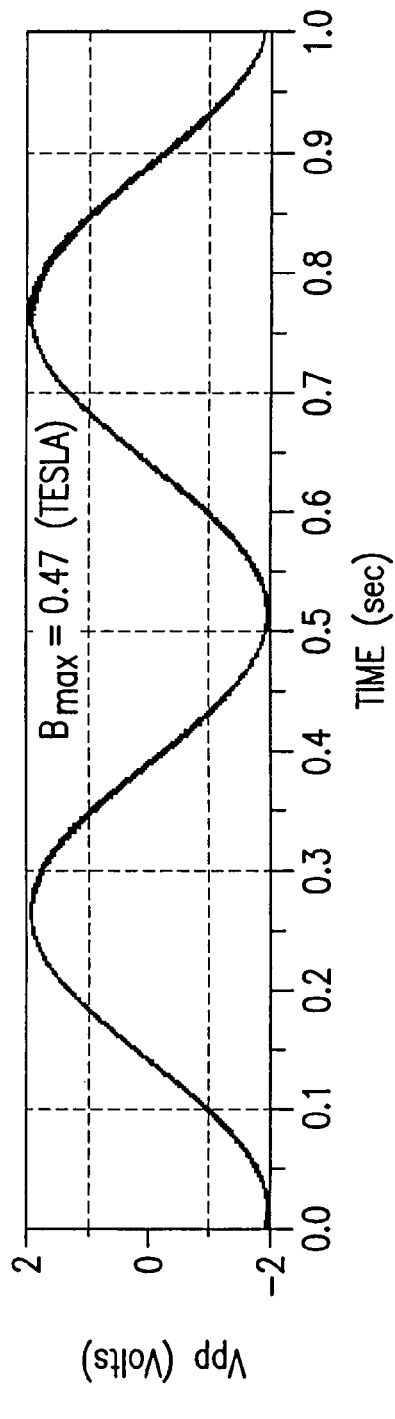
FIG. 7 shows the optical path length change ($\Delta p$) in livers with different SPIO doses (1.0, 0.1 mmol Fe/kg and saline control) using focused magnetic field excitation (2 Hz, 4 $V_{pp}$) (a). Optical path length change ($\Delta p$) in specimens with doses 1.0 mmol Fe/kg SPIO (b), 0.1 mmol Fe/kg SPIO, and a saline control liver. The applied magnetic flux density strength is $B_z=0.47$ Tesla at the liver specimen.
Figure 7B:
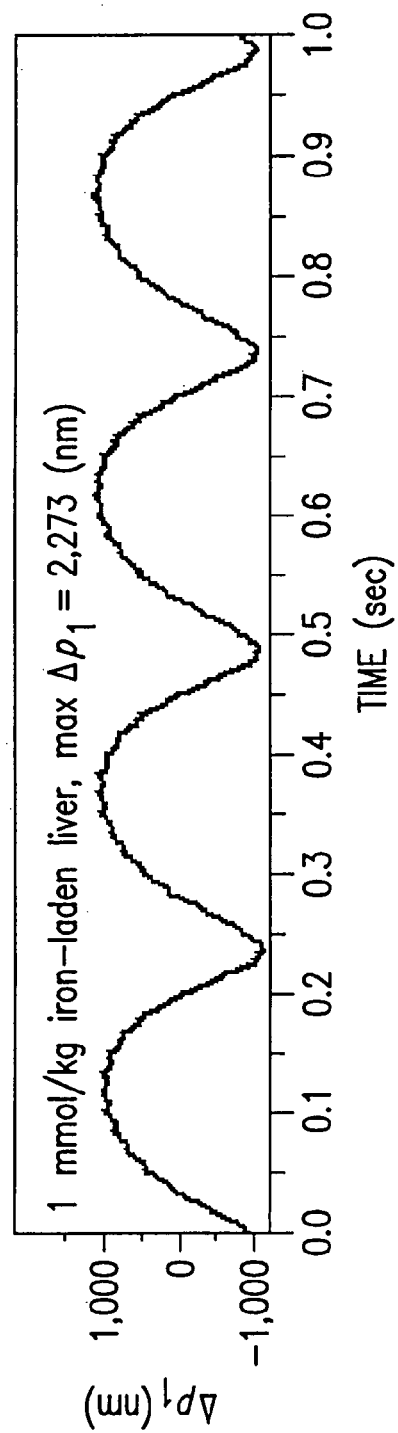
Figure 7C:
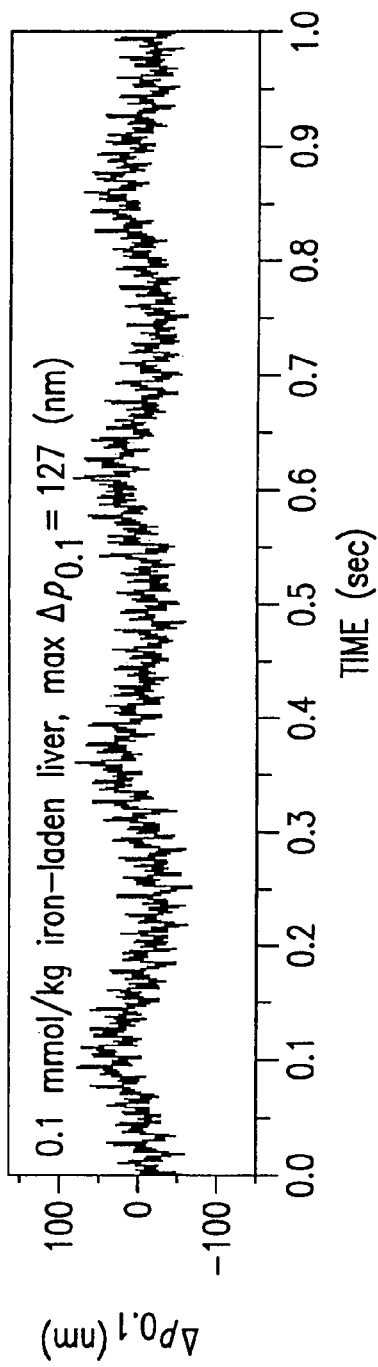
Figure 7D:
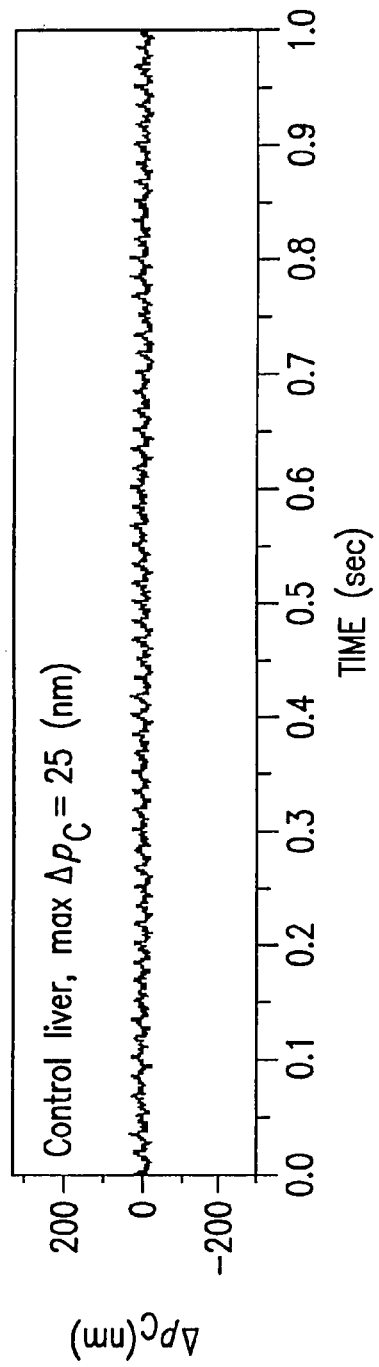

Differential phase OCT (DP-OCT) measurements were performed on isolated liver specimens taken from ApoE−/− mice administrated with different SPIO doses (1.0, 0.1 and 0.01 mmol Fe/kg body weight) and saline control samples. FIG. 7 demonstrates measurements of transient optical path length change (Δp) in specimens at different SPIO doses (1.0, 0.1 mmol Fe/kg body weight) and saline control samples, in response to application of a sinusoidal varying focused magnetic field. FIG. 7(a) shows a magnetic field input ($f_n$=2 Hz), peak-to-peak voltage ($V_{pp}$=4) over a 1 second time period. The maximum magnetic field strength was 0.47 Tesla and maximal tissue displacement by optical path length change (Δp) was 2,273 nm in the 1.0 mmol Fe/kg iron-laden liver. Compared to high dose specimens, 0.1 mmol Fe/kg iron-laden liver showed a maximum optical path length change (Δp) of 127 nm with additive noise visible in recorded signals. Frequency response (4 Hz) of iron-laden livers (FIG. 7(b), (c)) was exactly twice the modulation frequency (2 Hz) as noted earlier. No significant displacement of SPIO nanoparticles was observed in either saline control liver specimens in the FIG. 7(d) or samples at the 0.01 mmol Fe/kg dose (not shown).

Figure 8A:
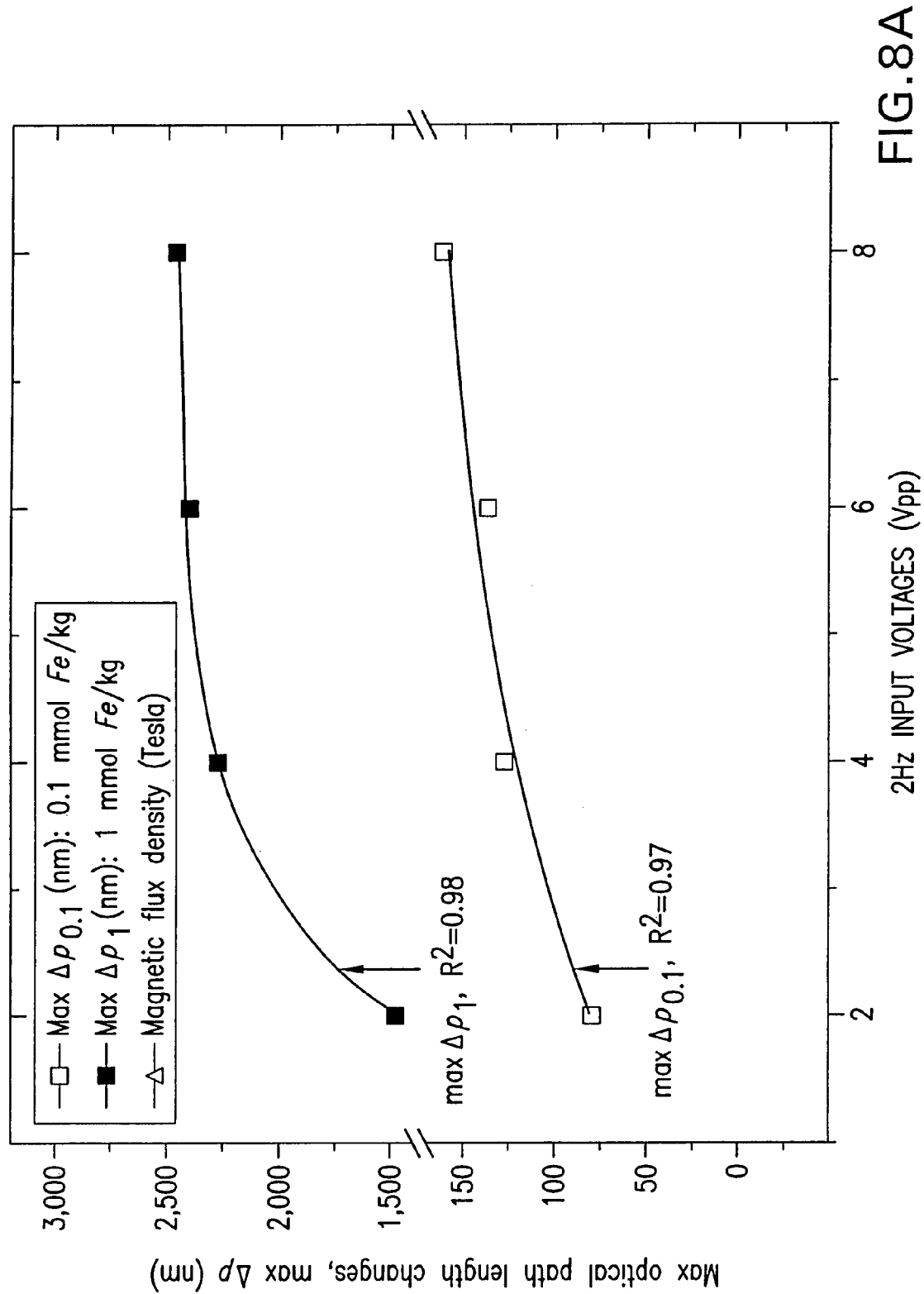
FIG. 8 shows the maximum optical path length change ($\Delta p$) in iron-laden liver specimens due to nanoparticle movement in response to a focused magnetic field for mice injected with various SPIO doses (1.0 and 0.1 mmol Fe/kg). The input frequency is 2 Hz with applied voltage ranging from 2 to 8 $V_{pp}$ (a) and magnetic field strength at each input voltage (b).
Figure 8B:
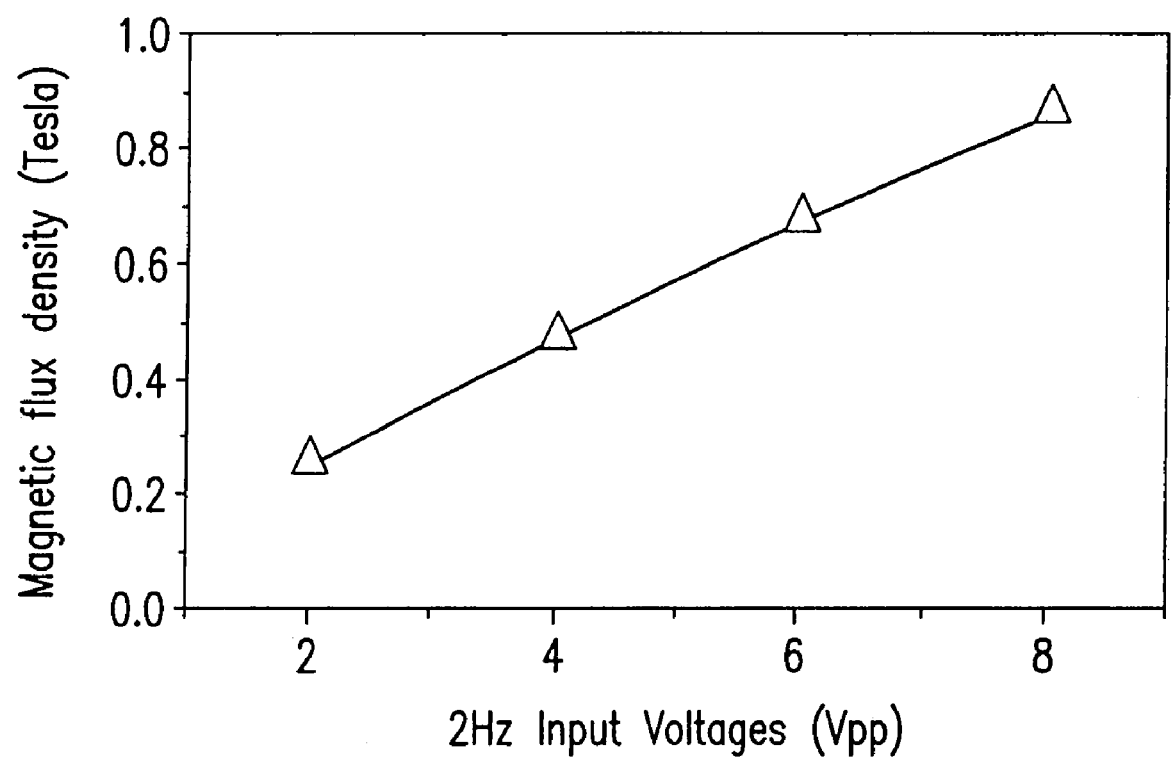

SPIO nanoparticle movement in the iron laden livers (0.1, and 1.0 mmol Fe/kg) was used to observe quantitatively the relationship between optical path length change (Δp) versus different applied magnetic field strengths (FIG. 8(a)). Input frequency used in this experiment was 2 Hz with amplitude from 2 to 8 $V_{pp}$. FIG. 8(b) shows magnetic flux density at the same voltages as in FIG. 8(a). Magnitude of optical path length change (Δp) indicating movement of iron-laden liver depended directly on the SPIO dose concentration, and strength of the external magnetic field.

Optical path length change (Δp) at high frequency modulation (over 100 Hz) was negligible due to limited frequency response of the structures surrounding SPIO nanoparticles. Generally, optical path length change (Δp) due to nanoparticles movement in tissue increased with higher magnetic field strength.

Figure 9C:
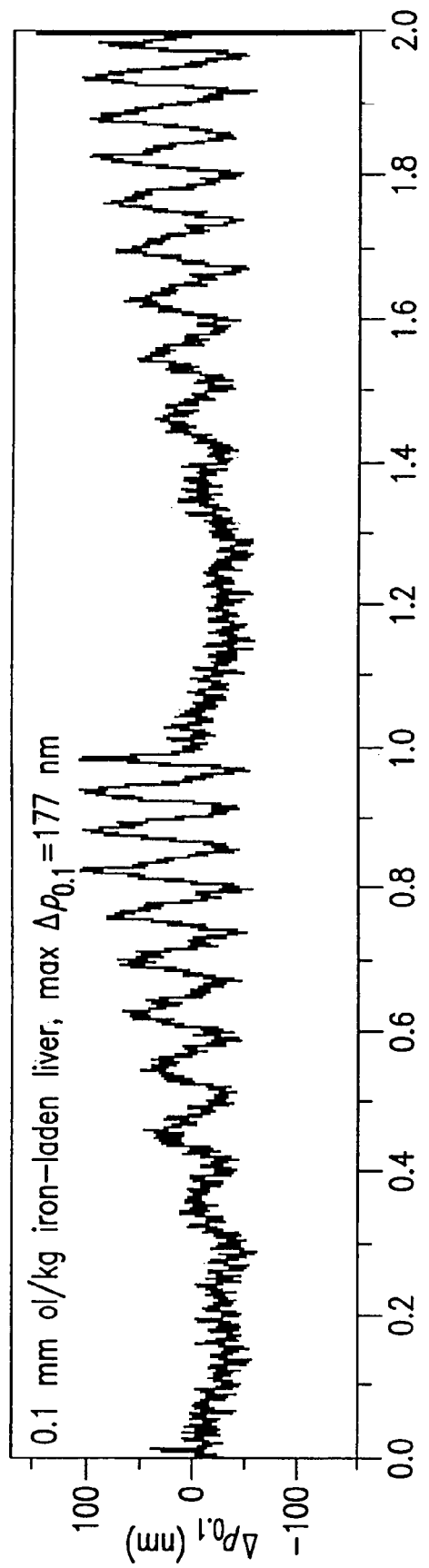
FIG. 9 shows the Optical path length change ($\Delta p$) in iron-laden liver specimens due to nanoparticle movement in response to a focused magnetic field with a swept frequency (1~10 Hz) input for mice injected with various SPIO doses (1.0 and 0.1 mmol Fe/kg). (a). Optical path length change ($\Delta p$) at 1.0 mmol Fe/kg SPIOdose (b), 0.1 mmol Fe/kg SPIO dose (c), and a saline control liver (d). The applied focused magnetic flux density is 1.3 Tesla at the specimen.
Figure 9D:
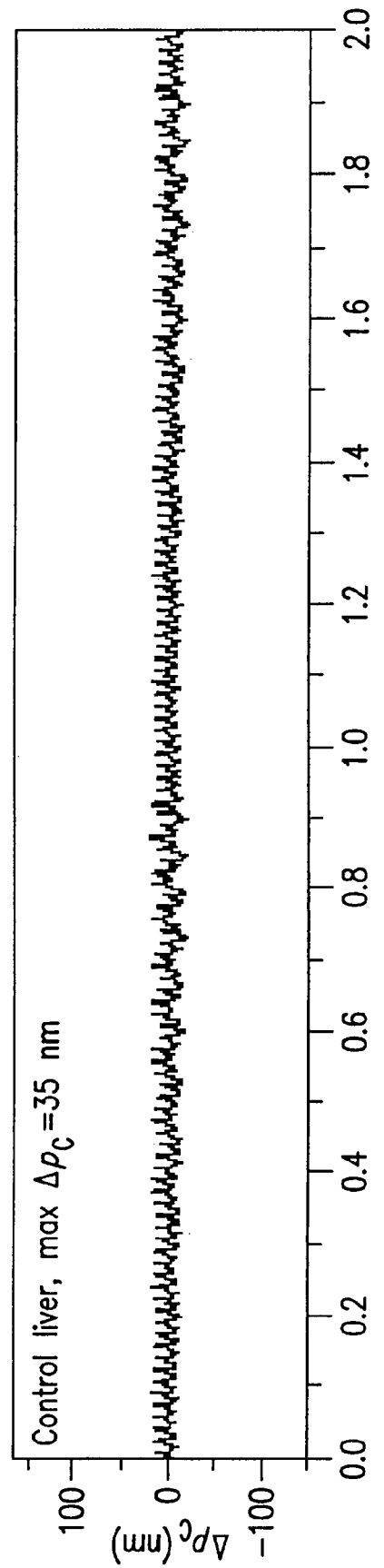

Optical path length change (Δp) in the iron-laden liver (0.1 and 1.0 mmol Fe/kg) can be measured using a swept input frequency as shown in FIG. 9. FIG. 9(a) shows the magnetic field input with a swept frequency from 1 to 10 Hz over a 2 second time-period. Magnitude of the optical path length change (Δp) was 2,318 nm in a high dose liver (1.0 mmol Fe/kg) and 177 nm in a low dose concentration (0.1 mmol Fe/kg), and magnetic field strength was 1.3 Tesla. The frequency response of the force acting on the iron-laden liver is exactly twice the externally applied modulated frequency in FIG. 9(b) and (c). No significant displacement was observed in the saline control liver shown in FIG. 9(d) and 0.01 mmol Fe/kg liver specimens.

Figure 10A:
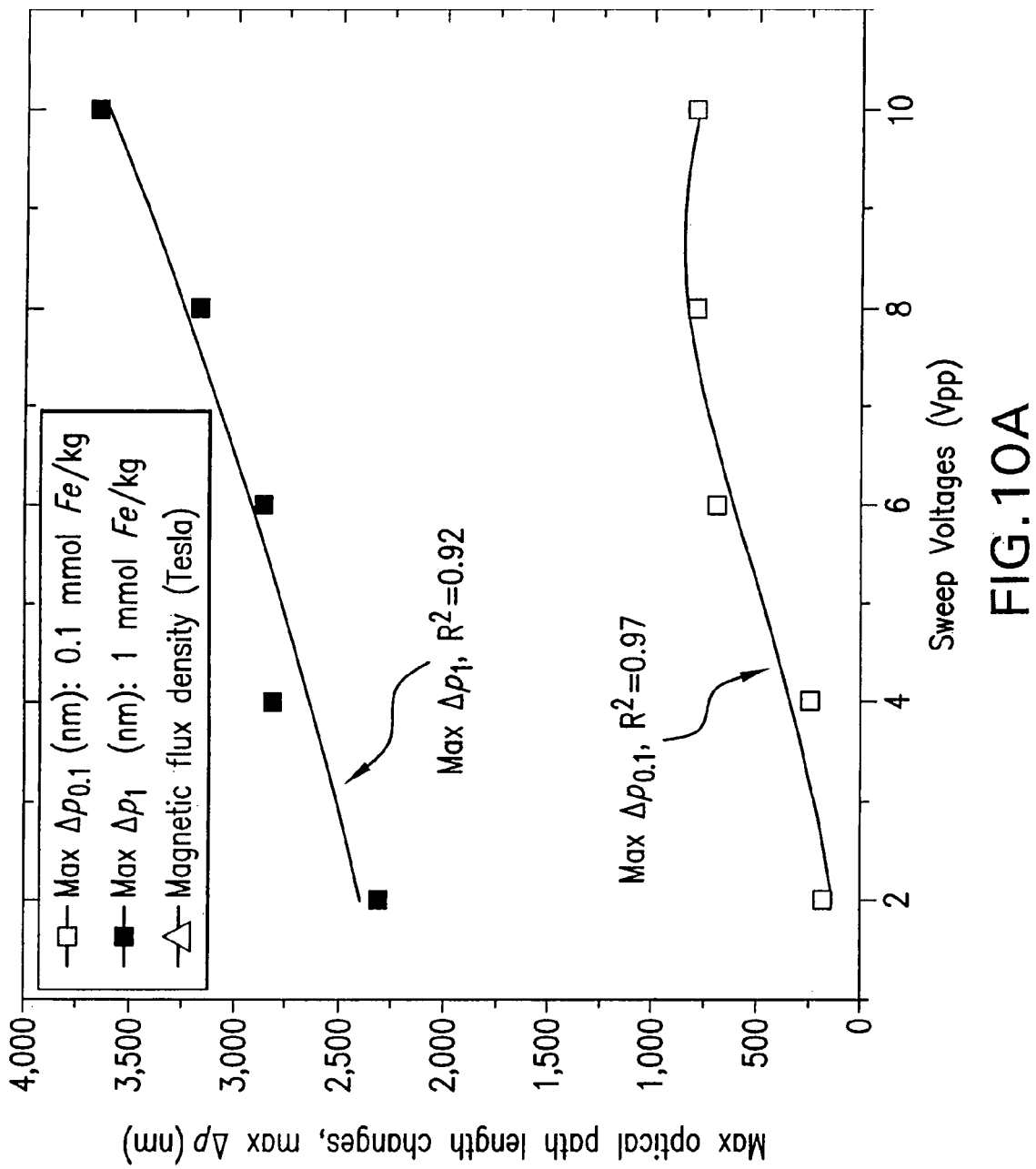
FIG. 10 shows the maximum optical path length change ($\Delta p$) in iron-laden liver specimens due to nanoparticle movement in response to a focused magnetic field with a swept frequency (1~10 Hz) input for mice injected with various SPIO doses (1.0 and 0.1 mmol Fe/kg). Input swept frequency ranged from 1~10 Hz over 2 seconds with input voltages increasing from 2 to 10 $V_{pp}$ (a) and magnetic field strength at each input voltage (b).
Figure 10B:
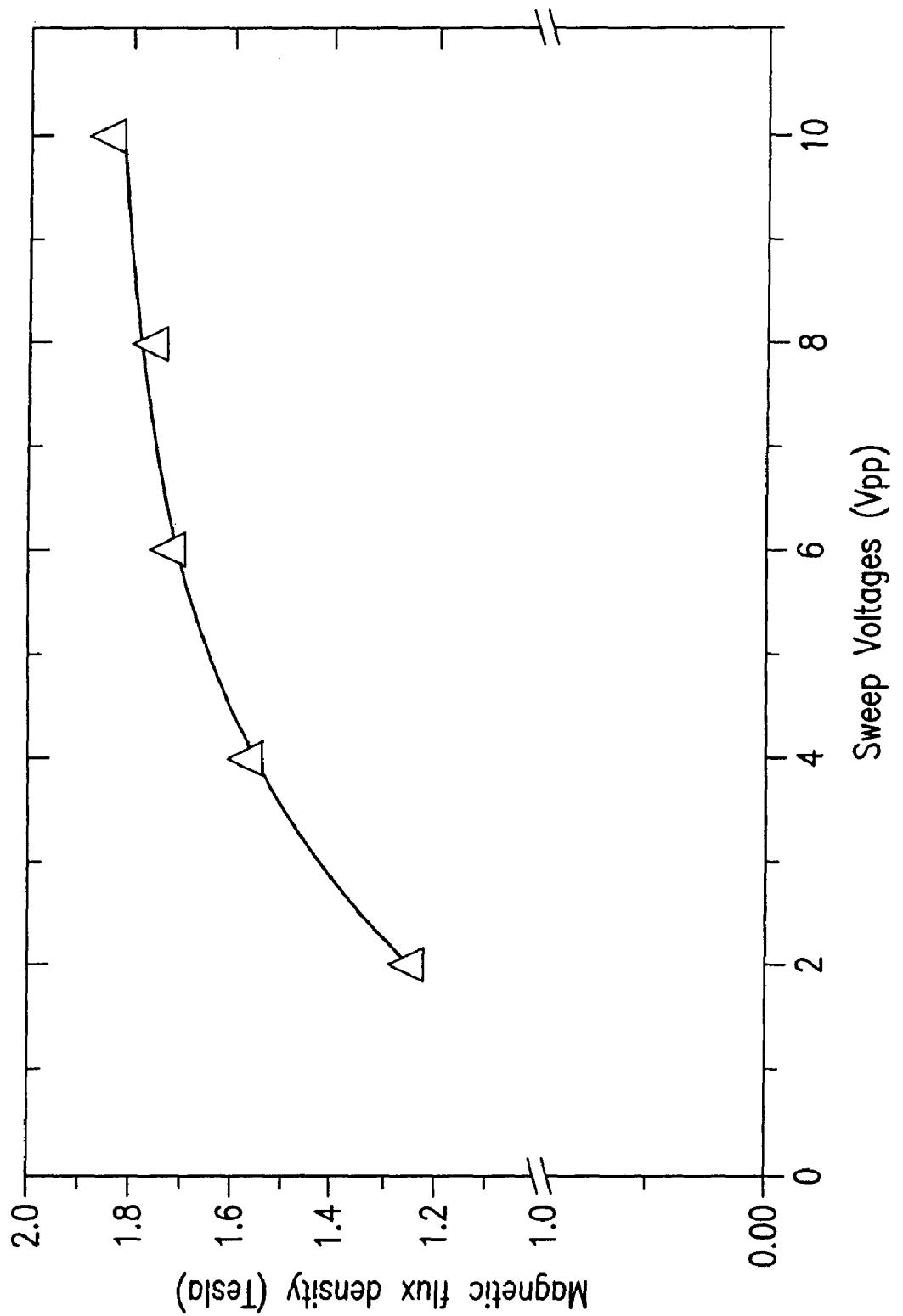
Figure 11A:
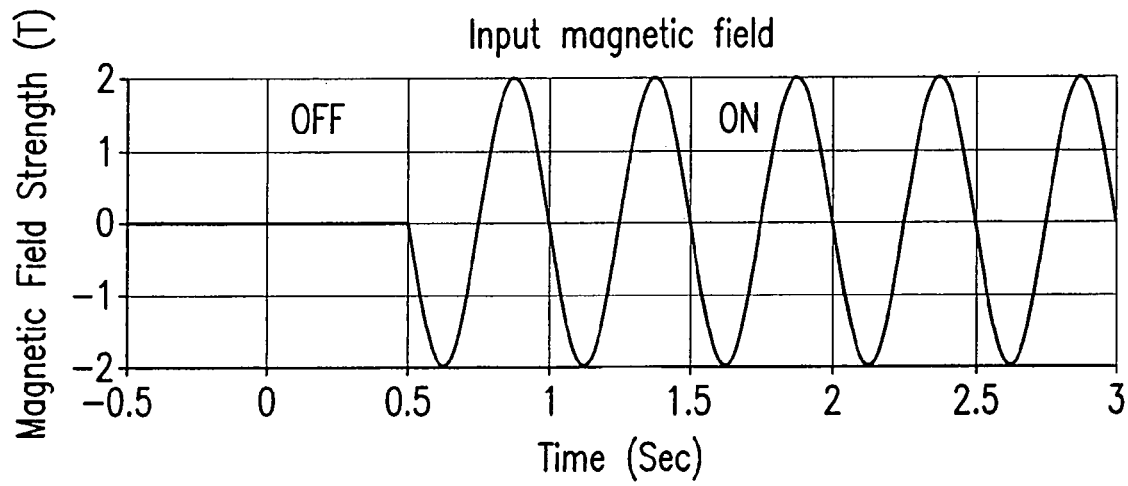
FIG. 11 shows optical path length change ($\Delta p$) in iron-laden rabbit arteries (0.1 Fe/kg) measured in response to 2 Hz frequency sinusoidal input.
Figure 11B:
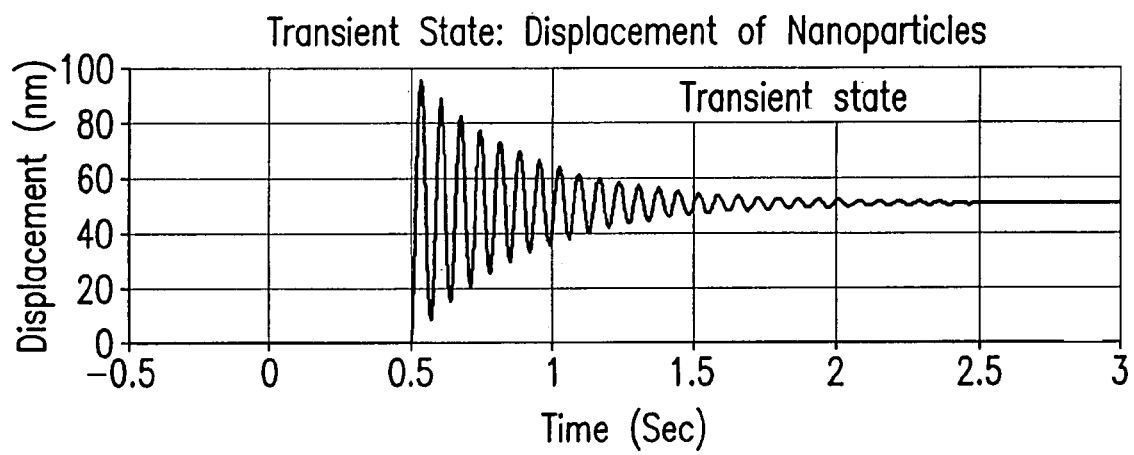
Figure 11C:
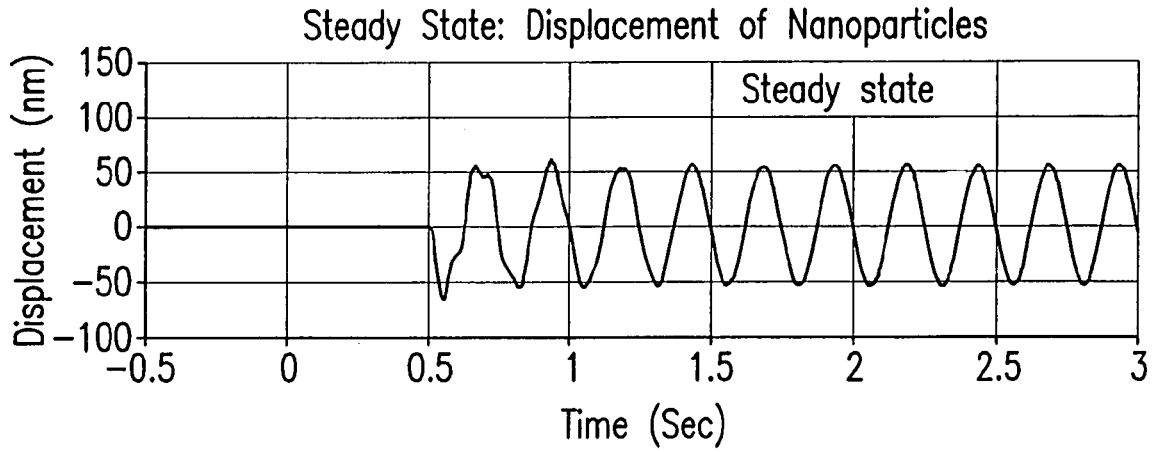
Figure 11D:
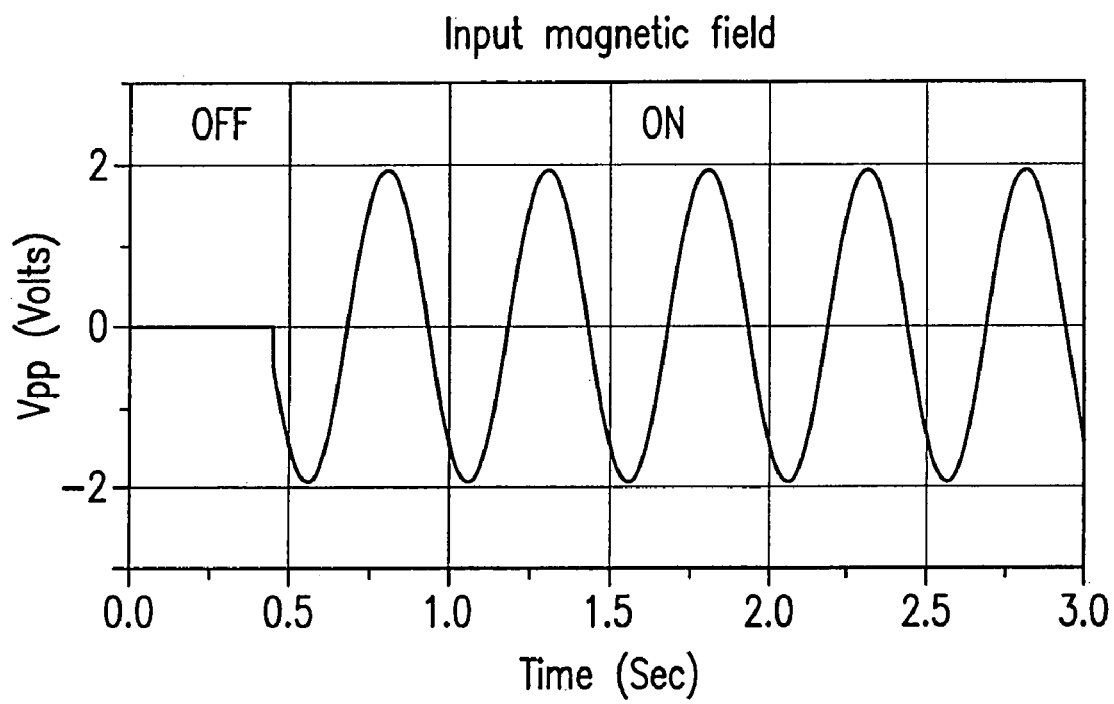
Figure 11E:
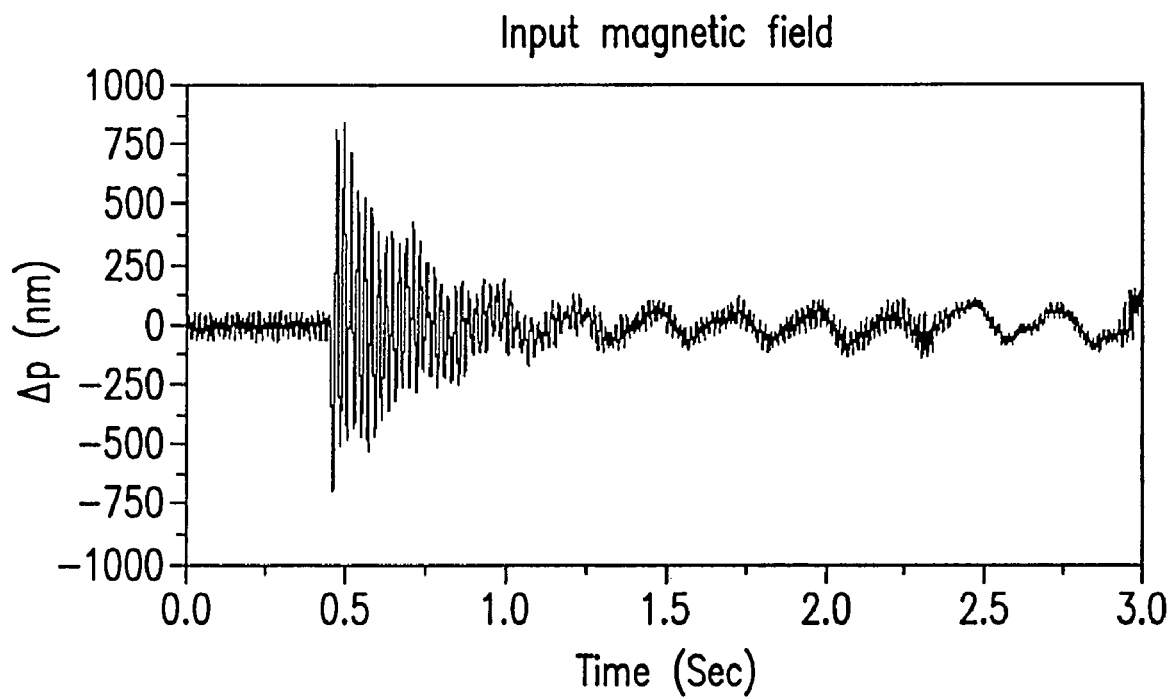

FIG. 10 illustrates SPIO nanoparticle movement measured by optical path length change (Δp) in a iron-laden mouse liver to observe quantitatively the relationship between magnetic response in tissue versus different applied magnetic field strengths with swept frequency ranging from 1~10 Hz over a 2 second time-period. Magnitude of optical path length change (Δp) was larger when input voltage was gradually increased from 2 to 10 $V_{pp}$ during a frequency sweep. Corresponding magnetic field strength at these voltages was 1.24, 1.58, 1.71, 1.75 and 1.84 Tesla, respectively. For a given frequency sweep, maximum optical path length change (Δp) for 0.1 and 1.0 mmol Fe/kg iron-laden liver specimens was 3,700 nm and 750 nm, respectively, at 10 $V_{pp}$, and magnetic field of 1.84 Tesla.

SPIO nanoparticles were identified in histological specimens as blue granules from the Prussian blue stain of iron laden mouse livers. Compared to control liver specimens, iron laden specimens show significant iron accumulation evenly distributed in all observed areas. Although intracellular iron was also observed in control specimens, this natural iron was uniform and homogeneous rather than appearing in granular shapes as SPIO iron nanoparticles. Total SPIO iron area was 5.45% of the histology image as calculated by Image-Pro PLUS 5.1 software (Mediacynernetics Inc., Silver Spring, Md.).

Example 3

Optical path length change (Δp) in iron-laden rabbit arteries (0.1 Fe/kg) was measured in response to 2 Hz frequency sinusoidal input (FIG. 11). FIG. 11(a) shows the magnetic field input with a constant frequency at 2 Hz over a 2.5 second time-period. Magnitude of the optical path length change (Δp) indicated a transient and steady state response. Transient response is evident in the exponentially decaying oscillation in the observed measured optical path length change at times between 0.5-1.0 seconds. Steady state response is evident in the uniform oscillation in the measured optical path length change at times between 1.25-3.0 seconds. Transient response indicates a high frequency (40 Hz-80 Hz) "ringing" oscillation and a damping relaxation time of approximately 0.3 seconds. The steady state frequency response of the force acting on the iron-laden rabbit artery was exactly twice the externally applied modulated frequency in FIG. 11(b).

Example 4

Ultrasmall paramagnetic iron oxide (USPIO) nanoparticles were designed for selective macrophage uptake, highly sensitive phase-sensitive Fourier-domain magneto-mechanical OCT imaging, and tunable near infrared photothermolysis of macrophages. As shown in FIG. 12, the particles can comprise an iron oxide core for magnetic properties coated with a gold shell for near infrared absorption, and an outer coating of dextran for selective uptake by macrophages. A composite diameter less than 40 nm can be used to minimize uptake into the liver and spleen and prolong blood half-life. To further enhance selective macrophage uptake, the dextran coating can be decorated with small molecules such as glycine.

As shown in FIG. 12, the inner gold shell can be about 1-8 nm thick and can be located between an iron oxide core of approximately 5 nm, and an outer dextran shell. The surface plasmon resonance of the gold shell can absorb strongly in the near infra-red at about 700 nm where tissue transmissivity is high due to relatively low scattering and absorption. Since plaque components including water, arterial tissue, and lipid maximally absorb at about 500-600 nm, the gold can be used for particles with selective absorption greater than surrounding plaque components. The gold shell can be attached to the dextran coating (with or without decoration by small molecules such as glycine) to target macrophages in vulnerable plaques.

The particles can be synthesized by reaction of a mixture of Fe(III) and Fe(II) with 1.0 M NaOH at 80° C. for 30 min. in the presence of a surfactant Triton X-100. The inhibition of particle agglomeration by Triton X-100 micelles was found to produce a uniform particle size on the order of 13+0.5 nm. After reaction, the particles can be separated by centrifugation and washed. Next, the particles can be coated with gold shells produced by reduction of a 10-2 M $HAuCl_4$ solution with glucose. The use of a mild reducing agent, glucose, for the adsorbed Au(III) ions on the $Fe_3O_4$ particles can be used to control shell thickness from 4 to 8 nm, by varying the ratio of $Fe_3O_4$ to Au(I). These particles have a large magnetic permeability at 300 K of 2 to 8 emu/g, and can be used for magneto-motive OCT.

Dextran, can be modified with amine groups, and can be adsorbed onto the inner gold shells, as shown in FIG. 12. Aminodextrans are available commercially, for example, from Molecular Probes (Carlsbad, Calif.) at including, 10, 40, 70 and 500 k MW. Aminodextrans can also be synthesized by an established technique to vary the degree of amination per dextran monomer from about 1:5 to about 1:40. The sugar rings in dextran can be oxidized with periodate, $NaIO_4$, to produce aldehyde functionalities. The resulting —RHC═O can be reacted with 1,3-diaminopropane to form a Schiff's base —RC═N—$C_3H_6NH_2$. This base can then be reduced with NaBH4 to form a stable —RC—N—$C_3H_6NH_2$ linkage and to reduce unreacted aldehydes in dextran back to alcohols.

In an alternative exemplary approach for stronger attachment, dextran can be linked covalently to the gold shell on the nanocrystals. The gold can be aminated with 11-amino-1-undecanethiol, $NH_3$+Cl $(CH_2)11SH$. The thiol group can bind strongly to gold. The amino groups on the surface of the gold can be reacted with dextran, which can be partially oxidized by $NaIO_4$. The reaction of the resulting RHC═O (on dextran) with the R'$NH_2$ groups on gold produces a Schiff's base, RC═N—R'. This base can then be reduced with $NaBH_4$ to form a stable R—C—N—R' linkage and to reduce unreacted aldehydes in the dextran back to alcohols.

In a third exemplary alternative, the alcohol functionalities on dextran can be reacted with gold, modified with epoxy surface groups. The epoxy groups can be formed by reaction of chlorohydrin with gold stabilized by 16-mercaptohexadecanoic acid.

Although dextran is selective for macrophages, higher selectivities can be achieved by modification of the particles. For example, dextran-coated cross-linked iron oxide magnetic nanoparticles can be decorated with a library of small molecules for cell-specific targeting. For example, as shown in FIG. 13, the addition of glycine can be used to enhance selectivity of the nanoparticles for activated macrophages. The particles can, however, be modified with various acids and anhydrides including glycine, L-valine, L-Asparagine, citraconic anhydride and acetic anhydride. The synthetic procedures for conjugation of these species are known in the art. The carboxylic acids can be conjugated to aminated dextran in a morpholinoethanesulfonic acid buffer at pH 6.0. The anhydrides can be conjugated in a bicarbonate buffer at pH 8.5. The products can be purified by gel filtration with a Sephadex® G-25 column. The degree of conjugation can be determined by the loss of amine groups. Because typical reagents for determining amine concentrations can be incompatible with iron oxide and ferric and ferrous ions, a procedure based on N-succinimidyl 3-(2-pyridyldithio)-propionate(SPDP) can be used. After reaction with SPDP, the product can be separated from the nanocrystals and analyzed to determine the loss of amine groups, and thus the degree of conjugation.

The gold can be coated directly with aminated dextran, which can then be decorated with the small molecule for macrophage targeting. In the two exemplary alternative approaches, where the gold is coated with dextran, the dextran can be cross-linked with epichlorohydrin and aminated with ammonia and then modified.

Example 5

Figure 16:
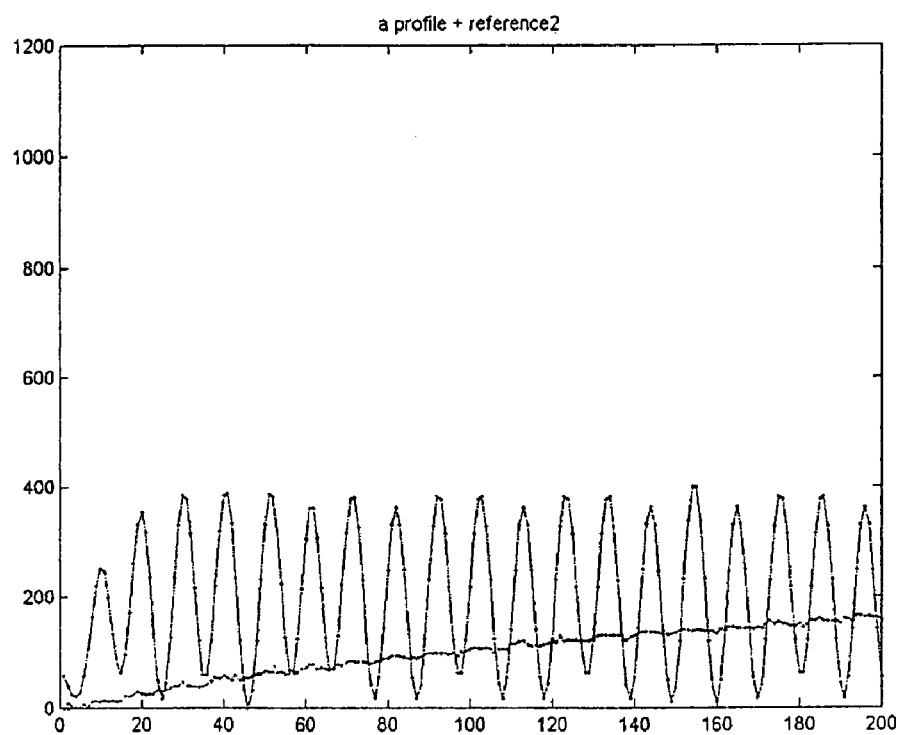
FIG. 16 is the amplitude and phase data used to generate the image displayed in FIGS. 14A and 14B. The figure shows maximum temperature increase ($\Delta T$: ~2.9° C.) of MION rabbit aorta during 2 seconds of 532 nm laser heating (10 Hz modulation frequency, 400 mW).

FIGS. 14A and B show control pulsed laser images from an atherosclerotic rabbit thoracic aorta injected with saline 48 hours prior to imaging with optical coherence tomography. FIGS. 14A and B serve as control images for rabbits that are injected with metallic Iron Oxide Nanoparticles. FIGS. 15A and B show pulsed laser images from an atherosclerotic rabbit thoracic aorta injected with Iron Oxide Nanoparticles 48 hours prior to imaging with optical coherence tomography. FIG. 16 is the Amplitude and Phase data used to generate the image displayed in FIGS. 14A and B. FIG. 16 shows maximum temperature increase of 2.9 degrees C. of saline during 2 seconds of 532 nm laser heating with a 10 Hz modulation frequency, 400 mW. FIG. 17 is the Amplitude and Phase data used to generate the image displayed in FIGS. 15A and B. FIG. 17 shows a maximum temperature increase of 18.6 degrees C. of metallic nanoparticles during 2 seconds of 532 nm laser heating with a 10 Hz modulation frequency and a power 400 mW.

Throughout this application, various publications are referenced. The disclosures of these publications in their entireties are hereby incorporated by reference into this application in order to more fully describe the state of the art to which this invention pertains.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method for detecting and killing a cell, comprising: detecting the cell, wherein the cell comprises a cellular membrane and a metallic composition, using a phase sensitive optical coherence tomographic imaging modality; applying a magnetic field to the cell and the metallic composition to cause a non-lethal change in the cell, wherein the magnetic field has a first predetermined strength and a second predetermined strength, and the first predetermined strength is less than the second predetermined strength; wherein the detecting the cell is performed by detecting the non-lethal change in the cell using the phase sensitive optical coherence tomographic imaging modality during the application of the first and second predetermined strengths of the magnetic field; and heating the metallic composition comprised by the cell by contacting the metallic composition with energy that causes the metallic particle to increase in temperature, wherein the heating is sufficient to kill or lethally injure the detected cell.

2. The method of claim 1, further comprising recording reference phase sensitive interference fringe data prior to the non-lethal change and second phase sensitive interference fringe data during or after non-lethal change; and correlating the reference and second data to quantify the non-lethal change.

3. The method of claim 1, wherein the energy that generates the magnetic field that causes the non-lethal change in the cell and the energy that causes the metallic particle to increase in temperature are of the same type.

4. The method of claim 3, wherein the energy is generated by the same source.

5. The method of claim 3, wherein the energy is generated by a different source.

6. The method of claim 1, wherein the energy that generates the magnetic field that causes non-lethal change in the cell and the energy that causes the metallic particle to increase in temperature are of differing types.

7. The method of claim 6, wherein the energy that causes the increase in temperature is light energy.

8. The method of claim 1, wherein the non-lethal change in the cell is selected from the group consisting of: movement of the cell, movement of the metallic composition, a change in the cellular membrane tension level, a change in the optical refractive index, a change in strain filed surrounding the cell, and a change in the internal strain field of the cell.

9. The method of claim 1, wherein the heating induces apoptosis of the cell.

10. The method of claim 1, wherein the energy that causes the metallic composition to increase in temperature is selected from the group consisting of light, magnetic and sound energy.

11. The method of claim 1, wherein the energy that causes the metallic composition to increase in temperature causes motion of the metallic composition sufficient to heat the metallic composition.

12. The method of claim 1, wherein the cell is located in a subject in proximity to other cells or tissues of the subject, and wherein the energy is light energy of a wavelength that is more highly absorbed by the composition of the cell than by the other cells or tissues in proximity to the cell.

13. The method of claim 12, wherein the energy selectively heats and kills the cell comprising the composition.

14. The method of claim 12, wherein the wavelength of the light energy has a wavelength from about 300 nm to about 2000 nm.

15. The method of claim 1, wherein the phase sensitive optical coherence tomographic imaging modality comprises a probe for transmitting and receiving light energy to and from the cell.

16. The method of claim 15, wherein the probe can transmit a first light energy for detecting the cell and a second light energy for killing the cell.

17. The method of claim 15, wherein the probe further comprises a magnetic source for applying the magnetic field to the cell.

18. The method of claim 1, wherein the magnetic field is applied to the cell from a magnetic source located external to the subject.

19. The method of claim 1, wherein the metallic composition is located within the cell.

20. The method of claim 1, wherein the metallic composition is targeted to a location on the cellular membrane of the cell.

21. The method of claim 1, wherein the metallic composition has a non-zero magnetic susceptibility.

22. The method of claim 21, wherein the metallic composition comprises a material selected from the group consisting of iron oxide, iron, cobalt, nickel, and chromium.

23. The method of claim 22, wherein the metallic composition comprises iron and gold.

24. The method of claim 1, wherein the metallic composition comprises a plurality of metallic nanoparticles.

25. The method of claim 24, wherein the nanoparticles are substantially spherical and have a diameter from about 0.1 nanometers (nm) to about 1000.0 nm.

26. The method of claim 24, wherein the nanoparticles are asymmetrical in shape.

27. The method of claim 26, wherein the largest cross sectional dimension of the nanoparticles is from about 0.1 nanometers (nm) to about 1000.0 nm in length.

28. The method of claim 24, wherein the cell is located within a subject and the metallic composition is administered to the subject.

29. The method of claim 28, wherein the cell is a macrophage and wherein at least one nanoparticle is located within the macrophage.

30. The method of claim 29, wherein the macrophage is located in an atherosclerotic plaque within the subject.

31. The method of claim 29, wherein the macrophage is located within the eye of the subject.

32. The method of claim 28, wherein at least one of the nanoparticles is configured to localize to a target site within the subject.

33. The method of claim 32, wherein the target site is a neoplastic cell.

34. The method of claim 32, wherein the target site is an extracellular domain of a protein.

35. The method of claim 32, wherein in the cell comprises the target site, and wherein the cell is located in the subject at an anatomical location selected from the group consisting of a lung, bronchus, intestine, stomach, colon, eye, heart, blood vessel, cervix, bladder, urethra, skin, muscle, liver, kidney, and blood.

36. The method of claim 32, wherein the cell comprises the target site and wherein the cell is selected from the group consisting of a neoplastic cell, a squameous cell, a transitional cell, a basal cell, a muscle cell, an epithelial cell, and a mucosal cell.

37. The method of claim 32, wherein the nanoparticle comprises an antibody or fragment thereof.

38. The method of claim 37, wherein the antibody or fragment thereof is conjugated to the surface of the nanoparticle.

39. The method of claim 32, wherein the nanoparticle comprises a peptide or a fragment thereof 40. The method of claim 39, wherein the peptide or fragment thereof is conjugated to the surface of the nanoparticle.

41. The method of claim 1, wherein detecting the change in the cell caused by the interaction of the magnetic field with the metallic composition comprises generating a phase sensitive optical coherence tomographic image, wherein the image comprises one or more lines of phase sensitive light energy data captured using the phase sensitive optical coherence tomography modality, and wherein at least one line is captured during the application of the magnetic field.

42. The method of claim 41, wherein generating one or more data line comprises:
generating light energy; transmitting at least a first portion of the generated light energy onto a reference reflector wherein at least a portion of the transmitted first portion of light energy is reflected by the reference reflector; transmitting at least a second portion of the generated light energy to contact the cell wherein at least a portion of the light energy that contacts the cell is reflected by the cell; receiving the light energy reflected by the reference reflector and by the cell; combining the received light energy from the cell and reference reflector, wherein the received light energy interferes; and processing the combined light energy to produce the phase sensitive optical coherence data line.

43. The method of claim 42, wherein a movement of the cell caused by the interaction of the magnetic field with the metallic composition is detected.

44. The method of claim 42, wherein a change in the cellular membrane's tension level or internal strain field caused by the interaction of the magnetic field with the metallic composition is detected.

45. The method of claim 42, wherein the image produced has a phase sensitive resolution of at least about 30.0 nanometers (nm), 25.0 nm, 15.0 nm, 10.0 nm, 5.0 nm, 4.0 nm, 3.0 nm, or 2.0 nm.

46. The method of claim 41, wherein generating one or more data lines comprises:
generating light energy; transmitting at least a first portion of the generated light energy onto a reference reflector wherein at least a portion of the transmitted first portion of light energy is reflected by the reference reflector; transmitting at least a second portion of the generated light energy to contact the metallic composition wherein at least a portion of the light energy that contacts the metallic composition is reflected by the composition; receiving the light energy reflected by the reference reflector and by the composition; combining the received light energy, wherein the received light energy interferes; and processing the combined light energy to produce the phase sensitive optical coherence data line.

47. The method of claim 46, wherein a movement of the metallic composition caused by the interaction of the magnetic field with the metallic composition is detected.

48. The method of claim 46, wherein the image produced has a phase sensitive resolution of at least about 30.0 nanometers (nm), 25.0 nm, 15.0 nm, 10.0 nm, 5.0 nm, 4.0 nm, 3.0 nm, or 2.0 nm.

49. The method of claim 41, wherein a plurality of phase sensitive light energy data lines are captured and used to construct the image.

50. The method of claim 49, wherein the plurality of phase sensitive light energy data lines are spatially and temporally distinct and wherein the image comprises a B-mode image frame comprising at least two of the lines.

51. The method of claim 49, wherein the plurality of phase sensitive light energy data lines are temporally distinct and wherein the image comprises a M-mode image comprising at least two of the lines.

52. The method of claim 49, wherein at least a first phase sensitive light energy data line is captured prior to the application of the magnetic field, wherein at least a second phase sensitive light energy data line is captured during application of the magnetic field, and wherein the captured lines are used to create the image.

53. A method for detecting and killing a cell, comprising:
detecting the cell, wherein the cell comprises a cellular membrane and a metallic composition, using a phase sensitive optical coherence tomographic imaging modality;
heating the metallic composition comprised by the cell by contacting the metallic composition with energy that causes the metallic particle to increase in temperature, wherein the heating is sufficient to kill or lethally injure the detected cell;
the detecting step further comprises causing a non-lethal change in the cell by contacting the metallic particle with energy sufficient to cause the non-lethal change in the cell, the energy sufficient to cause the non-lethal change in the cell is a magnetic field and wherein the cell is detected by detecting the non-lethal change in the cell;

wherein detecting the non-lethal change in the cell caused by the interaction of the magnetic field with the metallic composition comprises generating a phase sensitive optical coherence tomographic image, wherein the image comprises one or more lines of phase sensitive light energy data captured using the phase sensitive optical coherence tomography modality, and wherein at least one line is captured during the application of the magnetic field;

wherein a plurality of phase sensitive light energy data lines are captured and used to construct the image;

capturing at least a first phase sensitive light energy data line during the application of the magnetic field, wherein the magnetic field has a first predetermined strength; capturing at least a second phase sensitive light energy data line during application of a second magnetic field having a second predetermined strength; wherein the first predetermined strength is less than the second predetermined strength; and processing the captured lines to create the image.

54. A system for detecting and killing a cell, comprising: a phase sensitive optical coherence tomographic imaging modality for detecting the cell, wherein the cell comprises a cellular membrane and a metallic particle; a magnetic field configure to cause a non-lethal change in the cell, wherein the magnetic field includes a first predetermined strength and a second predetermined strength and the first predetermined strength is less than the second predetermined strength; the phase sensitive optical coherence tomographic modality is configured to detect the change in the cell caused by the interaction of the magnetic field with the metallic composition by an image; the image comprises one or more lines of phase sensitive light energy data captured using the phase sensitive optical coherence tomography modality, and wherein at least one line is captured during the application of the first and second predetermined strengths of the magnetic field; the phase sensitive optical coherence tomographic modality is configured to process the captured lines to create the image; and an energy source for heating the metallic particle, wherein the heating is sufficient to kill or lethally injure the detected cell.

55. The system of claim 54, wherein the energy source that generates the magnetic field for causing the non-lethal change in the cell and the energy source for heating the metallic particle are of the same type.

56. The system of claim 54, wherein the energy source that generates the magnetic field for causing the non-lethal change in the cell and the energy source for heating the metallic particle are the same source.

57. The system of claim 54, wherein the energy source that generates the magnetic field for causing the non-lethal change in the cell and the energy source for heating the metallic particle are different sources.

58. The system of claim 54, wherein the energy source that generates the magnetic field for causing the non-lethal change in the cell and the energy source for heating the metallic particle are of different types.

59. The system of claim 58, wherein the energy source for causing the heating generates or transmits light energy.

60. A system for detecting and killing a cell, comprising: a magnet for applying a magnetic field to a cell; a phase sensitive optical coherence tomographic imaging modality for detecting the cell while it is in the presence of the magnetic field; wherein the magnetic field applied to the cell includes a first predetermined strength and a second predetermined strength and the first predetermined strength is less than the second predetermined strength; the phase sensitive optical coherence tomographic modality is configured to detect the change in the cell caused by the interaction of the magnetic field with the metallic composition by an image; the image comprises one or more lines of phase sensitive light energy data captured using the phase sensitive optical coherence tomography modality, and wherein at least one line is captured during the application of the first and second predetermined strengths of the magnetic field; the phase sensitive optical coherence tomographic modality is configured to process the captured lines to create the image; and an energy source for applying energy capable of heating a metallic composition comprised by the cell, wherein the heating is sufficient to kill or lethally injure the detected cell.

61. The system of claim 60, wherein the energy source is selected from the group consisting of a light emitting source, magnetic field emitting source and sound emitting source.

62. The system of claim 60, wherein the energy source is capable of heating the metallic composition by causing motion of the metallic composition sufficient to heat the metallic composition.

63. The system of claim 60, wherein the phase sensitive optical coherence tomographic imaging modality comprises a probe for transmitting and receiving light energy to and from the cell.

64. The system of claim 63, wherein the probe further comprises the magnet for applying the magnetic field to the cell.

65. The system of claim 60, wherein the magnet of the system is located external to the subject.

66. The system of claim 60, wherein the phase sensitive optical coherence tomographic imaging modality comprises: a light source, a light splitter, a probe and a reference reflector, wherein light energy generated by the light source can be transmitted to and split by the splitter for transmission to the reference reflector and to the probe, wherein the probe is configured to transmit at least a portion of the light energy transmitted thereto into a target cell and to receive reflected light energy from the target cell, and wherein the reference reflector is configured to reflect at least a portion of the light energy transmitted thereto; and a processor for processing reflected light energy from the reference reflector and light energy received by the probe to produce a phase sensitive optical coherence tomography image.

67. The system of claim 66, wherein the probe further comprises a single optical fiber and a rotary reflector in optical communication with the single optical fiber.

68. The system of claim 66, wherein the probe comprises the reference reflector.

* * * * *